US006210340B1

(12) United States Patent
Amano et al.

(10) Patent No.: US 6,210,340 B1
(45) Date of Patent: Apr. 3, 2001

(54) BLOOD PULSE MEASURING DEVICE, PULSATION MEASURING DEVICE, AND PRESSURE MEASURING DEVICE

(75) Inventors: Kazuhiko Amano, Yokohama; Koji Higuchi, Okaya; Osamu Takahashi, Matsumoto; Tsukasa Funasaka, Suwa; Hajime Miyazaki, Matsumoto; Masahito Yoshino, Nagano-ken, all of (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/117,677

(22) PCT Filed: Mar. 24, 1998

(86) PCT No.: PCT/JP98/01276

§ 371 Date: Apr. 20, 1999

§ 102(e) Date: Apr. 20, 1999

(87) PCT Pub. No.: WO98/42254

PCT Pub. Date: Oct. 1, 1998

(30) Foreign Application Priority Data

| | | | |
|---|---|---|---|
| Mar. 25, 1997 | (JP) | | 9-090237 |
| Apr. 30, 1997 | (JP) | | 9-126316 |
| Oct. 31, 1997 | (JP) | | 9-301331 |

(51) Int. Cl.$^7$ ........................................................ A61B 5/02
(52) U.S. Cl. ............................................ 600/500; 600/485
(58) Field of Search ................................. 600/481, 490, 600/499, 500, 501–502, 503, 485

(56) References Cited

U.S. PATENT DOCUMENTS

| | | | | |
|---|---|---|---|---|
| 4,901,733 | * | 2/1990 | Kaida et al. ........................... | 600/485 |
| 4,928,700 | * | 5/1990 | Harada ................................... | 600/485 |
| 4,951,679 | * | 8/1990 | Harada ................................... | 600/485 |
| 5,101,829 | * | 4/1992 | Fujikawa et al. ..................... | 600/485 |
| 5,103,831 | * | 4/1992 | Niwa ..................................... | 600/485 |
| 5,119,822 | * | 6/1992 | Niwa ..................................... | 600/485 |
| 5,183,050 | * | 2/1993 | Kawamura ............................ | 600/485 |
| 5,273,046 | * | 12/1993 | Butterfield et al. ................... | 600/485 |
| 5,467,771 | * | 11/1995 | Narimatsu et al. .................... | 600/485 |
| 5,497,779 | * | 3/1996 | Takaya et al. ........................ | 600/485 |

FOREIGN PATENT DOCUMENTS

| | | |
|---|---|---|
| 49-87688 | 7/1974 | (JP) . |
| 53-23182 | 3/1978 | (JP) . |
| 51-25664 | 8/1978 | (JP) . |
| 61-109503 | 7/1986 | (JP) . |
| 1-155828 | 6/1989 | (JP) . |
| 2-79904 | 6/1990 | (JP) . |
| 4-15037 | 1/1992 | (JP) . |
| 4-67839 | 3/1992 | (JP) . |
| 4-67840 | 3/1992 | (JP) . |
| 4-102438 | 4/1992 | (JP) . |
| 4-108424 | 4/1992 | (JP) . |
| 4-51909 | 5/1992 | (JP) . |
| 6-197873 | 7/1994 | (JP) . |
| 6-324074 | 11/1994 | (JP) . |

* cited by examiner

*Primary Examiner*—Cary O'Connor
*Assistant Examiner*—Navin Natnithithadha

(57) ABSTRACT

A pulse wave measuring device is provided with a plurality of pulse wave measuring units. Each pulse wave measuring unit has a supporting member to which a beam of a pressure measuring device is attached. Contact portions at the distal end of the beam is in contact with the patient's arm, so that piezoelectric elements mounted on the beam measures the stress variation according to pulsation of the patient's radial artery. The supporting member has two pressing legs between which the contact portions of the beam are situated. The distal ends of the pressing legs are also pressed against the patient's arm. The pressing legs are harder than the radial artery. The interval between the pressing legs can be altered by handling a micrometer head. The contact portions are situated back from the distal ends of the pressing legs.

94 Claims, 28 Drawing Sheets

$I_{out}/I_{in} = 1 - kC\Delta L$ k: ABSORPTION COEFFICIENT
L: MATERIAL THICKNESS

DIAGRAM FOR DESCRIBING
LAMBERT-BEER LAW $I_{out}/I_{in} = (1 - kC\Delta L)^5$ k: ABSORPTION COEFFICIENT
L: MATERIAL THICKNESS

DIAGRAM FOR DESCRIBING
LAMBERT-BEER LAW

DIAGNOSTICIAN'S FINGERTIP

BLOOD PULSE MEASURING DEVICE, PULSATION MEASURING DEVICE, AND PRESSURE MEASURING DEVICE

TECHNICAL FIELD

The present invention relates to a device for measuring blood pulse wave, a device for measuring pulsation, and a pressure measuring device.

TECHNICAL BACKGROUND

A "bloodpulse wave" is the blood pressure wave, which is pumped out from the heart and propagates through a blood vessel, or the vibration of the blood vessel wall generated by the blood pressure wave. Since various medical information, for example, the vital condition of the heart, can be obtained by detecting and analyzing blood pulse waves, it has been carried out to diagnose blood pulse wave by the diagnostician's sense of touch traditionally in Oriental medicine.

More specifically, the diagnostician presses the patient's wrist by his fingers and measures blood pulse wave of the radial artery by the finger's sense of touch in Oriental medicine. Due to the finger pressure, the amplitude of the sensed pulse wave changes, so that the changing characteristic of the amplitude of pulse wave can be a diagnostic parameter in the field of Oriental medicine.

FIGS. 22A to 22C respectively show curves indicating amplitude variations of the sensed pulse wave due to pressure change. These curves are called "tendency curves" in Oriental medicine.

The tendency curve in FIG. 22A has a peak at the center thereof. That is, when a medium pressure is applied to the artery, pulse wave can be detected clearly. This kind of curve is categorized into a "normal curve", and this is a characteristic of normal pulse wave ("Ping-mai") obtained from a healthy human body.

The tendency curve in FIG. 22B has a peak at the left thereof. This kind of curve is categorized into a "gradual decrease curve". In this case, pulse wave can be detected clearly when a weak pressure is applied, but pulse wave weakens when the applied pressure rises. This phenomenon is called "Hua" and this kind of pulse wave is called "Hua-mai".

The tendency curve in FIG. 22C has a peak at the right thereof. This kind of curve is categorized into an "gradual increase curve". In this case, pulse wave can not be detected clearly when a weak pressure is applied, but it can be detected when the pressure applied by the diagnosticians finger rises. This phenomenon is called "Xuan" and this kind of pulse wave is called "Xuan-mai".

The Hua-mai is caused by an abnormality in the flow of blood in which the movement of the blood through the vessel becomes extremely smooth due to some kinds of illness. The Xuan-mai is on the other hand caused by an increase in the tension in the walls of the blood vessels because of other kinds of illness. Thus, the correlation between the given initial pressure and the wave amplitude is an important factor for evaluating patient's condition in the pulse wave diagnosis.

However, there are individual differences among patients. Namely, there are fat patients and thin patients. In addition, each patient has his or her own muscular and fat distribution and elasticity in the flesh. Therefore, although the same pressure is given, the displacement of the organism tissues is dependent on the individuality. The amplitude of pulse wave relates to the distance between the skin surface and the blood vessel when the pressure is applied, and to the configuration of the pressed blood vessel. In manual diagnosis by a skilled diagnostician, he controls the pressure by himself, thereby judging that the patient's pulse wave belongs to Ping-mai, Hua-mai or, Xuan-mai. Therefore, it is also preferable to optionally adjust the initial pressure given to the measured blood vessel for mechanical diagnosis.

Conventionally, devices for measuring blood pulse wave comprise pressure measuring devices including pressure sensors, such as piezoelectric elements or strain gauges, which can be into contact with the organism's skin, e.g., the skin portion over the radial artery. The pressure sensor is strained due to the stress varying by the pulsation of the blood vessel, and outputs pulsation signals corresponding to the stress fluctuations.

In order to measure pulse wave under stable condition, these pressure measuring devices should be pressed against the organism's skin at a pressure. As disclosed in JP-A-4-102438, JP-A-4-108424, JP-A-4-67839, and JP-A-4-67840, pressure measuring devices are usually mounted on cuffs which are elastic bags wound around the patients, arms, and are pressed on the organisms' surfaces by compulsorily introducing air into the cuffs.

However, it is difficult to adjust the initial pressure on the blood vessel using with such cuffs for pressing the pressure measuring devices on the organisms, surfaces since the flat surfaces of the cuffs transform the tissues in the vicinity of the blood vessels as well as the blood vessels. Even if the same pressure is applied to the cuff, the pressure in the blood vessel is not solely determined. Furthermore, the pressure measuring device mounted on the cuff is difficult to be accurately positioned above the blood vessel, e.g., the radial artery.

Another type of blood pulse wave measuring device comprises a pen-like holder and a pressure sensor mounted on the end of the holder. The pressure sensor is into contact with the patient's skin, e.g., the vicinity of the radial artery, and measures pulse wave according to the pulsation of the blood vessel.

Another type of blood pulse wave measuring device comprises a rubber glove and a strain gauge mounted on the finger sheath of the glove. The diagnostician wears the rubber glove and presses the strain gauge against the skin over the radial artery of the patient using with his finger, whereby the strain gauge detects blood pulse wave.

It is necessary for the diagnostician to hold the sensor above the radial artery of the patient when using such a blood vessel measuring device with the pen-like holder or rubber glove. However, since it is difficult for the diagnostician to continuously hold the sensor, mounted on the finger sheath or the pen end, above the radial artery, the sensor may move from the desirable position above the radial artery and may not measure accurately. If physiological status of organism is analyzed on the basis of inaccurate results obtained by such a measuring device, the analysis may contain some errors.

Accordingly, a pulse wave measuring device with an automatic positioner is proposed in JP-A-1-155828. In the device, while the sensor is moved across the line along the blood vessel, pulse wave is measured at a plurality of positions. The amplitude and other characteristics are analyzed over these positions, so that the best position directly above the blood vessel is detected. Then, the sensor is fixed at the best position to measure blood pulse wave.

However, the technique disclosed in JP-A-1-155828 needs a driver for moving the sensor, and devices for automatically determining the best measuring position. Therefore, the entire device should be enlarged.

It is therefore an object of the present invention to provide blood pulse wave measuring device and a pulsation measuring device, in which a pressure sensor or pulsation sensor can be positioned accurately on the measured subject, and the initial pressure given to the measured subject can be readily and desirably adjusted.

Another object of the present invention is to provide a pressure measuring device in which the energy loss can be reduced.

DISCLOSURE OF INVENTION

According to the present invention, a pulse wave measuring device for measuring pulse wave at a blood vessel of an organism, comprises: a vessel pressing portion being pressed against a skin over the blood vessel of the organism; a pulsation measuring sensor for measuring pulsation of the blood vessel pressed by the vessel pressing portion; two vessel-vicinity pressing portions being harder than the blood vessel of the organism and having distal ends, respectively, the distal ends being pressed against the skin of the organism at both sides of the vessel pressing portion; and adjusting means for adjusting an interval between the vessel-vicinity pressing portions.

In accordance with this pulse wave measuring device, since the interval between two vessel-vicinity pressing portions is adjusted by the adjusting means, the vessel-vicinity pressing portions can be positioned on softer skin parts at both sides of the measured blood vessel and press down the softer parts, whereby the pulsation measuring sensor can be readily positioned in relation to the blood vessel. In addition, since two vessel-vicinity pressing portions, which are harder than the blood vessel, press down the softer skin parts at both sides of the blood vessel, the initial pressure on the blood vessel given by the vessel pressing portion may be altered desirably. Since the interval between the vessel-vicinity pressing portions is adjusted, effect by skin tension can be constant, whereby the initial pressure may be altered more precisely.

In another aspect of the present invention, a pulse wave measuring device for measuring pulse wave at a blood vessel of an organism, comprises: a vessel pressing portion being pressed against a skin over the blood vessel of the organism; a pulsation measuring sensor for measuring pulsation of the blood vessel pressed by the vessel pressing portion; and two vessel-vicinity pressing portions being harder than the blood vessel of the organism and having distal ends, respectively, the distal ends being pressed against the skin of the organism at both sides of the vessel pressing portion, the vessel pressing portion being situated back from the distal ends of the vessel-vicinity pressing portions.

In accordance with this pulse wave measuring device, since the vessel pressing portion is situated back from the distal ends of the vessel-vicinity pressing portions, the blood vessel, which is harder than circumferential tissues, can be positioned between the vessel-vicinity pressing portions, whereby the vessel pressing portion can be readily positioned directly above the measured vessel. In addition, since two vessel-vicinity pressing portions, which are harder than the blood vessel, press down the softer skin parts at both sides of the blood vessel, the initial pressure on the blood vessel given by the vessel pressing portion may be altered desirably.

In another aspect of the present invention, a pulse wave measuring device for measuring pulse wave at a blood vessel of an organism, comprises: a beam supported by a support; a plurality of vessel pressing portions provided at the beam and arranged at intervals along a direction of the blood vessel of the organism, each of the vessel pressing portion being pressed against a skin over the blood vessel of the organism; a plurality of pressure sensors respectively corresponding to the vessel pressing portions, each of the pressure sensors outputting a pulse wave signal according to varying stress transmitted from the corresponding vessel pressing portion because of pulse wave of the blood vessel; and two vessel-vicinity pressing portions being harder than the blood vessel of the organism and having distal ends, respectively, the distal ends being pressed against the skin of the organism at both sides of the vessel pressing portions.

In accordance with this pulse wave measuring device, since two vessel-vicinity pressing portions, which are harder than the blood vessel, press down the softer skin parts at both sides of the blood vessel, the pulsation measuring sensor can be readily positioned in relation to the blood vessel and the initial pressure on the blood vessel given by the vessel pressing portion may be altered desirably. Furthermore, by means of the multiple number of pressure sensors, pulse waves transmitted respectively through the multiple number of vessel pressing portions can be measured, whereby the patient may be diagnosed in detail.

In another embodiment of the present invention, a pulse wave measuring device may comprise: a supporting member; a perpendicular sliding member which is supported by the supporting member and slidable perpendicularly in relation to the supporting member; measuring means situated at the perpendicular sliding member for measuring pulse wave at a blood vessel of an organism; and first and second toothed portions formed at mutual sliding faces of the supporting member and the perpendicular sliding member, respectively and meshed with each other.

In accordance with this pulse wave measuring device, the diagnostician manually handles the perpendicular sliding member, so that the measuring means is positioned in relation to the measured subject. Accordingly, although the entire device is of a simple construction without driving device and so on, accurate measurement may be achieved. In addition, after starting the measurement, the measuring means is prevented from being moved, so that accurate measurement may be achieved.

In another embodiment of the present invention, a pulse wave measuring device may comprise: a supporting member; a transverse sliding member which is supported by the supporting member and slidable transversely in relation to the supporting member; a perpendicular sliding member which is supported by the transverse sliding member and slidable perpendicularly in relation to the transverse sliding member; measuring means situated at the perpendicular sliding member for measuring pulse wave at a blood vessel of an organism; third and fourth toothed portions formed at mutual sliding faces of the supporting member and the transverse sliding member, respectively and meshed with each other; and fifth and sixth toothed portions formed at mutual sliding faces of the transverse sliding member and the perpendicular sliding member, respectively and meshed with each other.

In another embodiment of the present invention, a pulse wave measuring device may comprise: a supporting member; a perpendicular sliding member which is supported by the supporting member and slidable perpendicularly in relation to the supporting member; a transverse sliding member which is supported by the perpendicular sliding member and slidable transversely in relation to the perpendicular sliding member; measuring means situated at the transverse sliding member for measuring a pulse wave at a blood vessel of an organism; seventh and eighth toothed portions formed at mutual sliding faces of the supporting member and the perpendicular sliding member, respectively and meshed with each other; and ninth and tenth toothed portions formed at mutual sliding faces of the perpendicular sliding member and the transverse sliding member, respectively and meshed with each other.

In another embodiment of the present invention, a pulse wave measuring device may comprise: a supporting member; a transverse sliding member which is supported by the supporting member and slidable transversely in relation to the supporting member, a screw hole being formed perpendicularly at the transverse sliding member; eleventh and twelfth toothed portions formed at mutual sliding faces of the supporting member and the transverse sliding member, respectively and meshed with each other; a perpendicular sliding member which is screwed in the screw hole of the transverse sliding member and movable perpendicularly to the transverse sliding member by rotation; and measuring means situated at the perpendicular sliding member for measuring pulse wave at a blood vessel of an organism.

According to the present invention, a pulsation measuring device for measuring pulsation at a measured subject of a measured thing, comprises: a subject pressing portion being pressed against a covering over the measured subject of the measured thing; a pulsation measuring sensor for measuring pulsation of the measured subject pressed by the subject pressing portion; two subject-vicinity pressing portions being harder than the measured subject of the measured thing and having distal ends, respectively, the distal ends being pressed against the covering of the measured thing at both sides of the subject pressing portion; and adjusting means for adjusting an interval between the subject-vicinity pressing portions.

In another aspect of the present invention, a pulsation measuring device for measuring pulsation at a measured subject of a measured thing, comprises: a subject pressing portion being pressed against a covering over the measured subject of the measured thing; a pulsation measuring sensor for measuring pulsation of the measured subject pressed by the subject pressing portion; and two subject-vicinity pressing portions being harder than the measured subject of the measured thing and having distal ends, respectively, the distal ends being pressed against the covering of the measured thing at both sides of the subject pressing portion, the subject pressing portion being situated back from the distal ends of the subject-vicinity pressing portions.

In another aspect of the present invention, a pulsation measuring device for measuring pulsation at a measured subject of a measured thing, comprises: a beam supported by a support; a plurality of subject pressing portions provided at the beam and arranged at intervals along a direction of the measured subject of the measured thing, each of the subject pressing portion being pressed against a covering over the measured subject of the measured thing; a plurality of pressure sensors respectively corresponding to the subject pressing portions, each of the pressure sensors outputting a pulsation signal according to varying stress transmitted from the corresponding subject pressing portion because of the pulsation of the measured subject; and two subject-vicinity pressing portions being harder than the measured subject of the measured thing and having distal ends, respectively, the distal ends being pressed against the covering of the measured thing at both sides of the subject pressing portions.

In another embodiment of the present invention, a pulsation measuring device may comprise: a supporting member; a perpendicular sliding member which is supported by the supporting member and slidable perpendicularly in relation to the supporting member; measuring means situated at the perpendicular sliding member for measuring pulsation at a measured subject of a measured thing; and first and second toothed portions formed at mutual sliding faces of the supporting member and the perpendicular sliding member, respectively and meshed with each other.

In another embodiment of the present invention, pulsation measuring device may comprise: a supporting member; a transverse sliding member which is supported by the supporting member and slidable transversely in relation to the supporting member; a perpendicular sliding member which is supported by the transverse sliding member and slidable perpendicularly in relation to the transverse sliding member; measuring means situated at the perpendicular sliding member for measuring pulsation at a measured subject of a measured thing; third and fourth toothed portions formed at mutual sliding faces of the supporting member and the transverse sliding member, respectively and meshed with each other; and fifth and sixth toothed portions formed at mutual sliding faces of the transverse sliding member and the perpendicular sliding member, respectively and meshed with each other.

In another embodiment of the present invention, a pulsation measuring device may comprise: a supporting member; a perpendicular sliding member which is supported by the supporting member and slidable perpendicularly in relation to the supporting member; a transverse sliding member which is supported by the perpendicular sliding member and slidable transversely in relation to the perpendicular sliding member; measuring means situated at the transverse sliding member for measuring pulsation at a measured subject of a measured thing; seventh and eighth toothed portions formed at mutual sliding faces of the supporting member and the perpendicular sliding member, respectively and meshed with each other; and ninth and tenth toothed portions formed at mutual sliding faces of the perpendicular sliding member and the transverse sliding member, respectively and meshed with each other.

In another embodiment of the present invention, a pulsation measuring device may comprise: a supporting member; a transverse sliding member which is supported by the supporting member and slidable transversely in relation to the supporting member, a screw hole being formed perpendicularly at the transverse sliding member; eleventh and twelfth toothed portions formed at mutual sliding faces of the supporting member and the transverse sliding member, respectively and meshed with each other; a perpendicular sliding member which is screwed in the screw hole of the transverse sliding member and movable perpendicularly to the transverse sliding member by rotation; and measuring means situated at the perpendicular sliding member for measuring pulsation at a measured subject of a measured thing.

According to another aspect of the present invention, a pressure measuring device comprises: a beam having at least one proximal portion supported by a support; a subject pressing portion provided at the beam and pressed against a measured subject; and a piezoelectric element mounted on the beam for outputting an electric signal according to varying stress transmitted from the subject pressing portion, the beam including a thinner portion formed between the proximal portion and the subject pressing portion, the thinner portion being thinner than other portions of the beam, the piezoelectric element being longer than the thinner portion and mounted on the thinner portion entirely and on another portion partially, which is closer to the proximal portion or subject pressing portion than the thinner portion.

In this pressure measuring device, since the piezoelectric element is longer than the thinner portion to be mounted on another portion in addition to the thinner portion, strain energy accumulated in the piezoelectric element can be enhanced. Therefore, the current generated by the piezoelectric element can be increased in comparison with prior art.

In another aspect of the present invention, a pressure measuring device comprises: a beam having at least one proximal portion supported by a support; a subject pressing portion provided at the beam and pressed against a measured subject; and a piezoelectric element mounted on the beam for outputting an electric signal according to varying stress transmitted from the subject pressing portion, an area of cross section of the thinner portion of the beam, on which the piezoelectric element is mounted, being equal to or less than 60% of an area of total cross section of the thinner portion and the piezoelectric element mounted thereon.

In accordance with this pressure measuring device, since the area of cross section of the beam is not large in relation to that of the piezoelectric element mounted thereon, strain energy accumulated in the beam is diminished and strain energy in the piezoelectric element is relatively enhanced. Therefore, electric energy converted from the strain energy by the piezoelectric element can be relatively increased, whereby amplitude of the output signal from the piezoelectric element can be enlarged.

BRIEF DESCRIPTION OF DRAWINGS

Various embodiments will be described below with reference to the accompanying drawings. In the accompanying drawings.

BEST MODE FOR CARRYING OUT INVENTION

Figure 1:
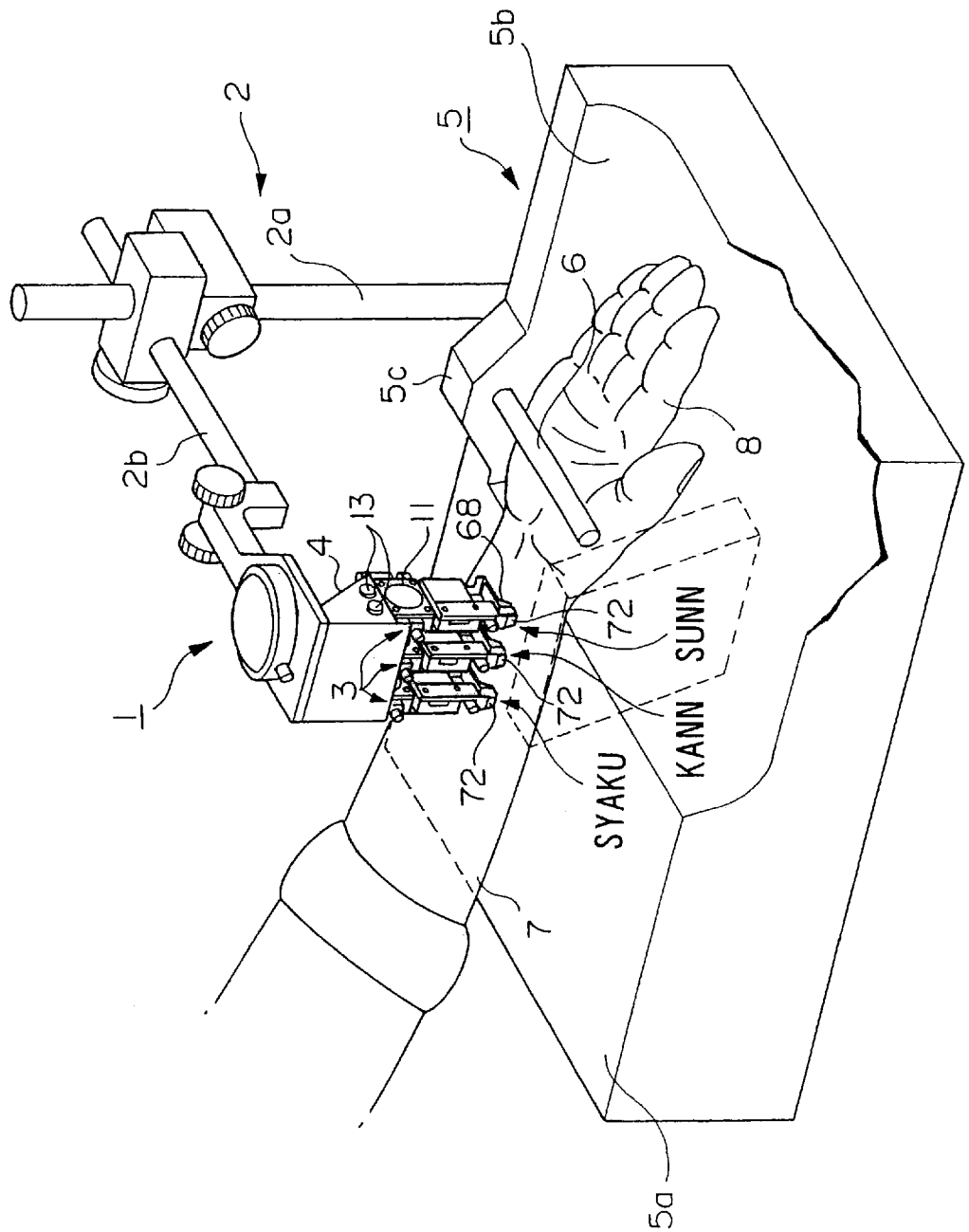
FIG. 1 is a perspective view showing a pulse wave measuring device according to a first embodiment of the present invention.

1. First Embodiment
1-1. Structure of Pulse Wave Measuring Device of First Embodiment As shown in FIG. 1, a pulse wave measuring device 1 according to a first embodiment of the present invention comprises a stand 2 placed on a flat plane and three pulse wave measuring units 3, which are of the same type as one another, supported by the stand 2. The stand 2 includes a vertically standing shaft 2a, and an arm 2b connected to the shaft 2a. A bracket 4 is arranged at the distal end of the arm 2b.

The height of the proximal end of the arm 2b can be adjusted in relation to the shaft 2a. The arm 2b is rotatable about the shaft 2a, so that the direction of the arm 2b in a horizontal plane can be adjusted. In addition, the arm 2b can be swiveled in a vertical plane, and the direction of the arm 2b in the vertical plane can be adjusted. These adjusting mechanisms are known, so that the description thereof is omitted. By the above-mentioned adjustment of the stand 2, the position of the bracket 4 may be adjusted. However, other mounting means may be adapted instead of the stand 2 as long as the position of the bracket 4 can be adjusted.

An arm support 5 is utilized for the pulse wave measuring device 1. The arm support 5 is of a substantially rectangular block shape having a planar upper surface 5a. An upwardly opening hollow 5b is formed at the arm support 5 while an upwardly projecting wall 5c is formed in the vicinity of the hollow 5b. A cylindrical rod 6 is mounted on the projecting wall 5c, so as to extending over the hollow 5b and parallel to the upper surface 5a.

A human patient's arm (measured thing) 7 is placed on the upper surface 5a of the arm support 5 in such a manner that the patient's hand 8 is situated below the rod 6 and the palm is oriented upward. In this condition, the hand 8 may be inclined slightly downward from the wrist so as to be positioned within the hollow 5b. Accordingly, as long as the patient does not move the arm 7 intentionally, the arm 7 is stabled at the illustrated position. Above the arm 7 placed on the upper surface 5a, three pulse wave measuring units (pulsation detecting devices) 3 are arranged by adjusting the stand 2. The pulse wave measuring units 3 measures the pulse waves at three portions called "Sunn", "kann", and "Syaku" in Oriental medicine, respectively.

FIGS. 2A, 2B, 3, and 4 show one of the pulse wave measuring unit 3. The single pulse wave measuring unit 3 comprises a supporting member 10 and a pressure measuring device 80 supported in a cantilever manner by the supporting member 10. As will be described later, two pressing legs (vessel-vicinity pressing portions or subject-vicinity pressing portions) 68 and 72 are formed at the supporting member 10. The pressing legs 68 and 72 are oriented toward and are pressed against the patient's arm 7.

The supporting member 10 comprises a mounting plate 11 which is a substantially rectangular planar plate. As shown in FIG. 1, the mounting plate 11 is secured to the bracket 4 by screws 13, and the supporting member 10 is arranged in a vertical plane. The mounting plates 11 of three pulse wave measuring units 3 are parallel to one another. As illustrated in FIGS. 2A, 2B, 3, and 4, a pair of through-holes 12, through which the screws 13 are inserted, are formed at the upper portion of the mounting plate 11.

At the lower portion of the mounting plate 11, a circular penetrating opening 14 is formed. Four screws 15 arranged around the opening 14 secure a first perpendicular sliding plate 16 to the mounting plate 11. The first perpendicular sliding plate 16, which is a substantially rectangular planar plate, is provided with a perpendicular guidance groove 17 at the side which is opposite to the mounting plate 11.

At the side, which is opposite to the mounting plate 11, of the first perpendicular sliding plate 16, a second perpendicular sliding plate 18 is arranged in a manner that the second sliding plate 18 is slidable in relation to the first slidable plate 16. The second perpendicular sliding plate 18 is also a substantially rectangular planar plate. A pair of parallel rails 19 and 20 are fixed at the side, facing to the first slidable plate 16, of the second sliding plate 18. The rails 19 and 20 are put into the perpendicular guidance groove 17 of the first perpendicular sliding plate 16, so that the second perpendicular sliding plate 18 is slidable along the vertical or perpendicular direction in relation to the first perpendicular slidable plate 16. A mechanism is provided for preventing the first and second sliding plates 16 and 18 from being separated from each other (not shown).

Pins 21 and 22 are arranged in the space between the rails 19 and 20. The upper pin 21 is fixed to the second slidable plate 18 while the lower pin 22 is fixed to the first slidable plate 16. Hooks formed at both ends of a coil spring 23 are hung on the pins 21 and 22, respectively. Therefore, the second perpendicular slidable plate 18 is always pulled downwardly.

Figures 2A, 2B:
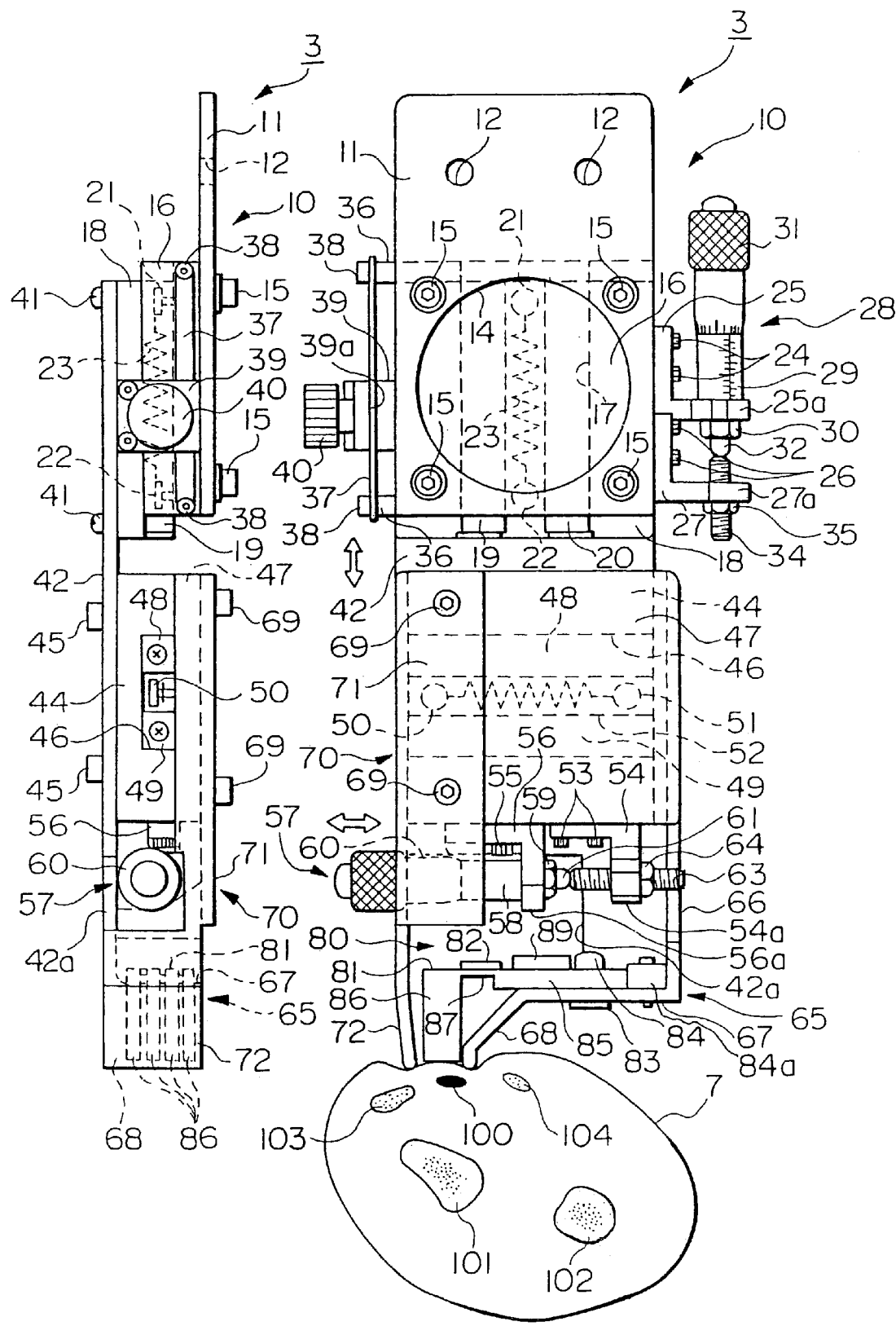
FIG. 2A is a front view showing one of pulse wave measuring units of the pulse wave measuring device in FIG. 1.
FIG. 2B is a left side view of FIG. 2A.
Figure 3:
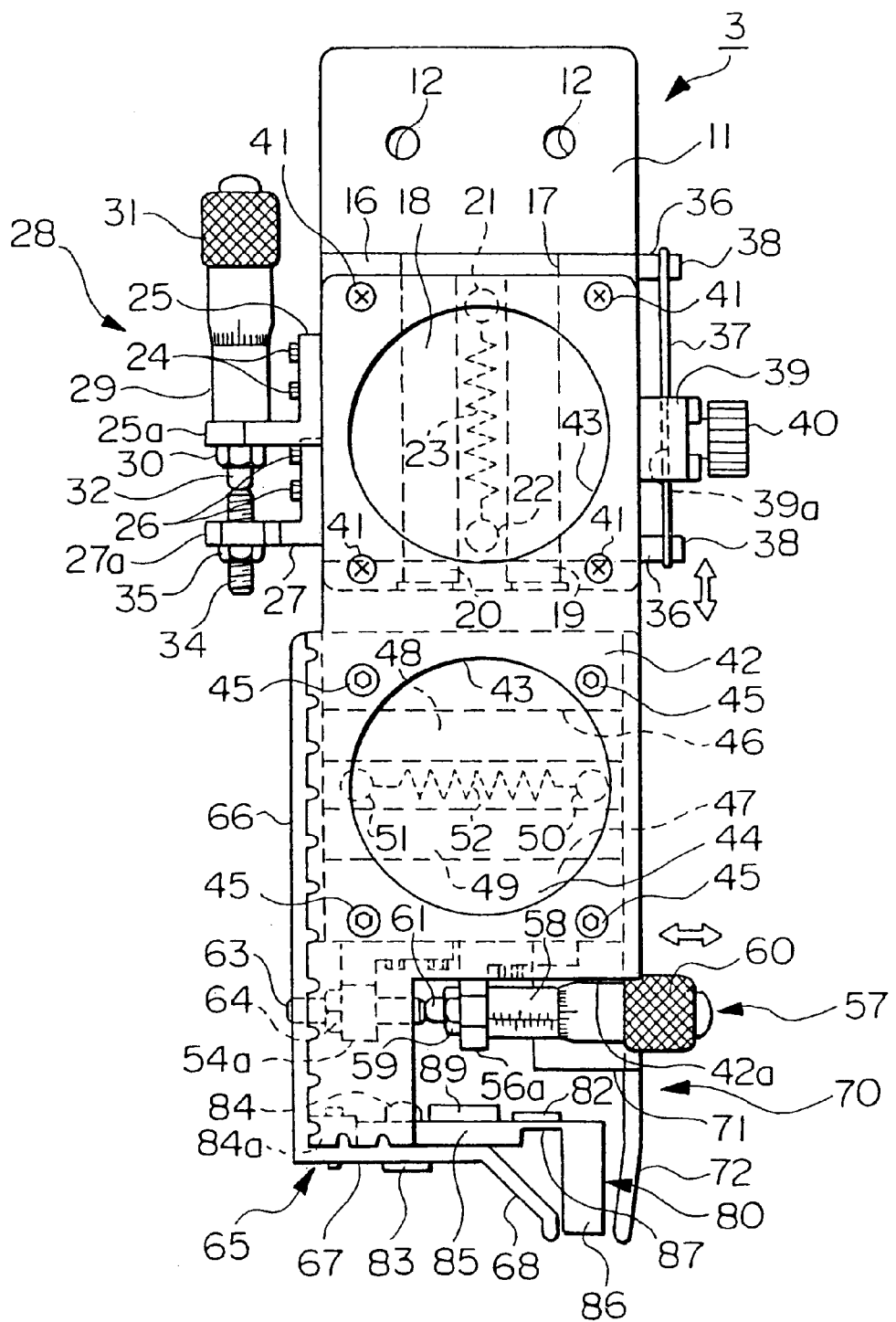
FIG. 3 is a rear view showing the pulse wave measuring unit in FIG. 2A.
Figure 4:
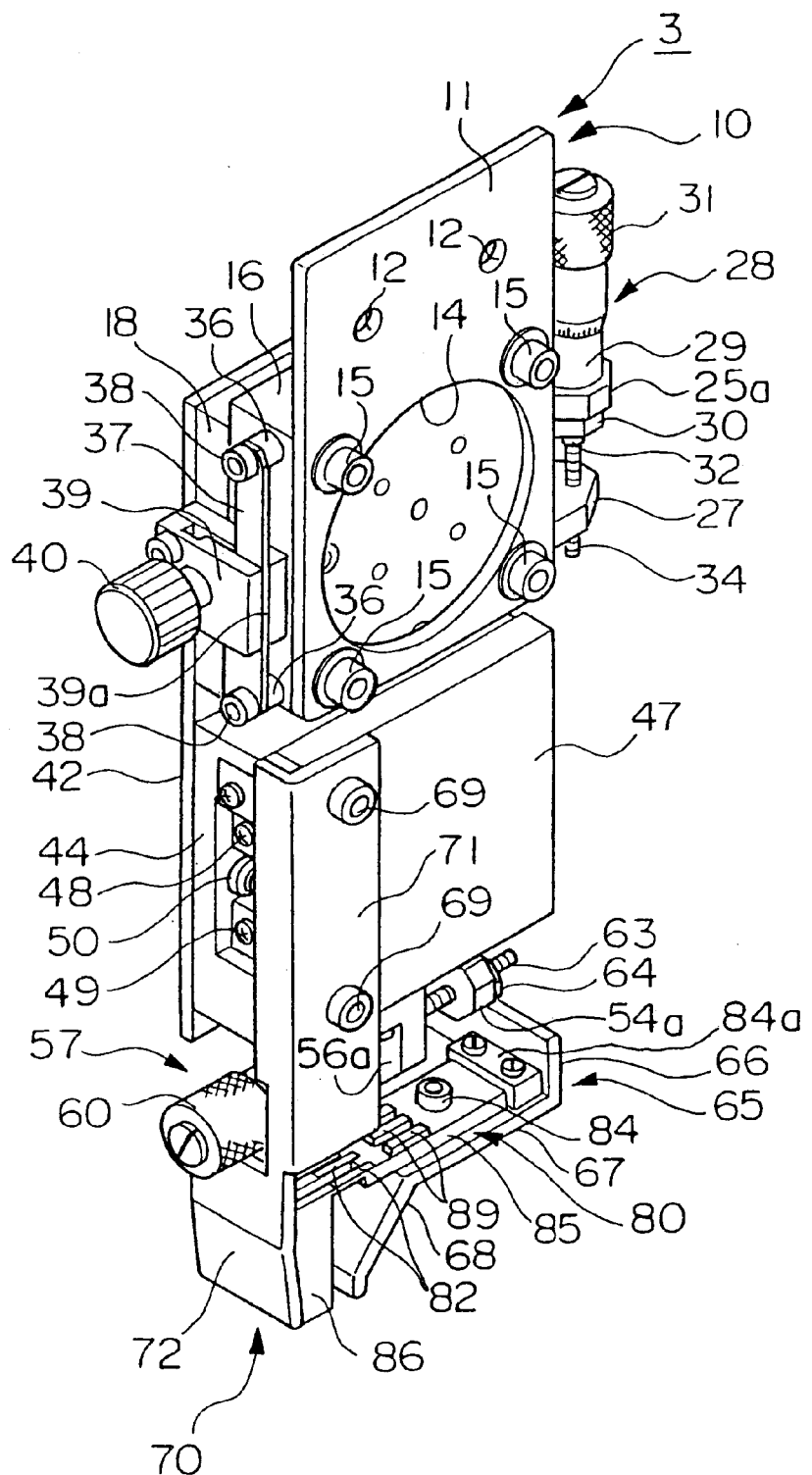
FIG. 4 is a perspective view showing the pulse wave measuring unit in FIG. 2A.

As shown in FIGS. 2A and 3, an L-shaped bracket 25 is secured to the second perpendicular sliding plate 18 by screws 24 while another L-shaped bracket 27 is secured to the first perpendicular sliding plate 16 by screws 26. The bent distal end 25a of the L-shaped bracket 25 projects frontward in FIG. 2A while the bent distal end 27a of the bracket 27 projects rearward in FIG. 2A, so that the ends 25a and 27a overlap with each other in a vertical line.

The sleeve 29 of a micrometer head 28 is fixed to the distal end 25a of the L-shaped bracket 25 by a nut 30. The micrometer head 28 is of a known configuration comprising the sleeve 29, a thimble 31, and a spindle 32.

On the other hand, a headless screw 34 is screwed in the distal end 27a of the L-shaped bracket 27 and is fixed by a nut 35 temporarily. The spindle 32 of the micrometer head 28 and the headless screw 34 are aligned coaxially. Since the coil spring 23 pulls the first perpendicular sliding plate 18 downward, the end face of the spindle 32 is always in contact with the upper end face of the screw 34.

Figure 7:
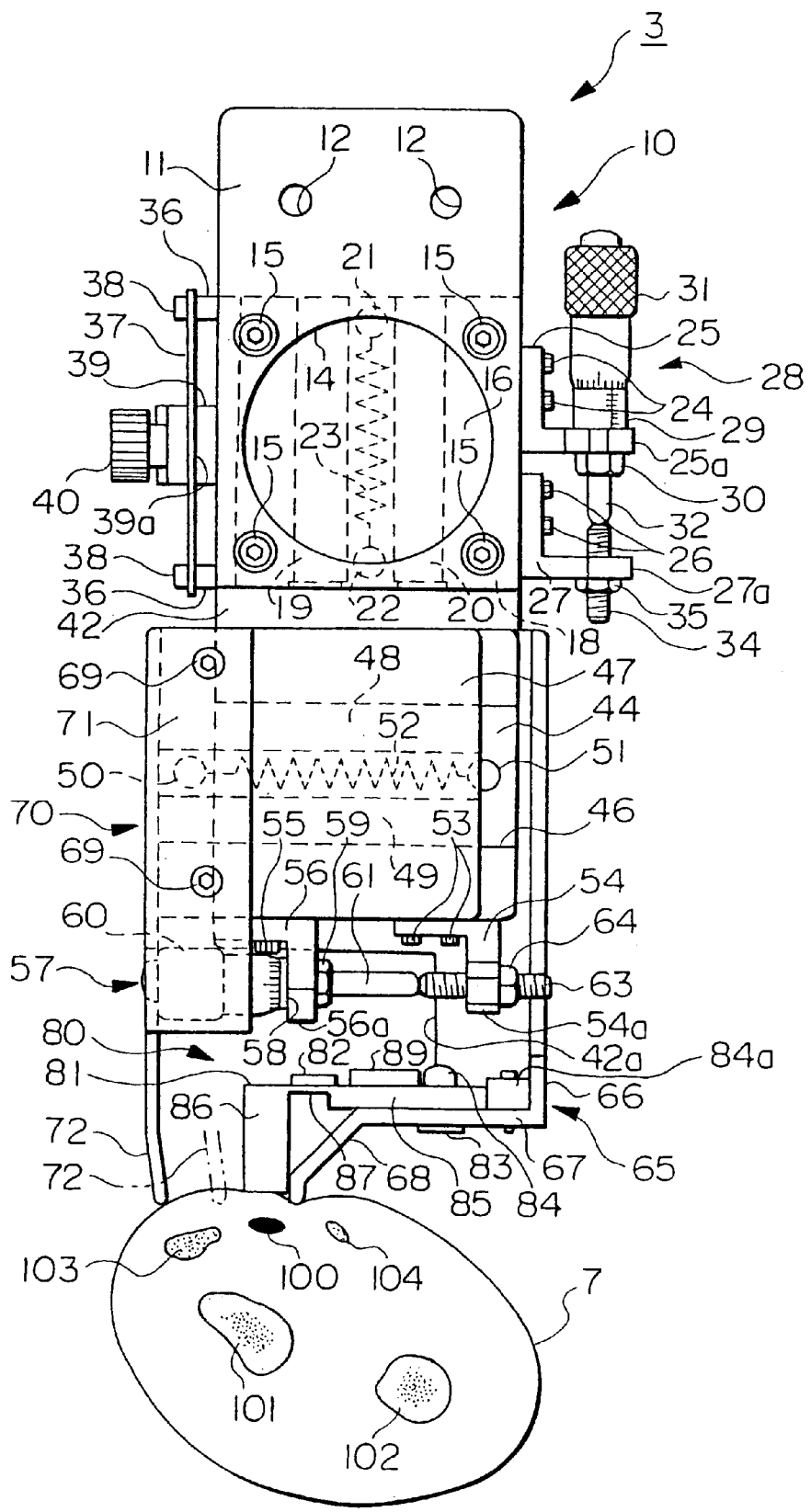
FIG. 7 is a front view showing the pulse wave measuring unit in FIG. 2A when pressing legs (vessel vicinity pressing portions) thereof are in contact with the patient's arm at a small pressure.

With such a structure, when the thimble 31 of the micrometer head 28 is revolved about the axis thereof, the spindle 32 extends or contracts. When the spindle 32 extends, the second sliding plate 18 is raised up overcoming the force of the coil spring 23 since the headless screw 34 is secured to the fixed first sliding plate 16. Conversely, when the spindle 32 contracts, the second sliding plate 18 is lowered in relation to the first sliding plate 16 by the force of the coil spring 23. FIG. 7 shows the second sliding plate 18 raised in comparison with the status shown in FIG. 2A. The displacement of the second sliding plate 18 can be measured using with the dials of the thimble 31 and sleeve 29 of the micrometer head 28 in a known manner.

Two protruding pins 36 are attached to the side surface, which is opposite to the micrometer head 28, of the first sliding plate 16. A narrow plate 37 bridging between the pins 36 are fixed to the pins 36 by screws 38. The narrow plate 37 is held in the vertical groove 39a in a holding block 39 of a rectangular block shape that is attached to the second sliding plate 18. A fastening screw 40 is screwed in the holding block 39, and can tightly fasten the narrow plate 37 in the vertical groove 39a when the screw 40 is revolved. In summary, after the height of the second sliding plate 18 is adjusted by handling the micrometer head 28, the height is maintained by fastening the screw 40. Before the height of the second sliding plate 18 is adjusted by handling the micrometer head 28, it is necessary to loosen the screw 40 in order that the narrow plate 37 be freed from the holding block 39.

As shown in FIGS. 2B and 3, a connecting plate 42 is secured by screws 41 to the side, which is opposite to the first sliding plate 16, of the second sliding plate 18. The connecting plate is of a length in the vertical direction greater than the double of the length of the second sliding plate 18. Circular penetrating openings 43 are formed at upper and lower positions of the connecting plate 42.

A first horizontal or transverse sliding plate 44, which is of a substantially rectangular planar shape, is fixed to the connecting plate 42 by the screws 45. A horizontally extending guidance groove 46 is formed at the side, which is opposite to the connecting plate 42, of the first transverse sliding plate 44.

At the side, which is opposite to the connecting plate 42, of the first transverse sliding plate 44, a second horizontal or transverse sliding plate 47 is arranged in a manner that the second transverse sliding plate 47 is slidable in relation to the first transverse slidable plate 44. The second transverse sliding plate 47 is also a substantially rectangular planar plate. A pair of parallel rails 48 and 49 are fixed at the side, facing to the first transverse slidable plate 44, of the second transverse sliding plate 47. The rails 48 and 49 are put into the horizontal guidance groove 46 of the first transverse sliding plate 44, so that the second transverse sliding plate 47 is slidable along the transverse direction in relation to the first transverse slidable plate 44. A mechanism is provided for preventing the first and second sliding plate 44 and 47 from being separated from each other (not shown).

Pins 50 and 51 are arranged in the space between the rails 48 and 49. The pin 50 is fixed to the second slidable plate 47 while the other pin 51 is fixed to the first slidable plate 44. Hooks formed at both ends of a coil spring 52 are hung on the pins 50 and 51, respectively, Therefore, the second transverse slidable plate 47 is always pulled leftwardly in FIG. 2A.

As shown in FIGS. 2A and 3, an L-shaped bracket 54 is secured to the first transverse sliding plate 44 by screws 53 while another L-shaped bracket 56 is secured to the second transverse sliding plate 47 by screws 55. The bent distal end 54a of the L-shaped bracket 54 projects frontward in FIG. 2A while the bent distal end 56a of the bracket 56 projects rearward in FIG. 2A, so that the ends 54a and 56a overlap with each other in a horizontal line.

The sleeve 58 of a micrometer head (adjusting means) 57 is fixed to the distal end 56a of the L-shaped bracket 56 by a nut 59. The micrometer head 57 comprises the sleeve 58, a thimble 60, and a spindle 61, as similar to the micrometer head 28.

Figure 5:
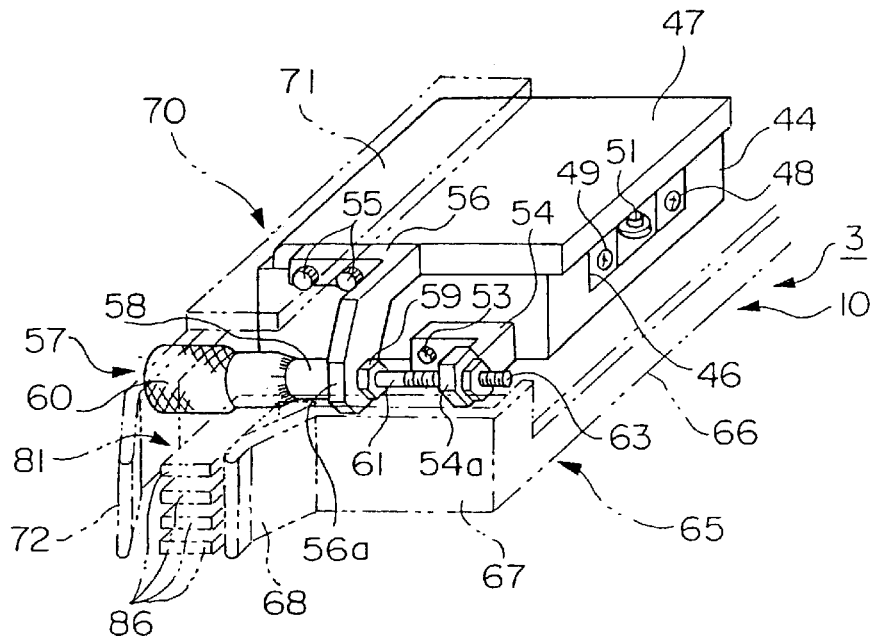
FIG. 5 is a bottom view showing the pulse wave measuring unit in FIG. 2A.

On the other hand, a headless screw 63 is screwed in the distal end 54a of the L-shaped bracket 54 and is fixed by a nut 64 temporarily. The spindle 61 of the micrometer head 57 and the headless screw 63 are aligned coaxially. Since the coil spring 52 pulls the second transverse sliding plate 47 leftward in FIG. 2A, the end face of the spindle 61 is always in contact with the end face of the screw 63. To clarify the structure, the pulse wave measuring unit 3 viewed from a lower position is shown in FIG. 5.

With such a structure, when the thimble 60 of the micrometer head 57 is revolved about the axis thereof, the spindle 61 extends or contracts. When the spindle 61 extends, the second sliding plate 47 is moved rightward in FIG. 2A overcoming the force of the coil spring 52. Conversely, when the spindle 61 contracts, the second sliding plate 47 is moved leftward in FIG. 2A in relation to the first sliding plate 44 by the force of the coil spring 52. FIG. 7 shows the second sliding plate 47 is moved leftward in comparison with the status shown in FIG. 2A. The displacement of the second sliding plate 47 can be measured using with the dials of the thimble 60 and sleeve 58 of the micrometer head 57.

A rectangular notch 42a is formed at the lower end of the connecting plate 42, so that the dials of the micrometer head 57 can be seen through the notch 42a. As shown in FIG. 2A, a bent first pressing plate 65 is secured to the right side face and the lower end face of the connecting plate 42. The first pressing plate 65 comprises a vertical portion 66 secured to the right side face of the connecting plate 42, a horizontal portion bent perpendicularly from the lower end of the vertical portion 66, and a first pressing leg 68 bent obliquely and downwardly from the horizontal portion 67. As shown in FIG. 3, the horizontal portion 67 is secured to the lower end face of the connecting plate 42 while the lower end portion of the first pressing legs 68 is bent and oriented downwardly.

In addition, a second pressing plate 70 is secured to the second transverse sliding plate 47 by screws 69. The second pressing plate 70 comprises a planar mounting portion 71 secured to a front surface of the second transverse sliding plate 47 in FIG. 2A, and a planar second pressing leg 72 bent perpendicularly from the mounting portion 71. The lower portion of the second pressing leg 72 is of a width greater than that of the upper portion, and faces to the first pressing leg 68. The lower end portion of the second pressing leg 68 is bent obliquely and downwardly. Since the second transverse sliding plate 47 is moved transverse in relation to the first transverse sliding plate 44 as described above, the interval between the pressing legs 68 and 72 is adjusted.

As shown in FIG. 2A, the pressing legs 68 and 72 may be into contact with the skin of the patient's arm 7, especially, both side positions of the radial artery (measured subject) 100. In FIG. 2A, a cross section of the arm 7 is shown for clearly indicating the radius 101, ulna 102, brachioradialis tendon 103, and flexor carpi radialis tendon 104. The first leg 68 presses the softer or more elastic part between the radial artery 100 and the flexor carpi radial is tendon 104 while the second leg 72 presses the softer or more elastic part between the radial artery 100 and the brachioradialis tendon 103. In the organism's superficial portion, since the vicinity of blood vessels and tendons has less elasticity and other parts have greater elasticity, the pressing legs 68 and 72 press down the softer parts.

The structural elements of the supporting member 10, i.e., the mounting plate 11, the first and second perpendicular sliding plates 16 and 18, the connecting plate 42, the first and second transverse sliding plates 44 and 47, and the first and second pressing plates 65 and 70 are manufactured of a metal. However, these elements may be made of another material, such as hard plastics, as long as the material has hardness greater than that of the blood vessel or measured subject (radial artery in this embodiment).

The horizontal portion 67 of the first pressing plate 65 supports a pressure measuring device 80 comprising a beam 81 supported by the horizontal portion 67 in a cantilever manner, and piezoelectric elements (pulsation measuring sensors or pressure sensors) 82 adhered on the beam 81. The beam 81 is of a substantially L-shaped configuration comprising a planar supported portion 85, which is a proximal portion secured to the horizontal portion 67; and a contact portion (vessel pressing portion or measured subject pressing portion) 86, which is perpendicularly bent from the supported portion 85. The center of the supported portion of the beam 81 is affixed to the horizontal portion 67 by a bolt 83 and nut 84 while the end of the supported portion is pinched between a jaw plate 84a and the horizontal portion 67, which are secured to each other.

The contact portion 86 is situated in the space between the first and second legs 68 and 72. In other words, the pressing legs 68 and 72 are arranged at both sides of the contact portion 86. The distal end of the contact portion 86 is oriented downward and may be into contact with the skin over the radial artery 100 of the patient's arm 7. The distal end of the contact portion 86 is upper than the distal ends of the pressing legs 68 and 72. That is, the distal end of the contact portion 86 is situated back from the distal ends of the pressing legs 68 and 72. When the beam 81 is not stressed, the distal end of the contact portion 86 is preferably 0.5 to 2 mm, more preferably 0.9 to 1.1 mm upper than the distal ends of the pressing legs 68 and 72.

Figure 6B:
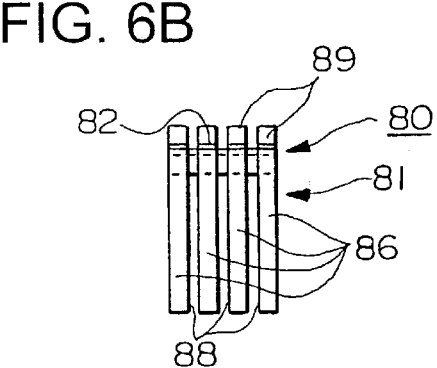
FIG. 6B is a left side view of FIG. 6A.
Figure 6A:
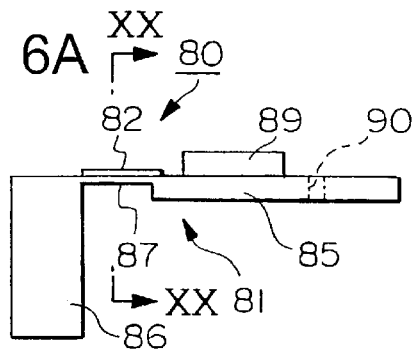
FIG. 6A is a front view showing a pressure measuring device of the pulse wave measuring unit in FIG. 2A.
Figure 6C:
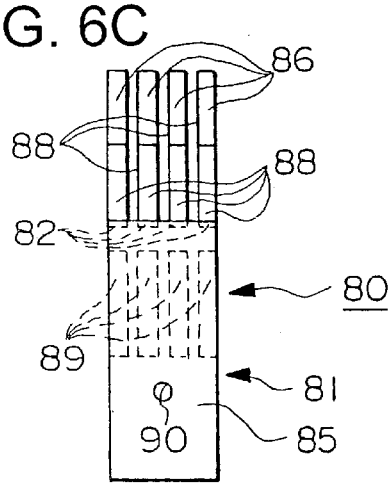
FIG. 6C is a bottom view of FIG. 6A.

As shown in FIG. 6A, the distal end portion of the supported portion 85 of the beam 81 is thinner than the other portions. This portion will be called thinner portion 87. As shown in FIGS. 6B and 6C, three parallel separating grooves 88 are formed from the thinner portion 87 and the contact portion 86. Therefore, each of the thinner portion 87 and the contact portion 86 is divided into four parts. Four piezoelectric elements 82 are adhered to the upper surfaces of four thinner portions 87, respectively. More exactly, each piezoelectric element 82 is longer than the thinner portion 87 along the longitudinal direction of the beam 81 and is adhered to the corresponding thinner portion 87 entirely and to the supported portion 85 partially. In addition, a through-hole 90 for inserting the above-mentioned bolt 83 is illustrated in FIGS. 6A and 6C.

With such a structure, the stress on four contact portions 86 varies according to pulsation of the radial artery 100. The varying stress is transmitted to each piezoelectric element 82 via the corresponding thinner portion 87. Each piezoelectric element 82 outputs a pulse wave signal (pulsation signal) which is the voltage varying according to the stress variation. The supported portion 85 of the beam 81 is provided with four amplification units 89. Pulse wave signal from each of the piezoelectric elements 82 is supplied to corresponding amplification unit 89 to be amplified, and the amplified signal is outputted from the unit 89.

As will be understood, the beam 81 of each pulse wave measuring unit 3 is provided with four contact portions 86, which are aligned in a row at an interval along the radial artery 100. Consequently, each pulse wave measuring unit 2 measures pulse waves at four points of the patient's arm 7. Since the pulse wave measuring device 1 has three pulse wave measuring units 3, the entire pulse wave measuring device 1 measures 12 points.

Figure 18:
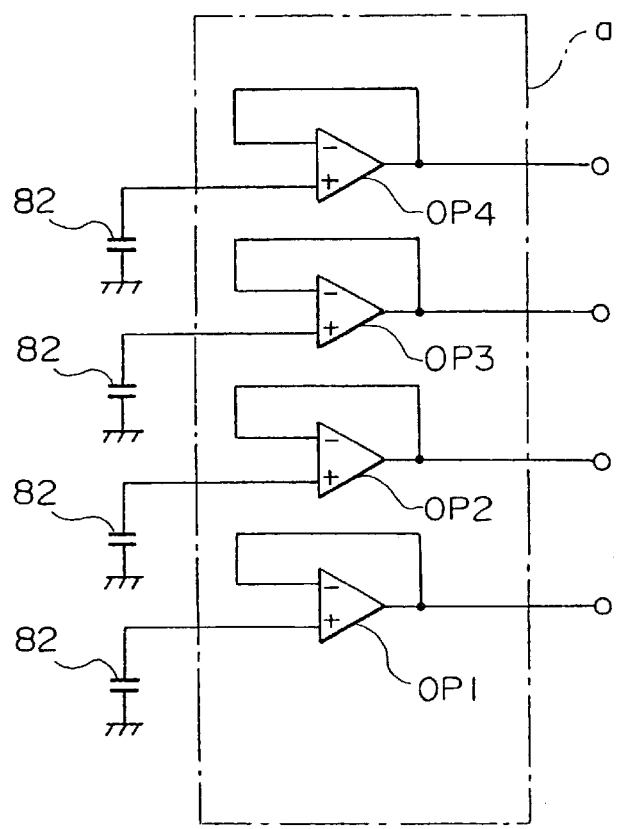
FIG. 18 is a diagram showing an output circuit, in which the output signals from the pressure sensors of the pulse wave measuring unit are amplified, of the first embodiment.
Figure 19:
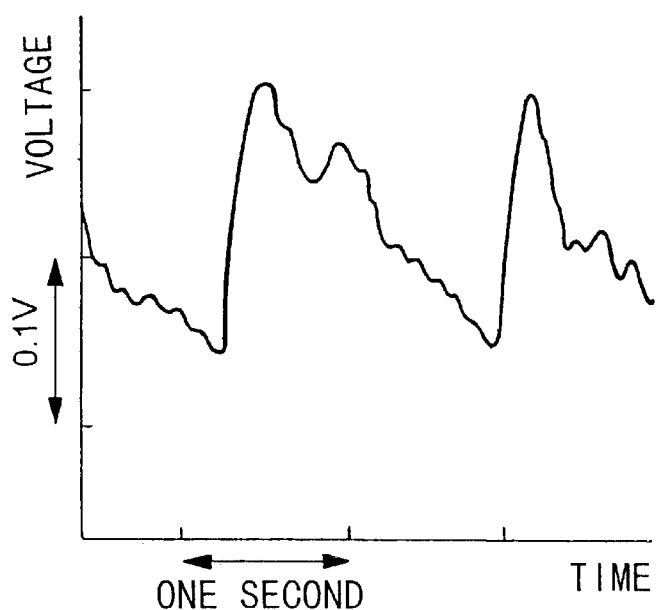
FIG. 19 is a graph showing a pulse waveform amplified by the output circuit shown in FIG. 18.

FIG. 18 shows an output circuit "a" in which the output signals from the piezoelectric elements 82 are amplified. The output circuit a is constituted of four operational amplifiers OP1 to OP4, which are respectively contained in the amplification units 89. With respect to each of the op-amps OP1 to OP4, the negative input terminal and the output terminal is connected, so that each op-amp functions as a voltage follower. The piezoelectric elements 82 are connected with the positive input terminals of the op-amps OP1 to OP4 and with the earth. Input impedance of the op-amps OP1 to OP4 is between $10^8$ ohms and $10^{12}$ ohms. Such high input impedance can be realized by the op-amps since they are MOSFETs and the like. If other op-amps with only low input impedance are used, the output signals of the op-amps are not analyzed since the current generated by the piezoelectric element 82 is weak. However, the op-amps OP1 to OP4 have high input impedance, the output signals can be analyzed. In an experiment, the amplitude of voltage at the output terminal of each of the op-amps OP1 to OP4 was about 0.15 volts as shown in FIG. 19.

The output signals from the op-amps OP1 to OP4 are provided to an outside analog-to-digital converter (not shown), and converted to digital signals. The digital signals are provided to a computer (not shown). The output circuit a shown in Fig, 18 is provided in the beam 81 for a single pulse wave measuring unit 3. Therefore, three output circuits a are provided for three pulse wave measuring units 3 in the entire device 1. The A/D converter has 12 channels for the op-amps OP1 to OP4 of three measuring units 3 and converts the signals through 12 channels. The computer operates on the basis of a diagnostic program, referring to the signals provided through 12 channels, so as to diagnose the patient's physiological condition.

In the above-described pressure measuring device 80, since the piezoelectric elements 82 are fixed at the thinner portions 87 of the beam 81, the transformation occurred on the piezoelectric elements 82 according to the stress variation is larger than the transformation when they are fixed at other portions. Therefore, the strain exerted on the piezoelectric elements 82 is large, so that the measurement accuracy can be enhanced. Each of the piezoelectric elements 82 is longer than the thinner portion 87 along the longitudinal direction of the beam 81 and is adhered to the corresponding thinner portion 87 entirely and to the supported portion 85 partially. Since the piezoelectric elements 82 is long and partially adhered on the supported portion 85, the strain energy stored in each piezoelectric element 82 is large when the beam 81 is stressed.

In a typical conventional pressure measuring device with cantilever, a piezoelectric element is adhered only to the vicinity of the distal end of the cantilever (vicinity of the contact portions 86, e.g., thinner portions 87 in the embodiment) since the curvature is the largest at distal end. However, the piezoelectric element in the vicinity of the end should be small in size. Therefore, less strain energy is stored therein, and flown is an extremely weak current. Furthermore, although a piezoelectric element can output a high voltage, it generates less current. Accordingly, the output voltage (signal) is difficult to be detected and analyzed by the prior art.

In contrast, by virtue of the above-described pressure measuring device 80, since much strain energy can be accumulated in the piezoelectric element 82, the current generated by the piezoelectric element 82 is larger than that of conventional device. Therefore, the amplitude of the output signal may be enlarged. The above-described output circuit with high input impedance can further improve the advantage.

In the illustrated embodiment, the piezoelectric element 82 is adhered, along the longitudinal direction of the beam 81, to the corresponding thinner portion 87 entirely and to the supported portion 85 partially. However, in a variant, the piezoelectric element 82 may be adhered to the corresponding thinner portion 87 entirely and to the contact portions 86 partially. In another variant, the piezoelectric element 82 may be adhered to the corresponding thinner portion 87 entirely, to the supported portions 85 partially, and to the contact portion 86 partially.

In order to accumulate much strain energy, it is preferable that the area of the piezoelectric element 82 is large. However, if the area of piezoelectric element 82 is large, the electrostatic capacity will be large, thereby lowering the measurement accuracy. Accordingly, it is preferable that the area of the piezoelectric element 82 is between 130 and 150% of that of the corresponding thinner portion 87. Namely, the extra area of the piezoelectric element 82 protruding outside from the corresponding thinner portion 87 is preferably between 30 and 50% of the area of the corresponding thinner portion 87.

Figure 20:
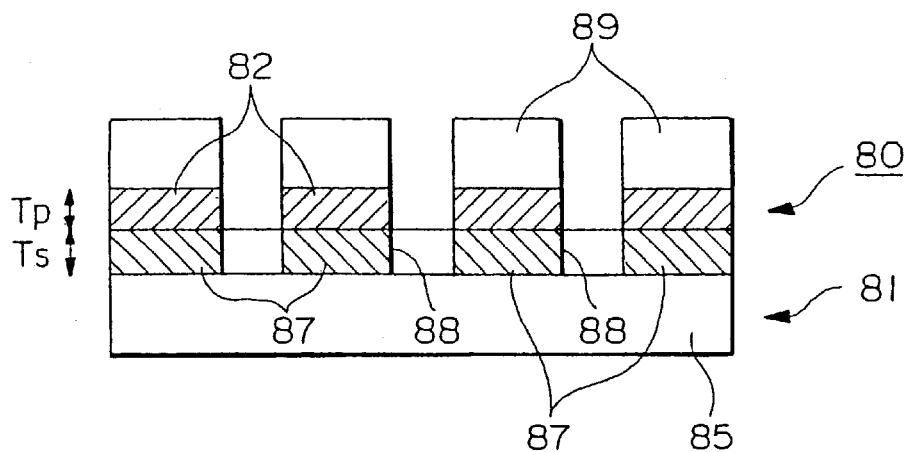
FIG. 20 is a cross sectional view showing the pressure measuring device taken along line XX—XX in FIG. 6A.

FIG. 20 is a cross section of the pressure measuring device 80 taken along line XX—XX in FIG. 6A. As shown in FIG. 20, the thickness Ts of the thinner portions 87 of the beam 81 is substantially the same as the thickness Tp of the piezoelectric elements 82. The reason will be explained below.

Figure 21:
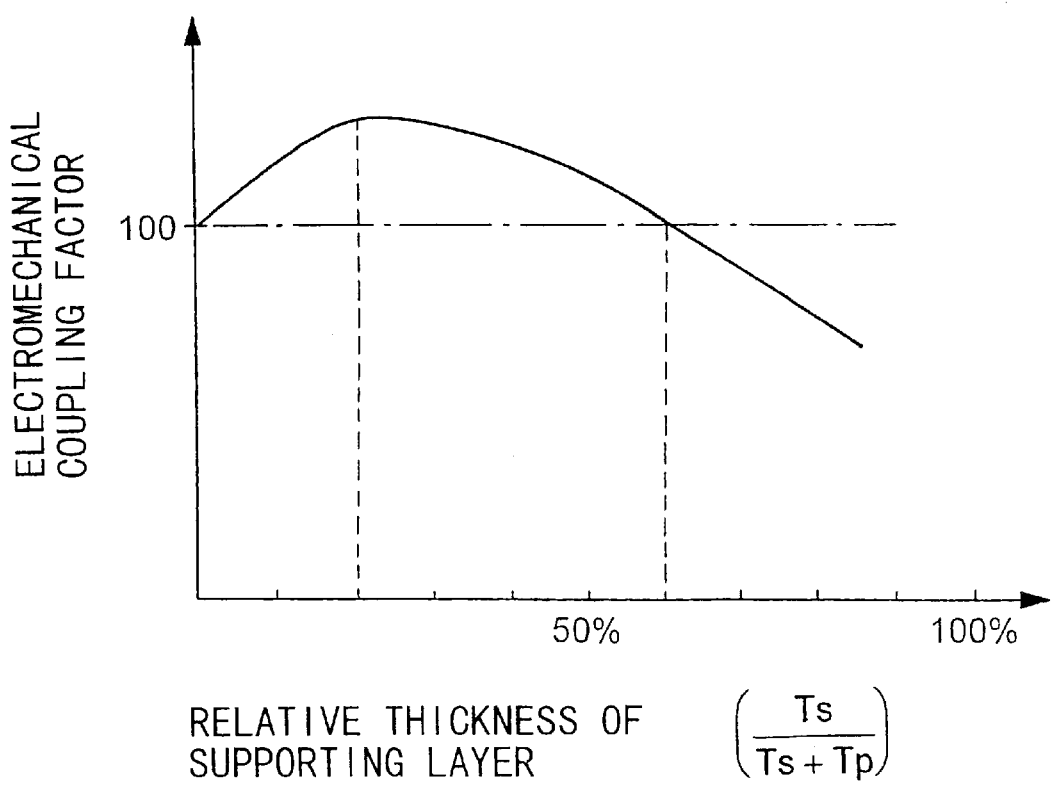
FIG. 21 is a graph showing variation of the electromechanical coupling factor of the pressure measuring device in relation to the relative thickness of the thinner portions of the beam in the pressure measuring device shown in FIG. 6A.

FIG. 21 shows a variation of the electromechanical coupling factor of the piezoelectric element 82 in relation to the relative thickness (Ts/(Ts+Tp)) of the thinner portion 87 (supporting layer for the piezoelectric element 82) when the beam 81 was made of phosphor bronze and the piezoelectric element 82 was made of a ceramic material. The electromechanical coupling factor is a factor indicating the electromechanical conversion efficiency in the pressure measuring device 80, and more specifically it is the square root of the ratio of electrically generated energy to given mechanical energy. Although the result illustrated in FIG. 21 was obtained when the beam 81 was made of phosphor bronze, similar results were obtained when other materials are used for the beam 81. Consequently, it is not intended to limit the present invention to manufacture the beam 81 of phosphor bronze.

As clearly shown in FIG. 21, the electromechanical coupling factor peaked when the relative thickness was approximately 20%, and it decreased gradually when the relative thickness was beyond 20%. In addition, when the relative thickness was approximately 60%, the electromechanical coupling factor was the same as that when the relative thickness or thickness Ts of the thinner portions 87 was zero ("Ts was zero" means that only the piezoelectric element supported the contact portion 86). When the relative thickness was in excess of 60%, the electromechanical coupling factor decreased linearly. From the experimental result, it is understood that the relative thickness of the thinner portion 87 is preferably equal to or less than about 60%. More preferably, the relative thickness of the thinner portion 87 is about 20% in order to enhance the electromechanical coupling factor and conversion efficiency of the piezoelectric element 82. It is supposed that the reason of the result is that when the area of cross section of the thinner portion 87 is large, large strain energy is accumulated therein, so that the electromechanical conversion efficiency is reduced.

On the other hand, it is possible that the contact portions 86 are supported by only piezoelectric elements without the thinner portions 87 of the beam 81. In this case, since the given strain energy can be accumulated in the piezoelectric elements, it is theoretically supposed that the conversion efficiency is increased. However, because of various factors, for example, the accumulating speed of the strain energy and the vibration damping, it is preferable that the piezoelectric elements 82 are mounted on the beam 81 as in the embodiment.

Therefore, it is understood that the piezoelectric elements 82 are preferably mounted on the different beam 81 and the ratio of the area of cross section of the beam 81 to the area of total cross section of the beam 81 and piezoelectric elements 82 is preferably equal to or less than 60% in order to enhance the amplitude of the output signals.

1-2. Usage of Pulse Wave Measuring Device of First Embodiment

Usage of the pulse wave measuring device 1 of the embodiment will be next explained below. Before the use, the second perpendicular sliding plate 18 and the elements suspended therefrom are raised by handling the micrometer head 28, and the interval of the pressing legs 68 and 72 is broadened by handling the micrometer head 57.

First, the patient's arm 7 is placed as shown in FIG. 1, and then three pulse wave measuring units 3 are roughly positioned above the Sunn, Kann, and Syaku of the arm 7 by adjusting the stand 2. Simultaneously, four contact portions 86 of each pulse wave measuring unit 3 are aligned along a line directly above the patient's radial artery 100 Next, the micrometer head 28 is handled, so that the spindle 32 is retracted to lower the second perpendicular sliding plate 18. Simultaneously, the mounting plate 42 suspended from the second perpendicular sliding plate 18 are lowered, whereby the pressing legs 68 and 72 and the contact portions 86 come into contact with the skin of the patient's arm 7. The micrometer head 28 is revolved until the pressing leg 68 presses down the softer part, between the radial artery 100 and the flexor carpi radialis tendon 104, to a predetermined depth.

Then, the micrometer head 57 is handled, so that the spindle 61 is retracted to make the second pressing leg 72 approach the first pressing leg 68. When the second pressing leg 72 arrives at the softer part between the radial artery 100 and the brachioradialis tendon 103 and presses this part down, the micrometer head 57 is stopped to be revolved, so that the movement of the second pressing leg 72 is stopped. In FIG. 7, the second pressing leg 72 before the approach is illustrated with solid lines while the leg 72 after the approach is illustrated with imaginary lines. The contact portions 86 are positioned on the skin above the radial artery 100 according to the aforementioned manner, so that the wave pulses on 12 points are evaluated according to the output signals from 12 piezoelectric elements 82.

As described above, since the second pressing leg 72 can be moved in relation to the first pressing leg 68, both pressing legs 68 and 72 can press down the more elastic or softer parts at the sides of the radial artery 100, whereby four contact portions 86 of each pressure measuring device 80 can be readily positioned on the skin above the radial artery 100. Furthermore, since the distal ends of the contact portions 86 are upper than the distal ends of the pressing legs 68 and 72, the radial artery 100, which is more inflexible or harder than other tissues, is readily positioned between the pressing legs 68 and 72. In other words, twelve contact portions 86 of three pressure measuring devices 80 can be readily positioned on the skin over the radial artery 100 although it is unnecessary for the patient to move his arm 7 and unnecessary for the diagnostician to tend the supporting members 10 in accordance with the embodiment.

If a pressure measuring device is pressed on the organism's surface by a cuff as in the conventional manner, not only the blood vessel but also muscle or tissues around it are pressed flatly, so that it is difficult to adjust the initial pressure on the blood vessel. However, in the embodiment, since two rigid pressing legs 68 and 72 press down the softer parts at the sides of the radial artery 100, it is readily adjust the initial pressure on the radial artery 100 given by the contact portions 86 of the pressure measuring devices 80. Namely, the contact portions 86, which transfer the stress to the piezoelectric elements 82, are used to vary the initial pressure to the radial artery 100 by handling the micrometer head 28.

Figure 22A:
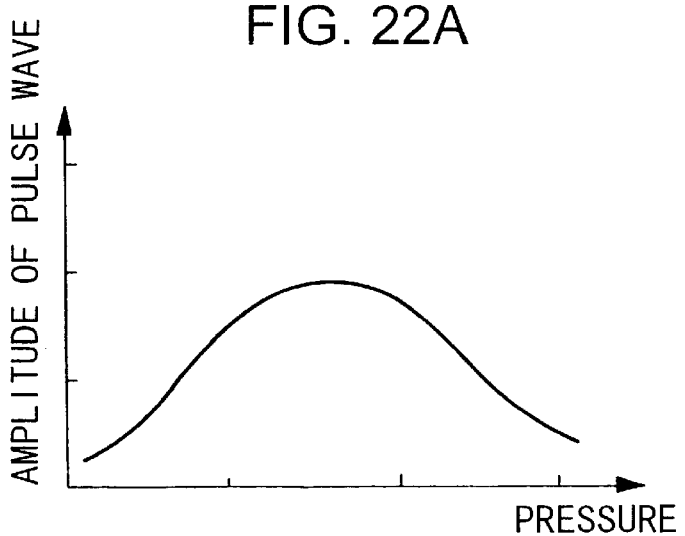
FIG. 22A is a graph showing a tendency curve of Pingmai indicating amplitude variations of human pulse wave due to pressure change given to human skin.
Figure 22B:
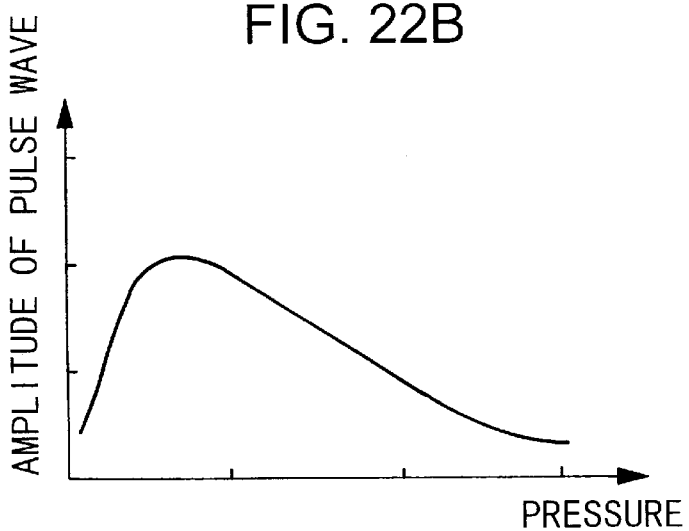
FIG. 22B is a graph showing a tendency curve of Huamai.
Figure 22C:
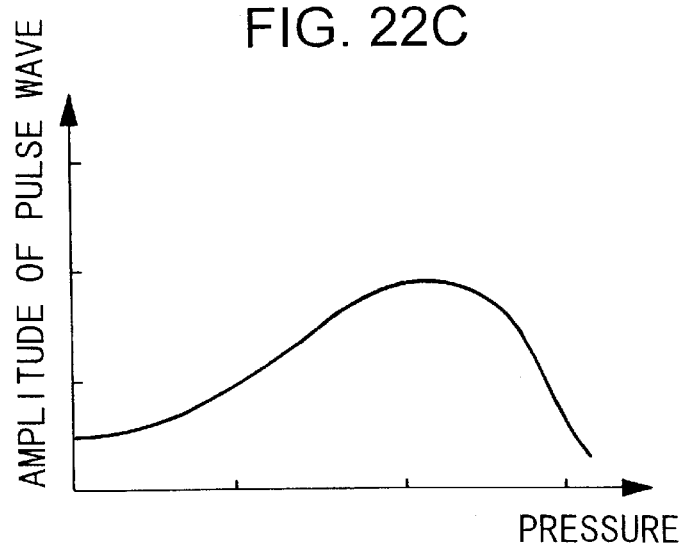
FIG. 22C is a graph showing a tendency curve of Xuanmai.

After the finish of a diagnosis at a depth where the pressing legs 68 and 72 have been stopped, the pressing legs 68 and 72 and the contact portions 86 are further lowered by handling the micrometer head 28 again, whereby the initial pressure on the radial artery 100 is changed. Since blood pulse wave feature varies depending on the initial pressure on the measured blood vessel as depicted in FIGS. 22A to 22C, the patient's physiological condition can be diagnosed in detail. While FIG. 7 shows that the pressing legs 68 and 72 and the contact portions 86 are slightly lowered, FIG. 2A shows that they are greatly lowered.

Figure 8:
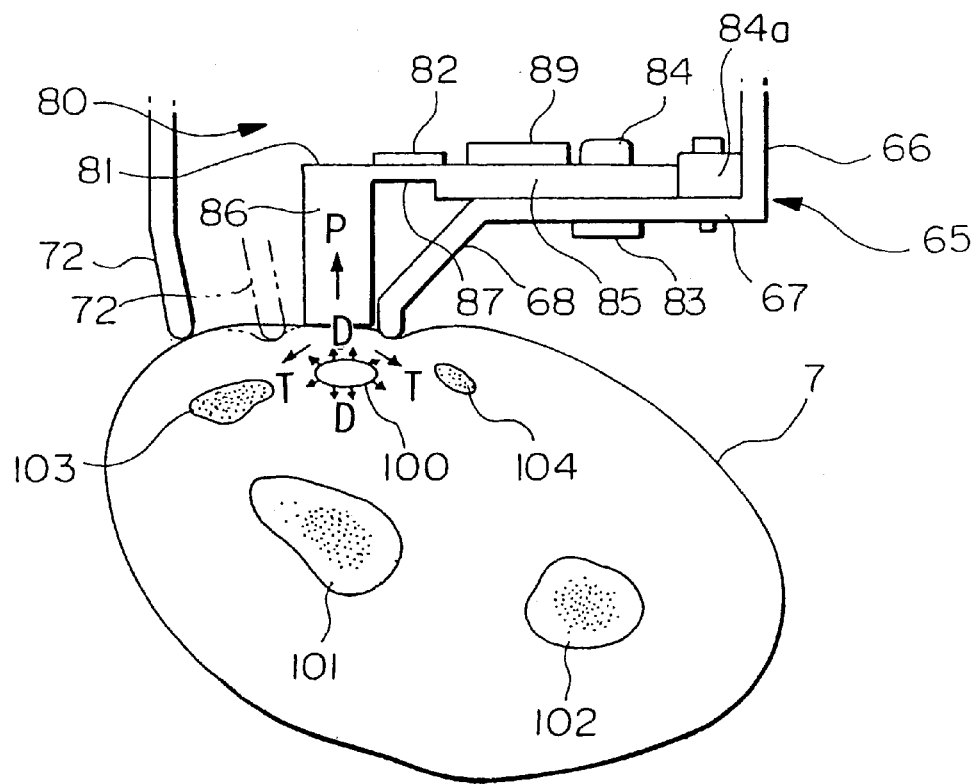
FIG. 8 is a front view showing balance of forces exerted in the contact portion (vessel pressing portion) of the pulse wave measuring unit in FIG. 2A and in the patient's arm.

If the contact portions 86 are lowered, the initial pressure on the artery given by the pressure measuring device 80 is increased. However, if the contact portions 86 are lowered simply, the skins are stretched by the pressing legs 68 and 72 so as to slightly change its tension T depicted in FIG. 8. The pressure measured by the pressure measuring device 80 depends not only on the internal pressure D of the radial artery 100, but also on the skin tension T. Therefore, the initial pressure on the radial artery 100 is not exactly and univocally controlled.

Figure 9:
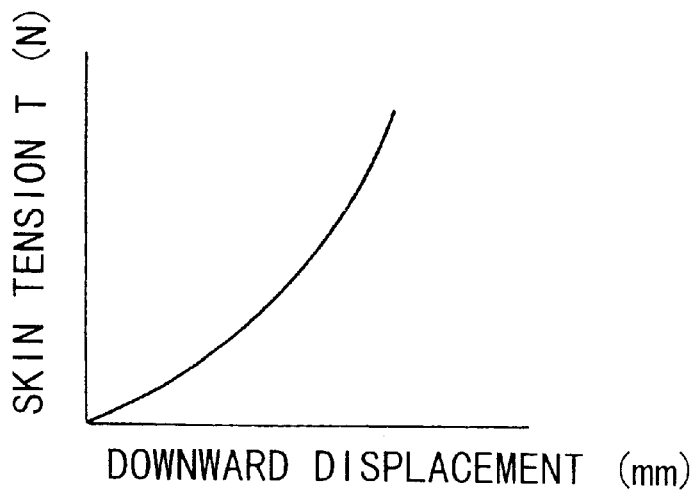
FIG. 9 is a graph showing mutual relationship between the displacement of the pressing legs of the pulse wave measuring unit in FIG. 2A and the skin tension exerted in the patient's arm.

FIG. 9 is a graph showing the correlation between the skin tension T and the displacement of the pressing legs 68 and 72 in the vertical direction when the interval between the pressing legs 68 and 72 is constant. The abscissa of FIG. 9 designates the absolute value of the downward displacement of the first pressing leg 68, wherein the position at which the first pressing leg 68 first comes into contact with the skin is determined to be zero. As shown in FIG. 9, the skin tension T increases in accordance with increase of the initial pressure by the downward movement of the first pressing leg 68 and contact portions 86.

Accordingly, in advance, it is preferable to research the correlation between the skin tension T and the displacement of the pressing legs 68 and 72 in the vertical direction when the interval between the pressing legs 68 and 72 is constant. Alternatively, in advance, it is preferable to research the correlation between the skin tension T and the interval between the pressing legs 68 and 72 when the displacement of the pressing legs 68 and 72 in the vertical direction is constant. Consequently, it is possible to adjust the interval between the pressing legs 68 and 72 by handling the micrometer head 57 on the basis of any of the results of the above researches, thereby excluding the affection of the skin tension T, i.e., making the skin tension T constant at every diagnostic points. By virtue of the research and adjustment, the initial pressure given to the radial artery 100 can be altered to desirable values exactly. The adjustment of the initial pressure is conducted for all of three pulse wave measuring units 3. Under the adjusted pressure, the wave pulses on 12 points are evaluated again according to the output signals from 12 piezoelectric elements 82.

In accordance with the traditional blood pulse wave diagnosis in Oriental medicine, the physiological status of a patient is determined according to more than ten pulse wave characteristics obtained by quantitative or qualitative analyses. In addition, the diagnostician in this field should consider the patients, individual characteristics for diagnosis. For example, if a patient's radial artery has a special characteristic that a level of pressure is exerted in the radial artery as long as a great amount of pressure is applied to the wrist from outside, the diagnostician must determine the patient's waveform in view of his individuality. Therefore, it has been difficult for skill-less diagnosticians to determine the patients, characteristics in the conventional finger-touch manner.

However, by virtue of the embodiment, since the initial pressure can be readily adjusted, the diagnostician can obtain the patient's physiological characteristics quantitatively and qualitatively. Although special diagnosticians using with their sense have conventionally supposed such physiological characteristics, the physiological characteristics can be objectively obtained according to the embodiment. Therefore, the embodiment enables to reduce diagnostician's burden and contributes to inherit the technique for pulse wave diagnosis.

1-3. Variants of First Embodiment

In the first embodiment, the second transverse sliding plate 47 is moved in relation to the first transverse sliding plate 44 using with the micrometer head 57, so that the second pressing leg 72 is moved in relation to the first pressing leg 68. Conversely, the pressing legs 68 and 72 may be constructed in such a manner that the first pressing leg 68 is movable in relation to the fixed second pressing leg 72 in an alteration. Furthermore, both of the pressing legs 68 and 72 may be constructed so as to be movable in another alteration. These alterations may be also applied to the second through fourth embodiments, which will be described later.

Other types of pressure sensors, e.g., strain gauges can be used instead of the piezoelectric elements 82.

In the first embodiment, the beam 81 is supported in a cantilever manner. However, as long as there is a univocal correlation between the load onto each contact portion 86 and the strain in the pressure sensor, other supporting types for beam, e.g., a simple beam manner, can be also adapted.

2. Second Embodiment

Figure 10:
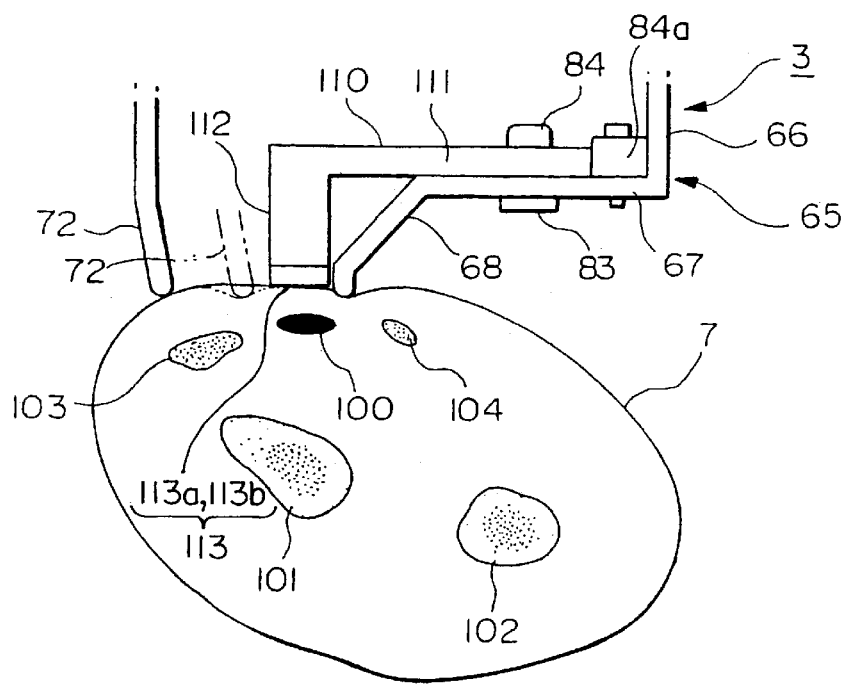
FIG. 10 is a front view showing important parts of a pulse wave measuring device according to a second embodiment of the present invention.

2-1. Structure and Operation of Pulse Wave Measuring Device of Second Embodiment A second embodiment of the present invention will be described next. FIG. 10 shows important parts of the pulse wave measuring device according to the second embodiment. The pulse wave measuring device also includes three pulse wave measuring units 3, which are almost the same as those in the first embodiment, each of the pulse wave measuring units 3 including the supporting member 10. The second embodiment is different from the first embodiment in the sort of the pulsation measuring sensors provided at the supporting member 10. The structural elements common to the first embodiment are not illustrated in FIG. 10.

As shown in FIG. 10, a beam 110 is secured to the horizontal portion 67 of the first pressing plate 65 in the supporting member 10 in the same fixing manner as of the beam 81 in the first embodiment. The beam 110 comprises a planar supported portion 111, which is a proximal portion secured to the horizontal portion 67; and a bent portion 112, which is perpendicularly bent from the supported portion 111. In the same manner as the beam 81 of the first embodiment (see FIGS. 6B and 6C), the beam 110 is divided into four parts, so that a plurality of (four) bent portions 112 are provided in fact.

The bent portions 112 of the beam 110 are situated in the space between the first and second legs 68 and 72. In other words, the pressing legs 68 and 72 are arranged at both sides of the bent portions 112. The distal ends of the bent portions 112 are oriented downward. The distal end faces of the bent portions 112 are fixedly provided with optical pulsation measuring sensors 113, respectively. The optical pulsation measuring sensors 113 may be into contact with the skin over the radial artery 100 of the patient's arm 7. The optical pulsation measuring sensors 113 are upper than the distal ends of the pressing legs 68 and 72. That is, optical pulsation measuring sensors 113 are situated back from the distal ends of the pressing legs 68 and 72. When the beam 110 is not stressed, the optical pulsation measuring sensors 113 are preferably 0.5 to 2 mm, more preferably 0.9 to 1.1 mm upper than the distal ends of the pressing legs 68 and 72.

With such a structure, by handling the micrometer head 27 (see FIGS. 2A, etc.) to lower the beam 110, the optical pulsation measuring sensors 113 on the bent portions 112 of the beam 110 may be pressed against the skin over the radial artery 100, so as to give the radial artery 100 an initial pressure. Consequently, the bent portions 112 and the optical pulsation measuring sensors 113 cooperate to constitute vessel pressing portions or subject pressing portions.

Each of the optical pulsation measuring sensors 113 includes a light-emitting element (emitting means) 113a and a light-receiving element (receiving means) 113b. The light-emitting element 113a and light-receiving element 113b may be in contact with the skin over the radial artery 100, and while the emitting element emits light rays toward the radial artery 100, the receiving element receives the reflected rays by the radial artery 100.

Each of the receiving elements outputs a pulse wave signal (pulsation signal) relating to the strength of the received light. The pulse wave signals are amplified by an amplifier (not shown), and converted to digital signals by an outside analog-to-digital converter having 12 channels. The digital signals are provided to a computer (not shown). The computer operates on the basis of a diagnostic program, referring to the signals provided through 12 channels, so as to diagnose the patient's physiological condition.

The principle of pulse wave measurement by the optical pulsation measuring sensors 113 will be explained below.

When light rays are entered to a thin material, the luminous intensity of transmitting light decreases in comparison with the intensity of incident light by a value which is proportional to the material density and the material thickness. This phenomenon is well known as Lambert-Beer law.

Figure 11A:
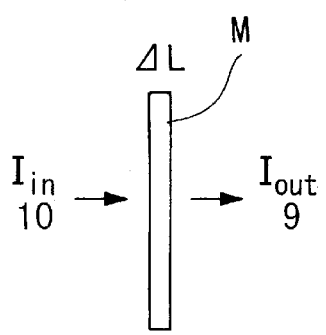
FIG. 11A is a conceptual diagram for describing the correlation between entering light intensity and exiting light intensity according to Lambert-Beer law when the material distance through which light passes is ΔL.
Figure 11B:
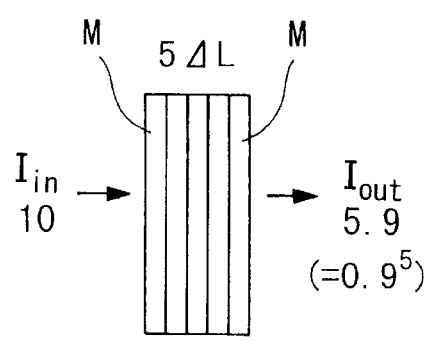
FIG. 11B is a conceptual diagram for describing the correlation between entering light intensity and exiting light intensity according to Lambert-Beer law when the material distance through which light passes is 5ΔL.

With reference to FIGS. 11A and 11B, Lambert-Beer law will be explained in more detail. As indicated in FIG. 11A, there is a correlation between intensity $I_{in}$ of entering light and intensity $I_{out}$ of exiting light which can be expressed in the next equation.

$$I_{out}/I_{in}=1-kC\Delta L \tag{1}$$

where C is the density of the material N, $\Delta L$ is its thickness, and k is its linear absorption coefficient.

If the material thickness is five times longer (see FIG. 11B), the correlation of equation (1) may be rewritten into the next equation.

$$I_{out}/I_{in}=(1-kC\Delta L)^5 \tag{2}$$

According to equation (2), if intensity $I_{out}$ of exiting light is 9 while intensity $I_{in}$ of entering light is 10 in case shown in FIG. 11A, intensity $I_{out}$ of exiting is be 5.9 while intensity $I_{in}$ of entering light is 10 in case shown in FIG. 11B since $I_{out}/I_{in}$ is equal to $0.9^5$.

By integrating equation (1), the correlation between the intensity $I_{in}$ of entering light and intensity $I_{out}$ of light exiting through a distance L can be expressed in the next equation.

$$log(I_{out}/I_{in})=-kCL \tag{3}$$

Equation (3) may be further rewritten into the next equation.

$$I_{out}=I_{in} \times exp(-kCL) \tag{4}$$

As will be understood by the above-equations, if intensity $I_{in}$ of entering light, absorption coefficient K, and distance L are constant, it is possible to estimate the density variation of the material M by measurement of variation of exiting light intensity $I_{in}$. Conversely, by the same principle, it is possible to estimate the density variation of the material M by measurement of intensity variation of reflected light. When the material M is blood, the measurement of the density variation is equivalent to the measurement of the blood pulse wave or the measurement of pulsation.

Figure 12:
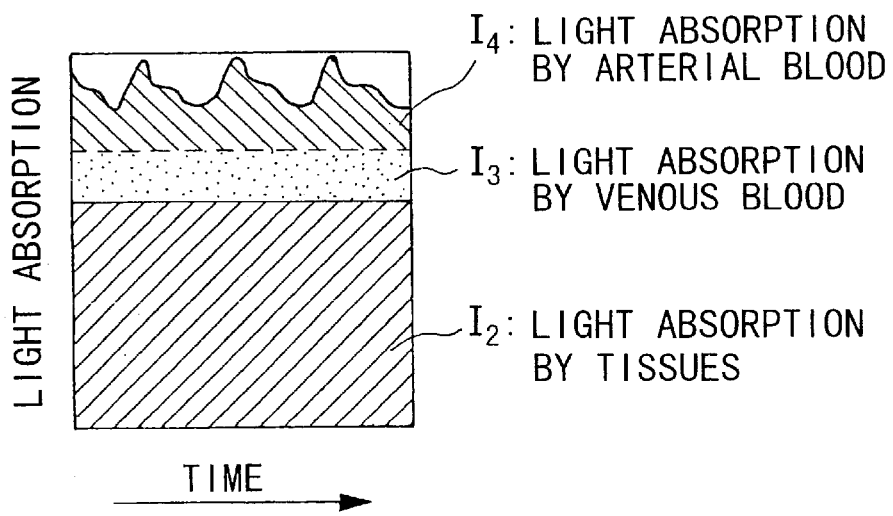
FIG. 12 is a graph showing an example of variation of light absorption while time passes when outside light is entered to a part of a human body including blood vessels.

FIG. 12 is a graph showing an example of variation of light absorption while time passes when outside light is entered to a part of a human body including blood vessels. In FIG. 12, light absorption $I_4$ at an artery varies while light absorption $I_2$ at tissues is constant since the tissue density does not vary. In addition, light absorption $I_3$ at a vein is constant since there is no pulsation in veins and no density variation.

Figure 13:
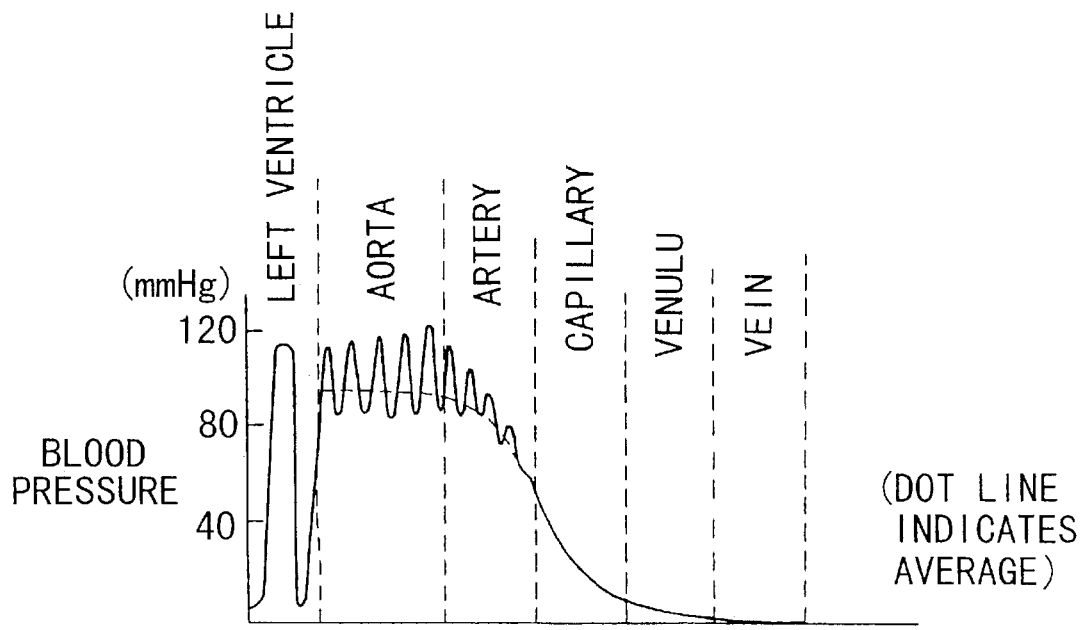
FIG. 13 is a graph showing an example of distribution of blood pressure in various parts of a human body.

FIG. 13 is a graph showing an example of distribution of blood pressure in various parts of a human body. As will be understood from FIG. 13, the blood pulsation decreases as the distance from the heart becomes larger, and disappears at veins. On the other hand, light absorption $I_4$ at an artery changes since the blood density varies in accordance with the blood pulsation as shown in FIG. 12. Accordingly, when a light is entered to the blood vessels, for example, the radial artery 100, the measurement of the intensity of the emitting or reflected light is effected by the light absorption $I_2$ through $I_4$. If the sum of the light absorption $I_3$ at a vein and light absorption $I_4$ at an artery is assumed as 100%, the ratio of light absorption $I_4$ at an artery is from 1 to 2% and the ratio of light absorption $I_3$ is from 98 to 99%.

In accordance with the above-described principle, the optical pulsation measuring sensors 113 receive the light rays reflected by the radial artery 100 and its vicinity, thereby detecting the blood pulse wave. In addition, since the pressing legs 68 and 72 can press down the more elastic or softer parts at the sides of the radial artery 100, four optical pulsation measuring sensors 113 of each pressure measuring device 80 can be readily positioned on the skin above the radial artery 100. Furthermore, since the distal ends of the optical pulsation measuring sensors 113 are upper than the distal ends of the pressing legs 68 and 72, the radial artery 100, which is more inflexible or harder than other tissues, is readily positioned between the pressing legs 68 and 72. In other words, twelve optical pulsation measuring sensors 113 of three pressure measuring device 80 can be readily positioned on the skin over the radial artery 100 although it is unnecessary that the patient moves his arm 7 and unnecessary that the diagnostician tends the supporting members 10 in accordance with the embodiment.

Furthermore, since two rigid pressing legs 68 and 72 press down the softer parts at the sides of the radial artery 100, it is readily adjust the initial pressure on the radial artery 100 given by the optical pulsation measuring sensors 113 of the beams 110.

2-2. Variants of Second Embodiment

Figure 14:
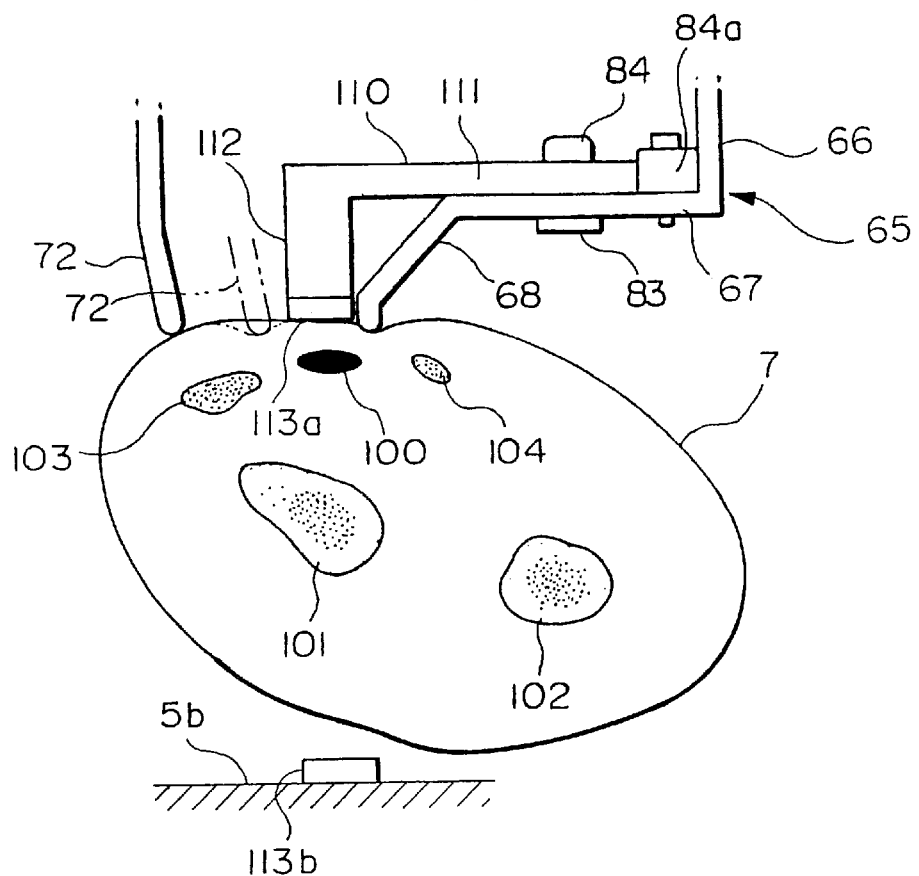
FIG. 14 is a front view showing important parts of a pulse wave measuring device according to a variant of the second embodiment of the present invention.

FIG. 14 illustrates a variant of the second embodiment. In FIG. 14, each of the optical pulsation measuring sensors 113 includes a light-emitting element 113a and a light-receiving element 113b that are separated from each other. Although the light-emitting elements 113a are attached to the lower end faces of the bent portions 112 of the beam 110, the light-receiving elements 113b are arranged at the bottom of the hollow Sb of the arm support 5(see FIG. 1). Another arrangement may be possible in which the light-receiving elements 113b are suspended by the supporting member 10 in such a manner that they can receive the light rays penetrating through the patient's arm 7 from the light-emitting elements 113a attached to the bent portions 112.

3. Third Embodiment

Figure 15:
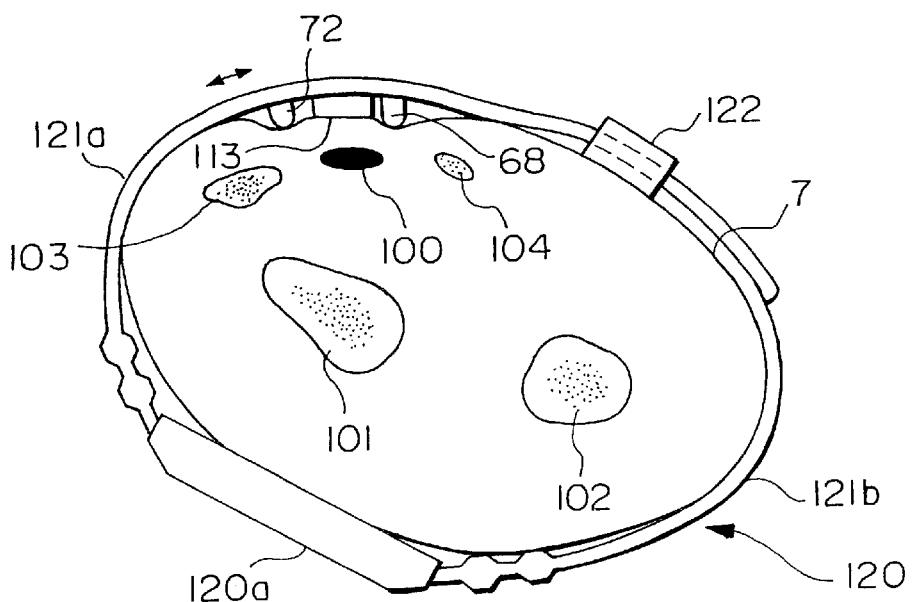
FIG. 15 is a side view showing a pulse wave measuring device according to a third embodiment of the present invention.

FIG. 15 shows a pressure measuring device according to third embodiment of the present invention. In this embodiment, a wristband, constituted of band pieces 121a and 121b, of a watch 120 is used for a supporting member for the pressure measuring device. The wrist band pieces 121a and 121b, attached to both ends of a watch body 120a, cooperate to encircle the patient's wrist and are connected by a known hook 122. The circular length of the watch 120 may be adjusted by loosening and fastening of the hook 122, so that the retaining force to the wrist can be adjusted.

The reverse side of the wrist band piece 121a is provided with an optical pulsation measuring sensor 113. Instead of the sensor 113, another type of pressure measuring sensor may be used. By the retaining force of the wrist band pieces 121a and 121b, the pressure measuring sensor or optical pulsation measuring sensor 113 presses the skin over the radial artery 100.

A pair of pressing legs 68 and 72 are also attached to the reverse side of the wrist band piece 121a, so as to protrude inwards. At least one of the pressing legs 68 and 72 is movable along the circular or lengthwise direction of the wrist band piece 121a, and is stably positioned after stopping the movement. The means for moving and positioning the pressing legs 68 and/or 72 can be a screw, hook, and the like although it is not illustrated.

The pressure measuring sensor or optical pulsation measuring sensor 113 is situated back from the distal ends of the pressing legs 68 and 72. Therefore, the blood vessel is positioned between the pressing legs 68 and 72, so that the sensor can be readily positioned on the skin above the blood vessel. In addition, the measuring device is manufactured lighter in weight very much in accordance with this embodiment.

4. Fourth Embodiment

Figure 16:
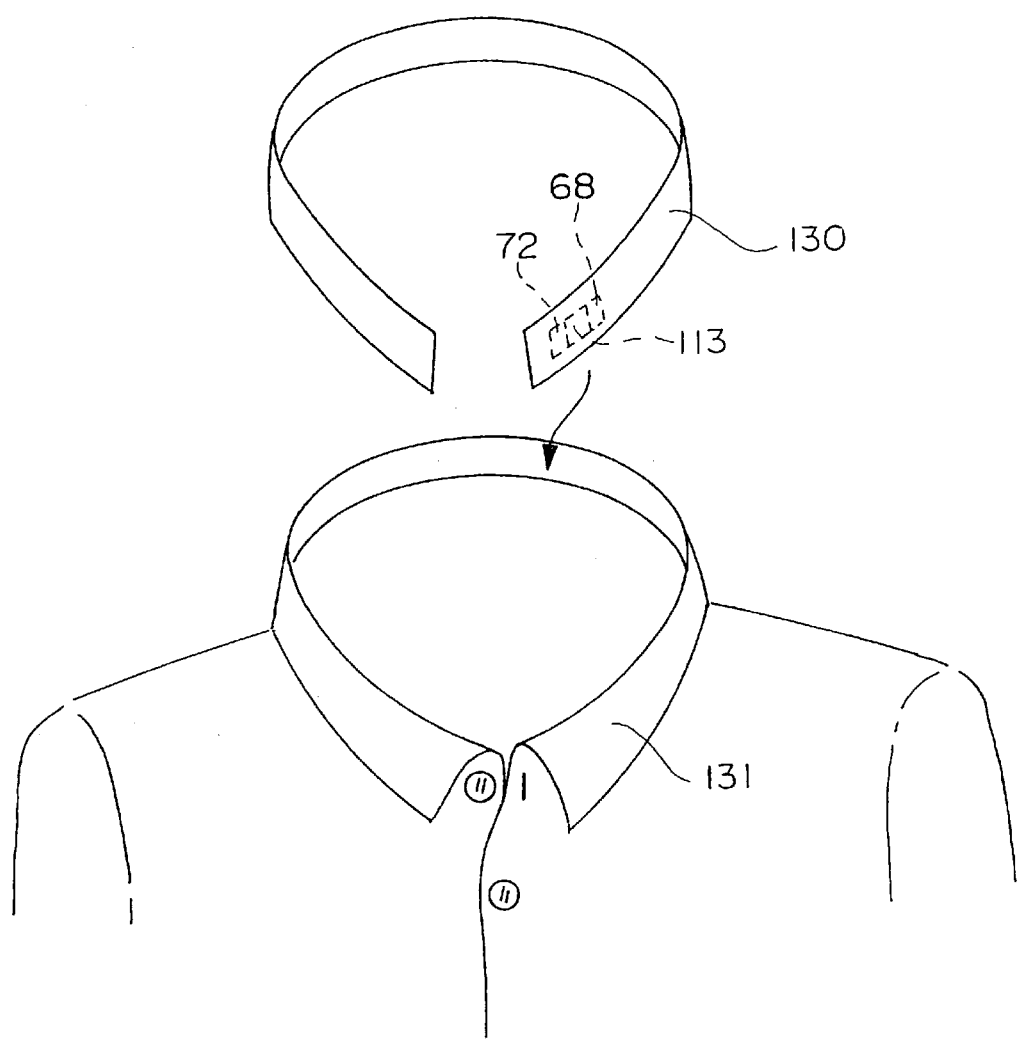
FIG. 16 is a front view showing a pulse wave measuring device according to a fourth embodiment of the present invention.

FIG. 16 shows a pressure measuring device according to a fourth embodiment of the present invention. An elastic arched collar 130 is used for a supporting member for the pressure measuring device in this embodiment. The collar 130 is detachably arranged inside a collar 131, which is a part of clothing, so as to encompass the patient's neck. The circular length of the collar 130 is adjustable, so that the retaining force to the neck can be altered.

A pressure measuring sensor or optical pulsation measuring sensor 113 is secured to the reverse or inner surface of the collar 130, so as to be able to press the skin over the carotid artery of the patient. A pair of pressing legs 68 and 72 are also attached to the reverse surface of the collar 130, so as to protrude inwards. At least one of the pressing legs 68 and 72 is movable along the circular or lengthwise direction of the collar 130, and is stably positioned after stopping the movement.

The pressure measuring sensor or optical pulsation measuring sensor 113 is situated back from the distal ends of the pressing legs 68 and 72. Therefore, the blood vessel is positioned between the pressing legs 68 and 72, so that the sensor can be readily positioned on the skin above the blood vessel.

Figure 23:
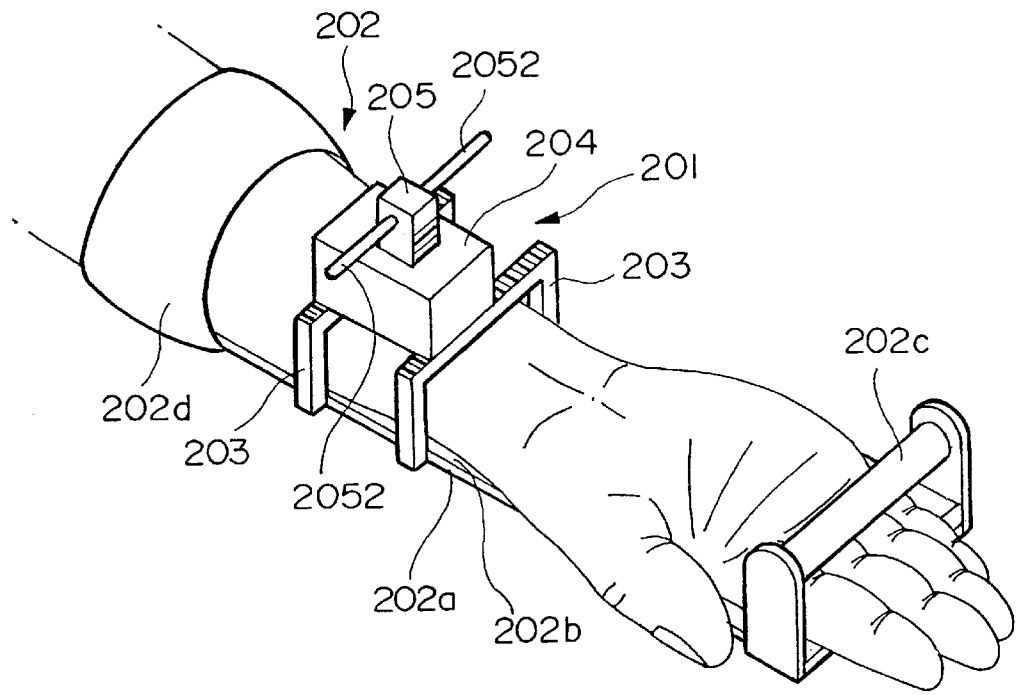
FIG. 23 is a perspective view showing a pulse wave measuring device according to a fifth embodiment of the present invention.
Figure 24:
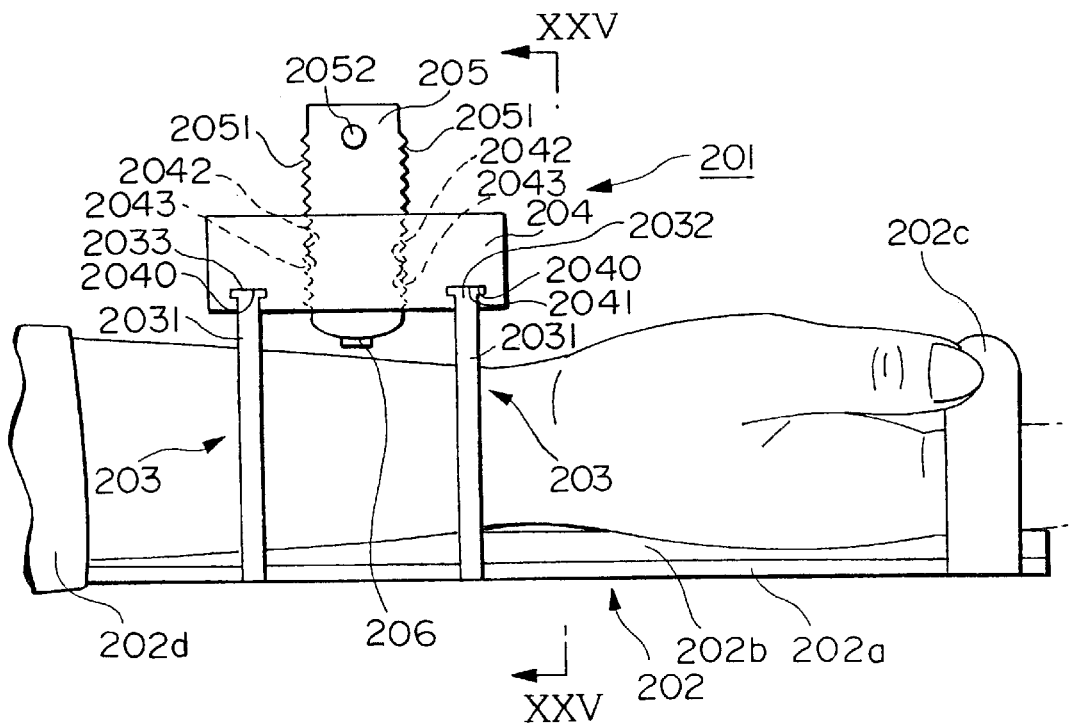
FIG. 24 is a side view showing the pulse wave measuring device in FIG. 23.

5. Fifth Embodiment 5-1. Structure of Pulse Wave Measuring Device of Fifth Embodiment FIG. 23 is a perspective view showing a pulse wave measuring device 201 according to a fifth embodiment of the present invention while FIG. 24 is a side view thereof. As illustrated in FIGS. 23 and 24, the pulse wave measuring device 201 comprises an arm holder 202 on which the patient's arm is held; a pair of supporting members 203 of a slim and bent shape of which both ends are mounted on the arm holder 202; a horizontal or transverse sliding member 204 arranged on the supporting members 203; a perpendicular sliding member 205 attached to the transverse sliding member 204 movably in the perpendicular direction; and a strain gauge or measuring means 206 attached at the bottom of the perpendicular sliding member 205.

Figure 25:
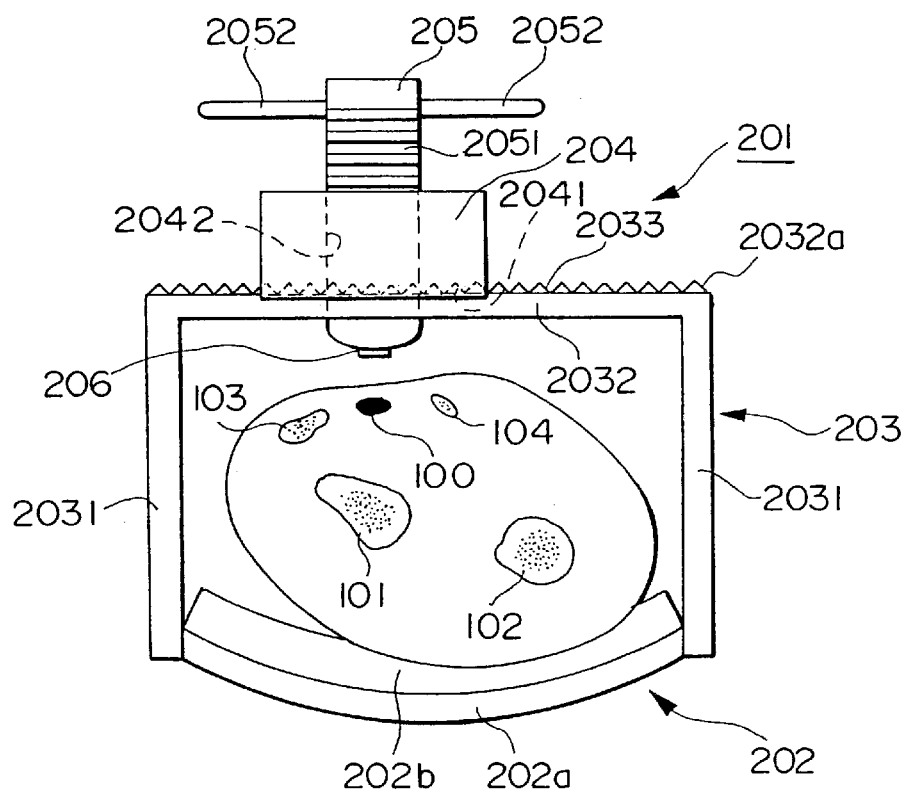
FIG. 25 is a front view taken along line XXV—XXV in FIG. 24.

FIG. 25 is a view taken along line XXV—XXV in FIG. 24. As shown in FIGS. 23 through 25, the arm holder 202 is constituted of a bottom plate 202a having a concave upper surface; a cushion 202b mounted on the bottom plate 202a; a finger holding portion 202c to which the patient's first to fourth fingers are inserted when patient's arm is held in the arm holder 202; and a band 202d loosely wound around the patient's arm. With such a constitution, when the patient's arm is held in the arm holder 202, the arm is not tightly restricted and the skin over the radial artery is oriented upwardly.

Figure 26:
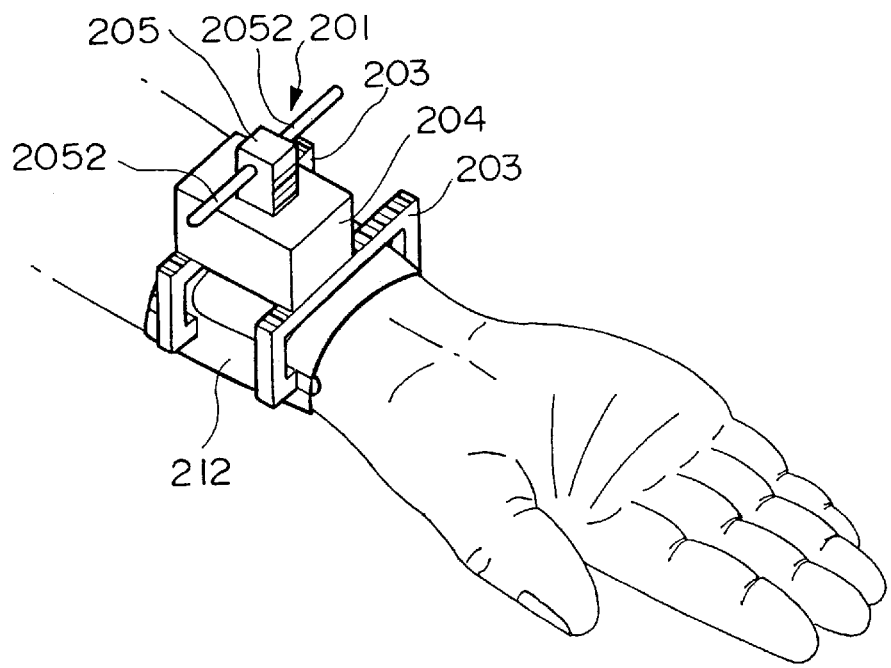
FIG. 26 is a perspective view showing a variant of the pulse wave measuring device according to the fifth embodiment, in which an arm holder is altered.
Figure 27:
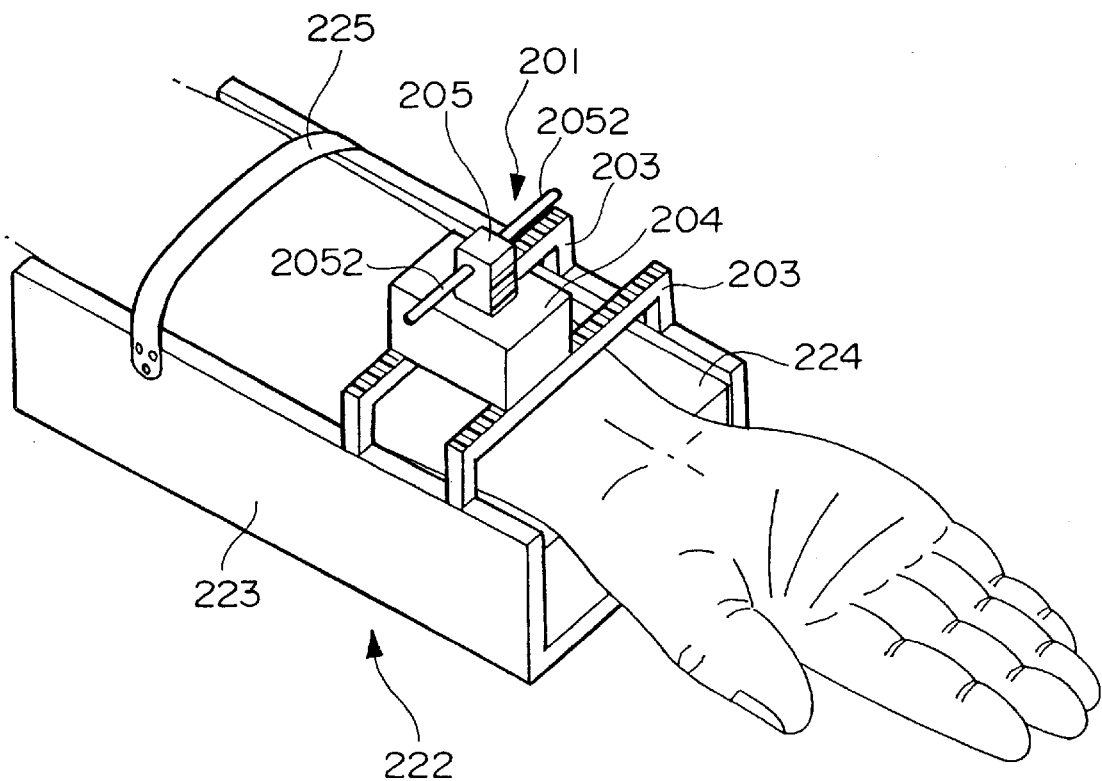
FIG. 27 is a perspective view showing another variant of the pulse wave measuring device according to the fifth embodiment, in which an arm holder is altered.

Although the arm holder 202 is shown in FIGS. 23 through 25, other types of arm holders, e.g., a rubber-band like arm holder 212 in FIG. 26 or arm holder 222 in FIG. 27 may be used instead. The arm holder 222 comprises a holding box 223 of a U-shaped cross section and a lining cushion 224 inside the holding box 223. The patient's arm is put into the U-shaped cushion 224, and then loosely secured by a holding band 225. Another type of arm holder may be utilized as long as it does not retain the patient's arm tightly and the skin directly on the radial artery can be oriented upwardly.

Figure 28:
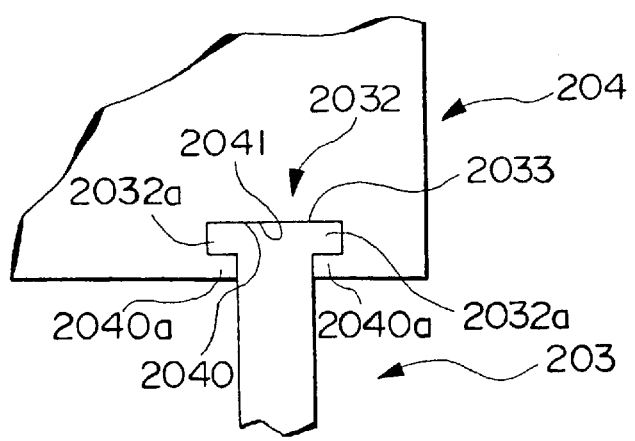
FIG. 28 is an enlarged side view showing the connection of the supporting member and the transverse sliding member of the pulse wave measuring device according to the fifth embodiment.

As shown in FIG. 25, each of the supporting members 203 is constituted of a pair of legs 2031 affixed to the bottom plate 202a of the arm holder 202 by an adhesive, and a supporting portion 2032 of which both ends are supported respectively by the legs 2031. However, another manner for fixing the legs 2031 can be adapted instead of the adhesive. As shown in FIG. 28, ridges 2032a protrude from both sides of the upper portion of each supporting portion 2032. The upper surface of the supporting portion 2032 is provided with a series of teeth, so as to be a zigzag toothed portion 2033.

As illustrated in FIG. 24, a pair of grooves 2040 are formed at both ends of the bottom of the transverse sliding member 204. As shown in FIG. 28, a pair of protruding ridges 2040a are formed at the edges of each groove 2040. The bottom face of each groove 2040 is provided with a series of teeth, so as to be a zigzag or toothed portion 2041, which meshes with the toothed portion 2033 of one of the supporting members 203. The supporting portions 2032 of both supporting members 203 are inserted into the grooves 2040 of the transverse sliding member 204, so that the transverse sliding member 204 is slidable transversely (perpendicularly to FIGS. 24 and 28) in relation to the supporting members 203 and vertical movement of the transverse sliding member 204 is restricted. As shown in FIGS. 24 and 25, a through-hole 2042, penetrating in the vertical direction, is formed at the transverse sliding member 204. As shown in FIG. 24, a pair of opposing inner faces of the through-hole 2042 are provided with teeth, so as to be zigzag or toothed portions 2043.

As shown in FIG. 24, a pair of opposing outer faces of the perpendicular sliding member 205 are provided with teeth, so as to be zigzag or toothed portions 2051, which mesh with the toothed portions 2043 of the through-hole 2042. The perpendicular sliding member 205 is inserted into the through-hole 2042 in such a fashion that the toothed portions 2051 mesh with the toothed portions 2043, whereby the perpendicular sliding member 205 is slidable vertically or perpendicularly in relation to the transverse sliding member 204. A pair of protrusions or pull portions 2052, on which diagnostician's fingers may pull, project from side faces of the perpendicular sliding member 205.

The strain gauge 206 includes a resistor of metal or semiconductor and utilizes piezoresistive effect: i.e., the resistance varies when strain is applied. The strain gauge 206 may be in contact with the skin directly on the radial artery 100 in FIG. 25 by sliding operation of the sliding members 204 and 205, whereby the pulse wave according to pulsation of the radial artery 100 is transmitted to the strain gauge 206. Therefore, by means of continuous measurement of the resistance of the strain gauge 206, the pulse wave can be measured. However, instead of the strain gauge 206, another type of pressure sensor, including a piezoelectric element, that converts strain to electric signal, e.g., electric energy, electroresistance, or electrostatic capacity is utilized. In FIG. 25, a cross section of the arm 7 is shown for clearly indicating the radius 101, ulna 102, brachioradialis tendon 103, and flexor carpi radialis tendon 104.

Figure 29:
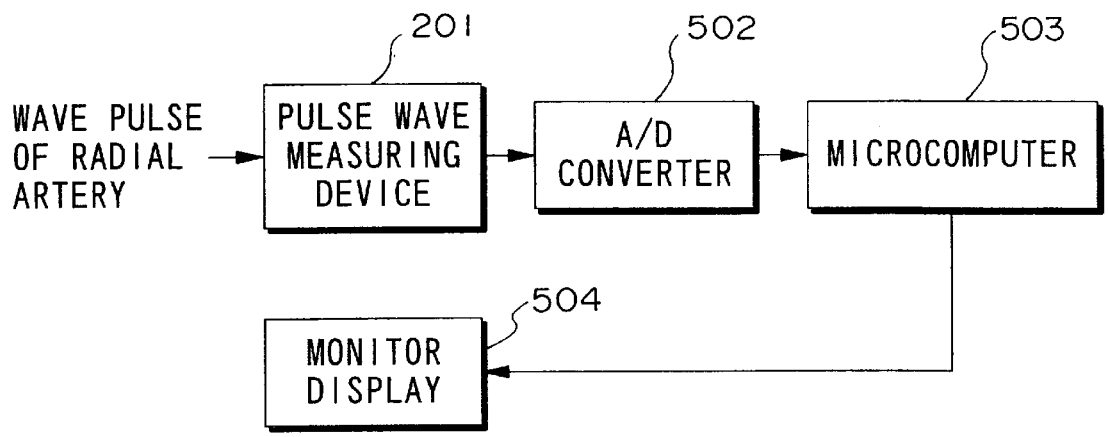
FIG. 29 is a block diagram showing structural elements for showing pulse waveform in a monitor display according to the signals from the pulse wave measuring device of the fifth embodiment.

The signal output from the strain gauge of the pulse wave measuring device 201 is supplied to an analog-to-digital converter 502 shown in FIG. 29, and converted to digital signals at fixed sampling intervals. The digital signals are supplied to a microcomputer 503 that obtains the pulse waveform on the basis of the digital signals and make a monitor display 504 indicate the waveform. Accordingly, the pulse waveform measured by the pulse wave measuring device 201 can be visibly indicated.

5-2. Usage of Pulse Wave Measuring Device of Fifth Embodiment

Next, usage of the pulse wave measuring device 201 according to this embodiment will be described. In the following, the embodiment is exemplified by measurement of pulse wave of the human radial artery. However, it is not intended to restrict the scope of the invention to measure human pulse wave, and rather the device can be used for measuring pulse wave of other animals.

First, the pulse wave measuring device 201 is set on the patient's forearm as shown in FIG. 23. The diagnostician next slides the sliding member 204 transversely in relation to the supporting members 203, thereby positioning the strain gauge 206 at a situation above the radial artery. Since the toothed portion 2033 of the supporting members 203 and the toothed portion 2041 of the transverse sliding member 204 are in mesh with each other, resistance is exerted against the slide. However, the teeth of the toothed portions 2033 and 2041 are formed so that the member 204 slides by diagnostician's fingers at a force, whereby the position adjustment is facilitated.

Figure 30:
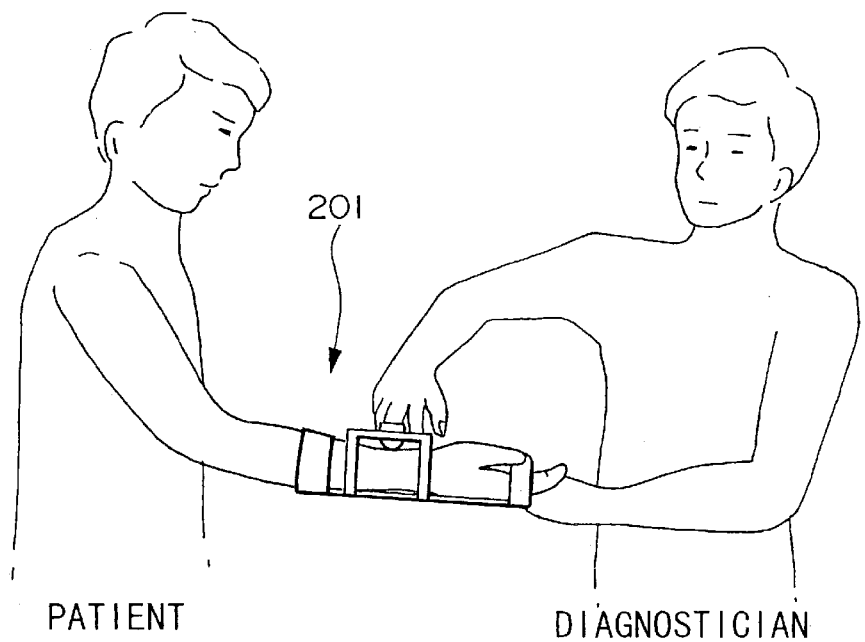
FIG. 30 is an illustration showing usage of the pulse wave measuring device.

Therefore, the diagnostician can adjust the position of the transverse sliding member 204 by finger pushing or finger grasping. Then, he slides the perpendicular sliding member 205 downwardly, so that the strain gauge 206 is positioned to give the radial artery an appropriate pressure. The toothed portions 2043 and 2051 are formed so that the perpendicular sliding member 205 is prevented from being moved by the pulsation force. More specifically, although there is individuality of the force by pulsation, it is preferable that the toothed portions 2043 and 2051 are formed so that the member 205 is moved by a force more than about 300 gram-force. In this case, the diagnostician can easily lower the member 205 overcoming the resistance force although pulsation cannot move the member 205 by the resistance force. Therefore, as shown in FIG. 30, the diagnostician can adjust the height of the strain gauge 206 appropriately using with only one hand in a simple manner. In addition, he can hang his two fingers on the protrusions 2052 and can pull up the perpendicular sliding member 205.

The position of the strain gauge 206 is adjusted while the diagnostician watches it. In addition, trial measurements are conducted at a plurality of positions, and the best position, at which the amplitude of the pulse waveform indicated by the monitor display 504 is the greatest, is selected. Then, the strain gauge 206 is moved to the best position.

After the positioning of the strain gauge 206 at the best measurement position in the above manner described above, the diagnostician commences to measure blood pulse wave. While the measurement, since the toothed portions 2043 and 2051 of the sliding members 204 and 205 are in mesh with each other and the toothed portions 2033 and 2041 of the members 203 and 204 are also in mesh with each other, the strain gauge 206 is not moved by a force equivalent to the pulsation force. Therefore, it is possible to continue to apply an appropriate pressure on the radial artery so as to obtain more accurate measurement results by the embodiment although it has been impossible by conventional devices including a sensor with a pen-like holder. Furthermore, since the pulse wave measuring device 201 is adjusted into the measurement position manually, it is unnecessary to provide a driving device and so on, so that the structure is simplified.

5-3. Variants of Fifth Embodiment

Figure 31:
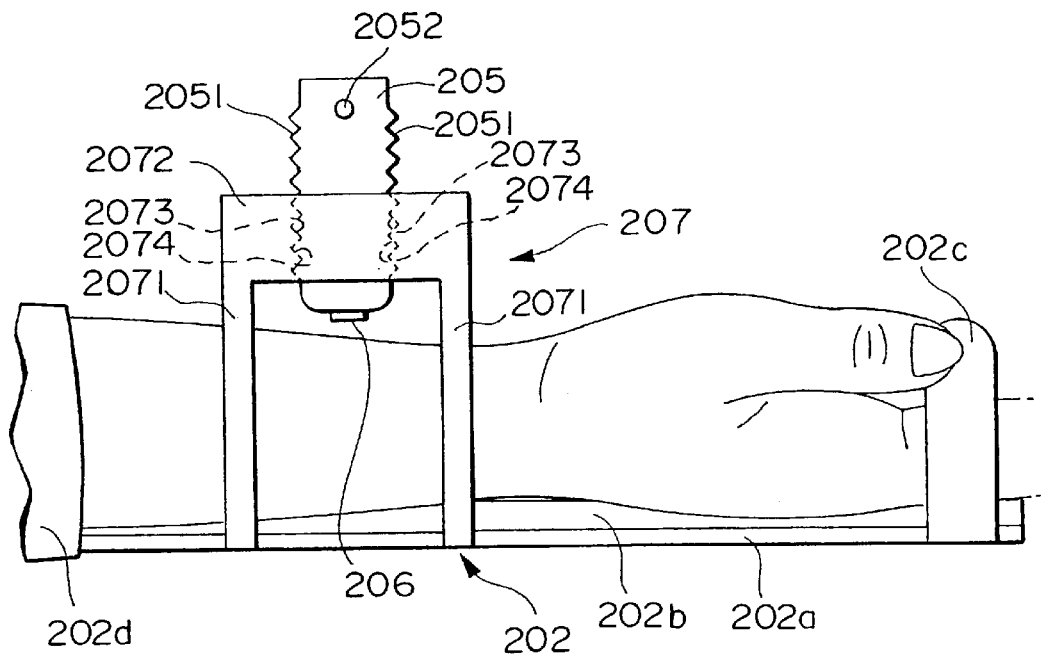
FIG. 31 is a side view showing a variant of the pulse wave measuring device according to the fifth embodiment.

A variant of the fifth embodiment will be explained with reference to FIG. 31. In FIG. 31, the same reference symbols are attached to common structural elements to the fifth embodiment, and description thereof will be omitted.

As shown in FIG. 31, the pulse wave measuring device comprises a supporting member 207 attached to the arm holder 202. The supporting member 207 is constituted of four legs 2071 attached to the arm holder 202; and a supporting portion 2072 of which corners are respectively supported by the legs 2071. A through-hole penetrating in the vertical direction is formed at the supporting portion 2072. The inner opposite surfaces of the through-hole 2073 are provided with teeth, so as to be zigzag or toothed portions 2074, which can be in mesh with the toothed portions 2051 of the perpendicular sliding member 205. The perpendicular sliding member 205 is inserted into the through-hole 2073 in a manner that the toothed portions 2074 and 2051 are meshed with each other.

With such a structure, the height of the strain gauge 206 is vertically adjusted in the simple manner similarly to the fifth embodiment. In addition, after the start of the measurement, the strain gauge 206 is prevented from being moved by a force similar to the pulsation force, so that accurate measurement results can be obtained as similar to the fifth embodiment.

Figure 32:
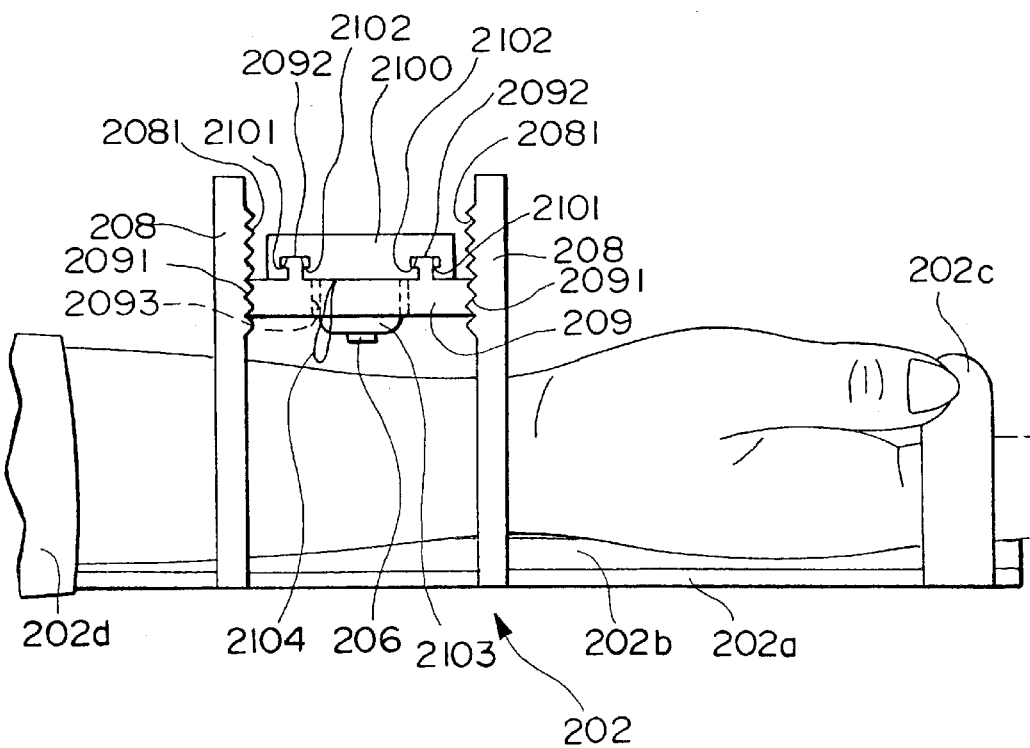
FIG. 32 is a side view showing another variant of the pulse wave measuring device according to the fifth embodiment.

Another variant will be described with reference to FIG. 32. In FIG. 32, the same reference symbols are attached to common structural elements to the fifth embodiment, and description thereof will be omitted. As shown in FIG. 32, the pulse wave measuring device comprises an arm holder 202, supporting members 208, a perpendicular sliding member 209, a horizontal or transverse sliding member 2100, and a strain gauge 206.

Two supporting members 208 are attached to the arm holder 202. A pair of side surfaces of the supporting members 208, which are facing to each other, are provided with the toothed portions 2081. A pair of side opposite surfaces of the perpendicular sliding member 209 are also provided with toothed portions 2091, which mesh with the toothed portions 2081. The perpendicular sliding member 209 is situated between the supporting members 208 in a manner that it is slidable vertically in relation to the supporting members 208. Two toothed potions 2092 are formed on the upper surface of the perpendicular sliding member 209. A through-hole penetrating vertically is formed at the toothed portions 2091. In addition, a loop-shaped strip or a pull portion 2104 is attached to the perpendicular sliding member 209. The diagnostician's fingers can pull on the strap 2104 so as to slide the perpendicular sliding member 209 upwardly.

A pair of grooves 2101 opening downward are formed at the lower surface of the transverse sliding member 2100, and the bottoms thereof are provided with teeth, so as to be toothed portions 2102, which are in mesh with the toothed potions 2092 of the perpendicular sliding member 209. The toothed potions 2092 of the perpendicular sliding member 209 are inserted into the grooves 2102 of the transverse sliding member 2100, so that the transverse sliding member 2100 is slidable in relation to the perpendicular sliding member 209 in the transverse direction (perpendicular direction to FIG. 32) and vertical movement of the transverse sliding member 2100 is restricted.

A projection 2103, which is formed at the lower surface of the transverse sliding member 2100, protrudes downward and is inserted into the through-hole 2093 of the perpendicular sliding member 209. A strain gauge 206 is mounted on the lowermost end of the projection 2103.

With such a structure, the position of the strain gauge 206 is vertically and transversely adjusted in the simple manner similarly to the fifth embodiment. In addition, after the start of the measurement, the strain gauge 206 is prevented from being moved by a force similar to the pulsation force, so that accurate measurement results can be obtained as similar to the fifth embodiment.

Figure 33:
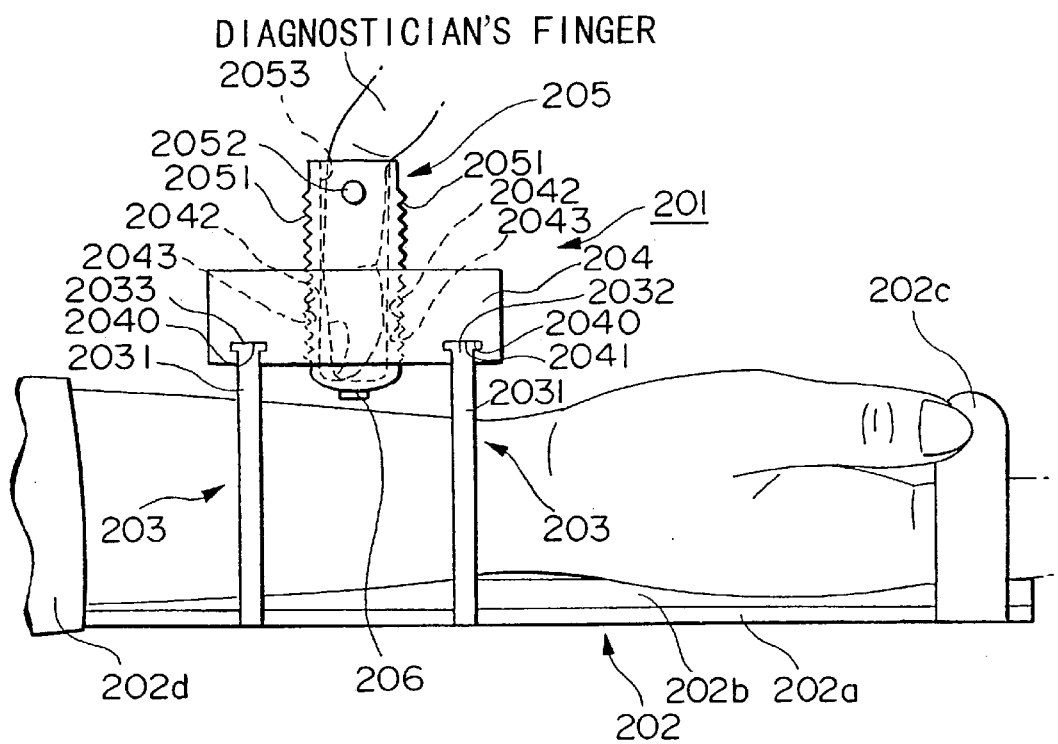
FIG. 33 is a side view showing another variant of the pulse wave measuring device according to the fifth embodiment.

In another variant of the fifth embodiment, as shown in FIG. 33, it is possible to make a finger-insertion hole 2053, into which a finger of the diagnostician can be inserted, at the perpendicular sliding member 205. With such a structure, the diagnostician can insert his finger into the insertion hole 2053 and can press down the perpendicular sliding member 205. Therefore, it is easy to adjust the position of the strain gauge 206. In addition, the inserted finger with another finger or thumb can readily pick up the strain gauge 206. The same finger-insertion hole may be made at the perpendicular sliding member 205 in FIG. 31 or the transverse sliding member 2100 in FIG. 32.

Figure 34:
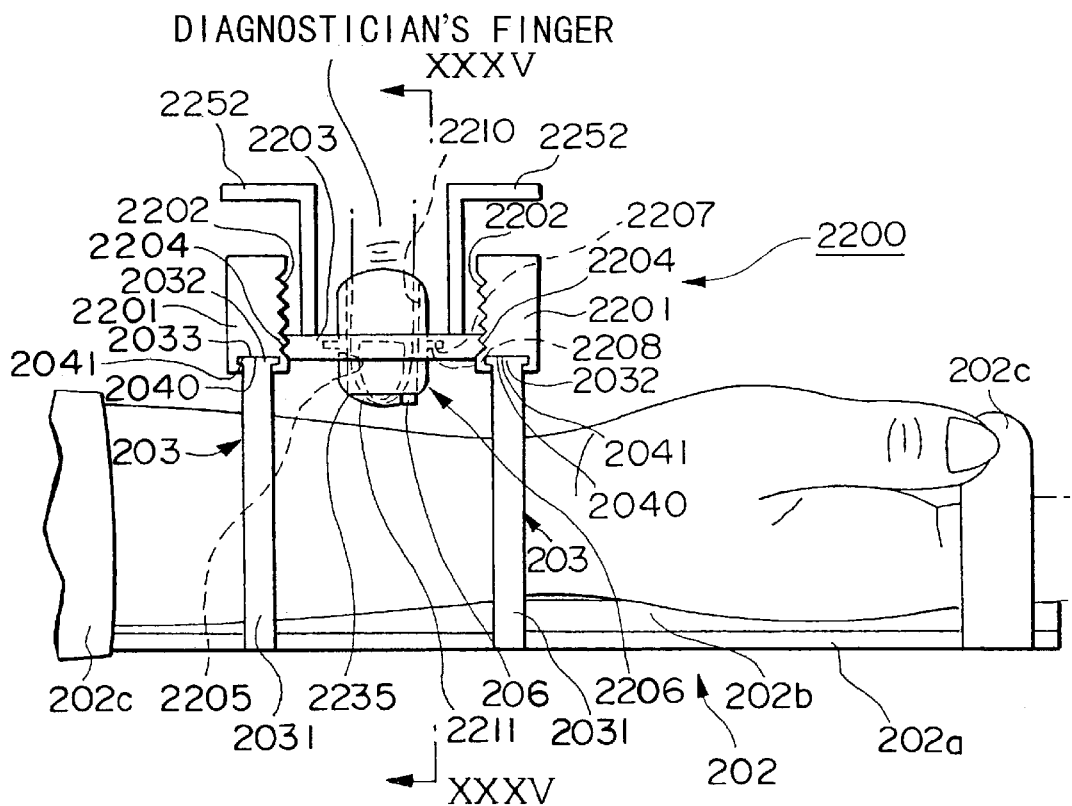
FIG. 34 is a side view showing the pulse wave measuring device according to the sixth embodiment of the present invention.
Figure 35:
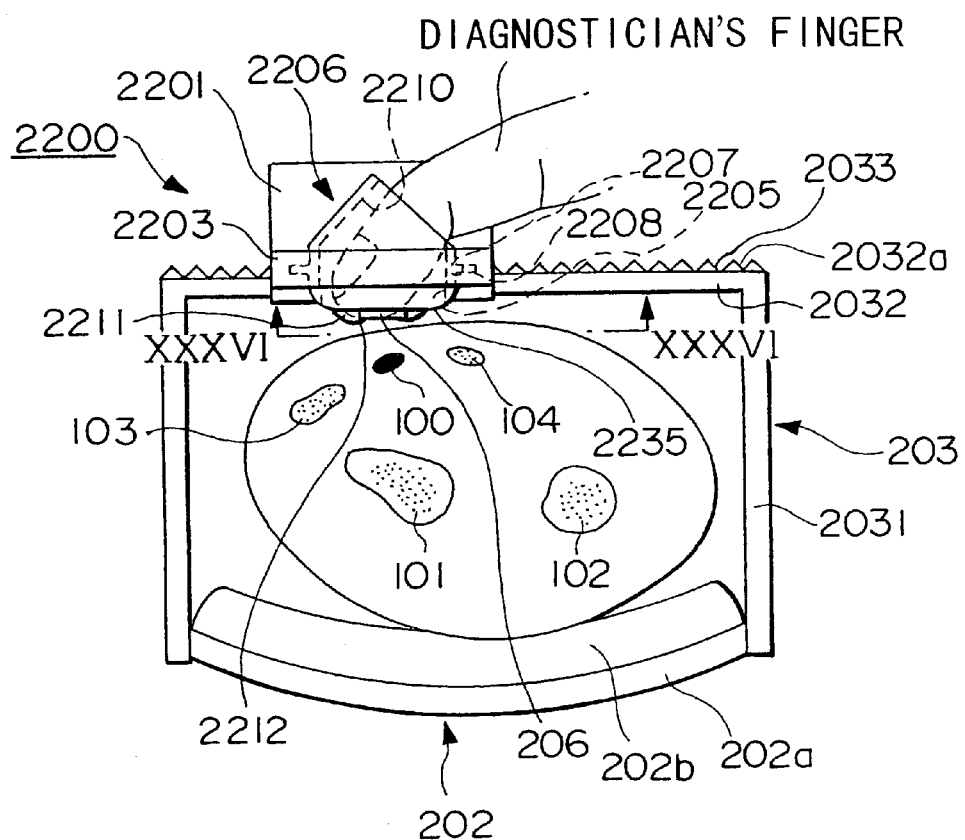
FIG. 35 is a front view taken along line XXXV—XXXV in FIG. 34.

6. Sixth Embodiment 6-1. Structure of Pulse Wave Measurement Device of Sixth Embodiment With reference to FIGS. 34 and 35, a pulse wave measurement device according to a sixth embodiment, which is more preferable than the fifth embodiment, will be described. In FIGS. 34 and 35, the same reference symbols are attached to common elements to the fifth embodiment, and description thereof will be omitted.

FIG. 34 shows a pulse wave measuring device 2200 comprising a pair of supporting members 203, and a pair of transverse or horizontal sliding members 2201 slidably and respectively arranged on the upper surfaces of the supporting members 203. Side surfaces, facing to each other, of the transverse sliding members 2201 are provided with toothed portions 2202. A perpendicular sliding member 2203 is situated between the transverse sliding members 2201 in a manner that the member 2204 is slidable vertically. The opposing side surfaces of perpendicular sliding member 2203 are provided with toothed portions 2204, which mesh, with the toothed portions 2202.

A through-hole penetrating perpendicular is formed at the perpendicular sliding member 2203. A finger-insertion member 2206 is rotatably inserted into the through-hole 2205. More specifically, a circular groove 2207 is formed at the inner surface of the through-hole 2205. A peripheral ridge, formed on the outer peripheral surface of the finger-insertion member 2206, engages with the groove 2207, thereby restricting vertical movement of the finger-insertion member 2206. In addition, a pair of L-shaped pull members 2252, on which the diagnostician's fingers can hang or pull, are mounted on the perpendicular sliding member 2203.

As best shown in FIG. 35, the finger-insertion member 2206 is bent at an angle of about 45 degree in relation to the perpendicular line to the tangential plane on the patient's skin. A finger of the diagnostician may be inserted into the insertion hole 2210 formed at the finger-insertion member 2206. The lower opening 2235 of the insertion hole 2210 at the lowermost end of the finger-insertion member 2206 is covered with an elastic film or membrane 2211. A small groove 2212 is formed at the elastic membrane 2211. When measuring blood pulse wave, the elastic membrane 2211 press down the more elastic or softer skin parts at the sides of the radial artery, whereby the skin over the radial artery is readily positioned in the groove 2212.

Figure 36:
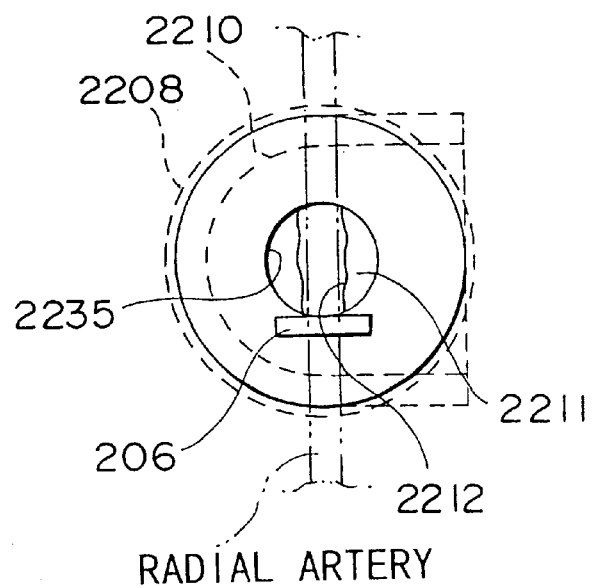
FIG. 36 is a bottom view taken along line XXXVI—XXXVI in FIG. 34.

FIG. 36 is a view taken along line XXXVI—XXXVI of FIG. 35, especially showing the finger-insertion member 2206. As shown in FIG. 36, a strain gauge 206 is mounted on the lower end surface of the finger-insertion member 2206. The strain gauge 206 is arranged at the periphery of the opening 2235 and in the same line of the groove 2212, so that the strain gauge 206 is positioned on the radial artery 100 when the skin over the radial artery 100 is positioned in the groove 2212.

6-2. Usage of Pulse Wave Measuring Device of Sixth Embodiment

Next, usage of the pulse wave measuring device 2200 according to the sixth embodiment will be next described. In the following, the embodiment is exemplified by measurement of pulse wave of the human radial artery. However, it is not intended to restrict the scope of the invention to measure human pulse wave, and rather the device can be used for measuring pulse wave of other animals.

First, the pulse wave measuring device 2200 is set on the patient's forearm as shown in FIGS. 34 and 35. The diagnostician next inserts his finger into the finger-insertion hole 2210. Then, he slides the transverse sliding members 2201 as similar to the fifth embodiment, thereby positioning the strain gauge 206 above the radial artery 100.

After the positioning of the transverse sliding members 2201, the diagnostician slides the perpendicular sliding member 2203 downwardly using with the finger inserted into the hole 2210, so that the strain gauge 206 is moved at a position to give an appropriate pressure to the radial artery. He can search the appropriate position using with his finger sense although there is the elastic membrane 2211 between the finger and the patient's skin. That is, the strain gauge 206 can be positioned at the appropriate position by means of the diagnostician's sense of touch. Consequently, in accordance with this embodiment, the positioning of the strain gauge 206 is more accurate and easier than that according to the fifth embodiment using with the diagnostician's sense of sight.

In addition, since the insertion hole 2210 is inclined at 45 degree, the finger inclination, articular bend, contact feeling, and the like may be natural and similar to those in the normal or manual diagnosis. Therefore, the strain gauge 206 is positioned accurately.

Figure 37:
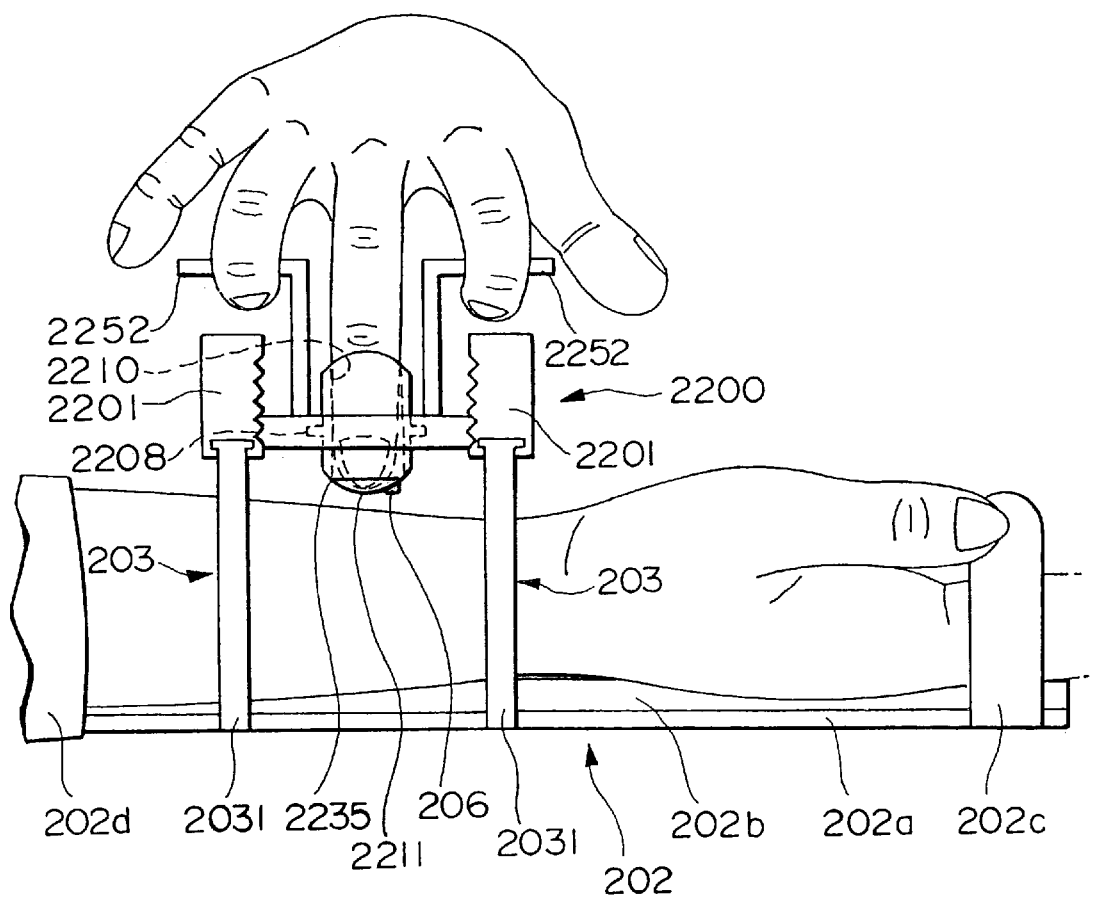
FIG. 37 is a side view showing the pulse wave measuring device in FIG. 34 in which the diagnostician is adjusting the position of the sensor.

As shown in FIG. 37, the diagnostician can insert his second finger into the insertion hole 2210, and can pull his forefinger and third finger on the pull members 2252, so as to lift the perpendicular sliding member 2203 with the strain gauge 206. Therefore, the adjustment of the strain gauge 206 to the appropriate position can be facilitated while using with the finger's sense of touch.

After the completion of the positioning of the strain gauge 206 as described above, the pulse wave measurement is started. While the measurement, since the toothed portions 2202 and 2204 of the sliding members 2201 and 2203 are in mesh with each other and the toothed portions 2033 and 2041 of the members 203 and 204 are also in mesh with each other, the strain gauge 206 is not moved by a force equivalent to the pulsation force.

Additionally, by revolving the finger-insertion member 2206, the positioning of the patient's skin over the radial artery 100 into the groove 2212 is facilitated. More specifically, by revolving the member 2206, if the insertion hole 2210 is oriented as shown in FIG. 35, so that the diagnosticians finger in the hole 2210 is aligned in a plane perpendicular to the patient's forearm, the groove 2212 is oriented in the direction of the radial artery. Consequently, if the diagnostician aligns his finger in the hole 2210 in the direction, which is convenient for detecting the pulse manually, the patient's skin over the radial artery 100 is readily positioned into the groove 2212.

Accordingly, the radial artery 100 is stably positioned in the groove 2212, so that the strain gauge 206 is prevented from being moved in the transverse direction. In addition, the adjustment of the pressure on the blood vessel can be facilitated. Therefore, it is possible to continue to give an appropriate pressure on the radial artery, whereby more accurate measurement results can be obtained. The pulse waveform is visually indicated in the monitor display 504 on the basis of the output signal from the strain gauge 206. In the measurement, since the finger-insertion member 2206 is rotatably inserted in the through-hole 2205, the diagnostician can naturally arrange his finger in relation to the patient's arm in both cases of the patient's right and left hands.

Figure 38:
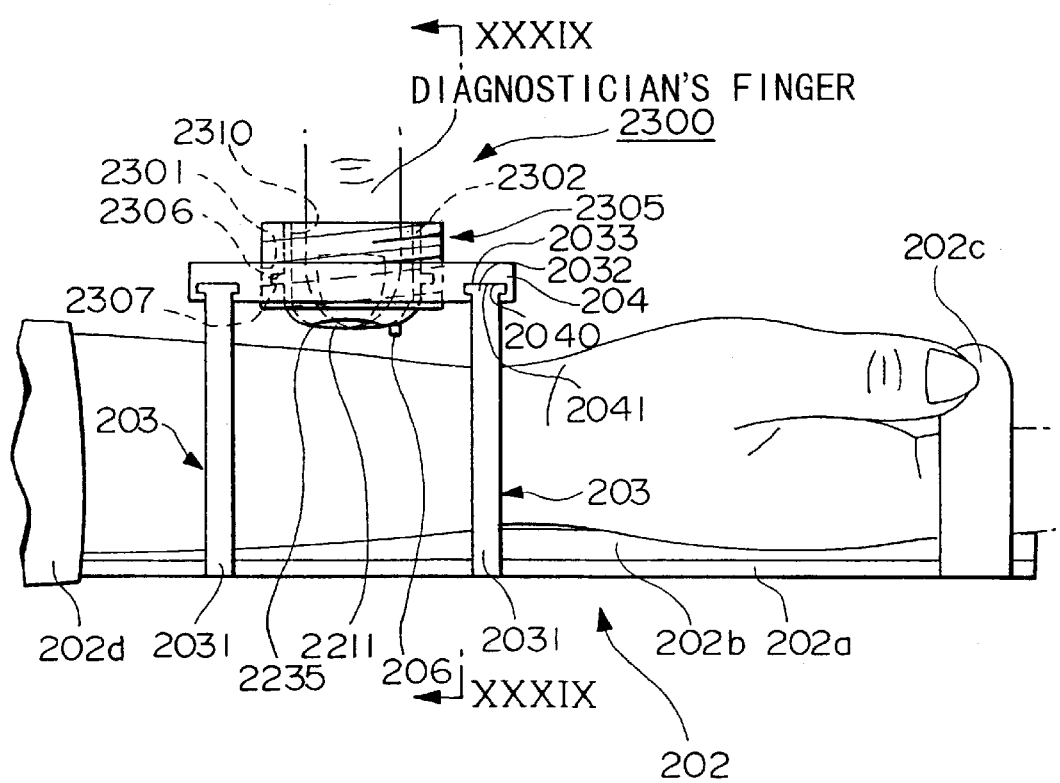
FIG. 38 is a side view showing the pulse wave measuring device according to the seventh embodiment of the present invention.
Figure 39:
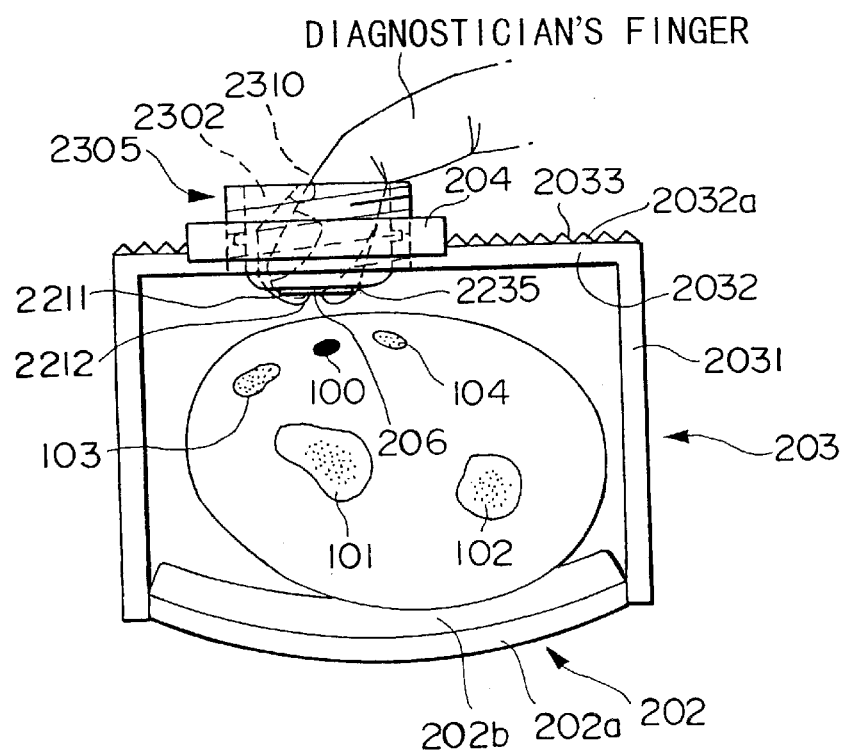
FIG. 39 is a front view taken along line MXIX—MXIX in FIG. 39.

7. Seventh Embodiment 7-1. Structure of Pulse Wave Measurement Device of Seventh Embodiment Next, with reference to FIGS. 38 and 39, a pulse wave measuring device of a seventh embodiment of the present invention will be described. In FIGS. 38 and 39, the same reference symbols are attached to common elements to the fifth or sixth embodiment, and description thereof will be omitted.

As shown in FIGS. 38 and 39, the pulse wave measuring device 2300 includes a transverse sliding member 204 at which formed is a screw hole 2301 penetrating vertically. A hollow bolt 2305 is screwed in the screw hole 2301. A finger-insertion member 2302 is rotatably inserted in the inner space of the hollow bolt 2305. A peripheral ridge 2307 formed at the finger-insertion member 2302 is put in the circular groove 2306 formed at the inner surface of the hollow bolt 2305, so that vertical movement of the finger-insertion member 2302 is restricted.

As shown in FIG. 39, the finger-insertion member 2302 is provided with a finger-insertion hole 2301, that is inclined at about 45 degree, into which the diagnostician's finger may be inserted. The lower opening 2235 of the insertion hole 2210 at the lowermost end of the finger-insertion member 2206 is covered with an elastic film or membrane 2211. A small groove 2212 is formed at the elastic membrane 2211. When measuring blood pulse wave, the elastic membrane 2211 press down the more elastic or softer skin parts at the sides of the radial artery and the skin over the radial artery is readily positioned in the groove 2212. A strain gauge 206 is attached to the lower surface of the finger-insertion member 2302 as similar to the sixth embodiment (see FIG. 36).

7-2. Usage of Pulse Wave Measuring Device of Seventh Embodiment

Next, usage of the pulse wave measuring device 2300 according to the seventh embodiment will be next described. In the following, the embodiment is exemplified by measurement of pulse wave of the human radial artery. However, it is not intended to restrict the scope of the invention to measure human pulse wave, and rather the device can be used for measuring pulse wave of other animals.

First, the pulse wave measuring device 2300 is set on the patient's forearm as shown in FIG. 38. The diagnostician next slides the sliding member 204 transversely, as similar to the fifth embodiment, thereby positioning the strain gauge 206 above the radial artery 100.

After the positioning of the transverse sliding member 204, the diagnostician rotates the hollow bolt 2305 to move the finger-insertion member 2302 downwardly while the finger is inserted into the hole 2310, so that the strain gauge 206 is moved at a position to give an appropriate pressure to the radial artery 100. He can search the appropriate position using with his finger sense although there is the elastic membrane 2211 between the finger and the patient's skin. That is, the strain gauge 206 can be positioned at the appropriate position by means of the diagnostician's sense of touch. Consequently, in accordance with this embodiment as similar to the sixth embodiment, the positioning of the strain gauge 206 is more accurate and easier in comparison with the fifth embodiment. In this case, while the second finger is inserted in the insertion hole 2310, the other fingers may revolve the hollow bolt 2305 to move it vertically. Therefore, while the second finger can search the appropriate position, the position of the strain gauge 206 is adjusted.

After the completion of the positioning of the strain gauge 206 as described above, the pulse wave measurement is started. While the measurement, since the hollow bolt 2305 attached to the finger-insertion member 2302 is held in the screw hole 2301, the strain gauge 206 is not moved although the pulsation force is exerted thereto.

Additionally, by revolving the finger-insertion member 2302, the positioning of the patient's skin over the radial artery 100 into the groove 2212 is facilitated as similar to the sixth embodiment. Accordingly, the radial artery 100 is stably positioned in the groove 2212, so that the strain gauge 206 is prevented from being moved in the transverse direction. In addition, the adjustment of the pressure on the blood vessel can be facilitated. Therefore, it is possible to continue to give an appropriate pressure on the radial artery, whereby more accurate measurement results can be obtained. The pulse waveform is visually indicated in the monitor display 504 on the basis of the output signal from the strain gauge 206. In the measurement, since the finger-insertion member 2302 is rotatably inserted in the hollow bolt 2305, the diagnostician can naturally arrange his finger in relation to the patient's arm in both cases of the patient's right and left hands.

8. Other Variants or Modifications

Figure 40:
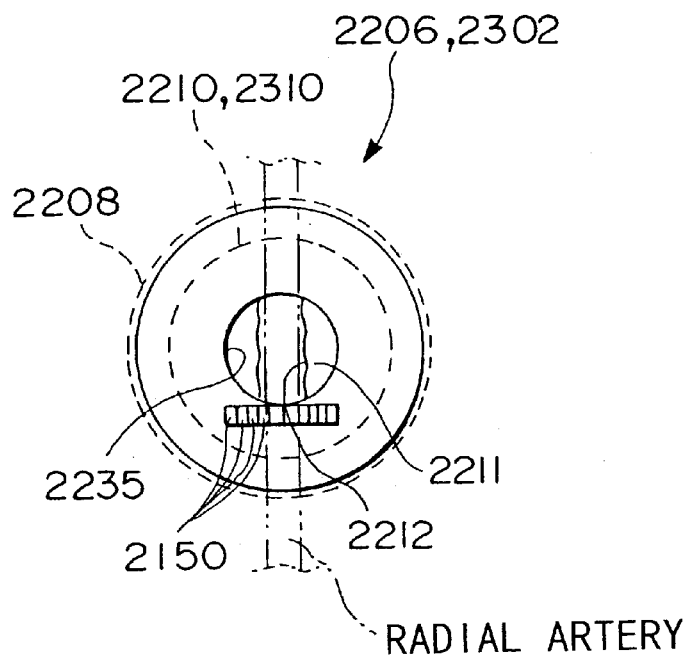
FIG. 40 is a bottom view showing a variant of a finger-insertion member, which may be used in any of the sixth and seventh embodiments.

FIG. 40 shows a variant of finger-insertion member, which may be used in any of the sixth and seventh embodiments. As shown in FIG. 40, at the lower surface of the finger-insertion member 2206 or 2302, a plurality of strain gauges 2150 are arranged abreast at the periphery of the opening 2235. The center one of the strain gauges is aligned in the same line of the groove 2212 of the elastic membrane 2211.

With such a structure, the positional or angular relationship between each strain gauge 2150 and the blood vessel can be solely determined when the strain gauges are positioned. Therefore, the displacement of the blood vessel at various angles according to the pulsation can be evaluated by analyzing pulse waveforms obtained respectively by the strain gauges 2150.

Figure 41:
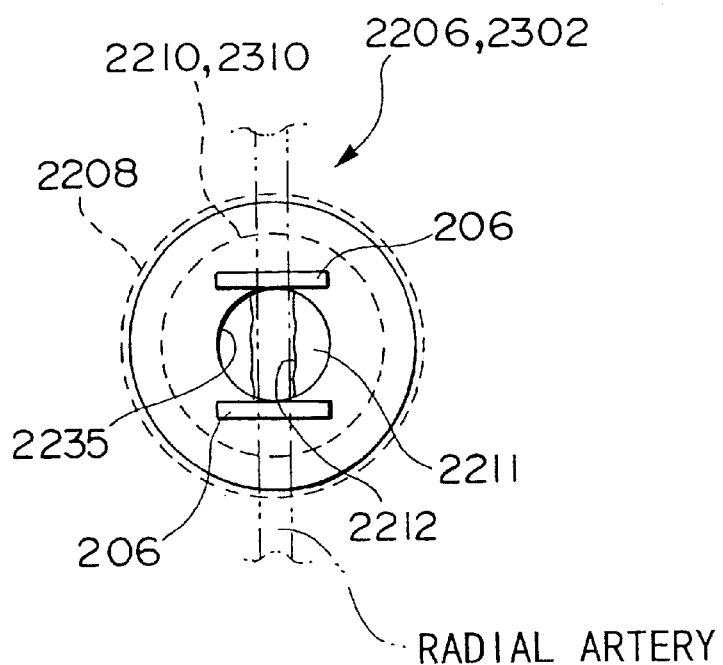
FIG. 41 is a bottom view showing another variant of a finger-insertion member, which may be used in any of the sixth and seventh embodiments.

FIG. 41 shows another variant of finger-insertion member, which may be used in any of the sixth and seventh embodiments. As shown in FIG. 41, in the finger-insertion member 2206 or 2302, a pair of strain gauges 206 are disposed at two positions between which the elastic membrane 2211 lies. Consequently, at the measurement, two strain gauges 206 are aligned along the direction of the blood vessel. Therefore, it is possible to diagnose two pulse waveforms between which there is a time difference.

In addition, more than two strain gauges 206 may be provided along the direction of the radial artery. Moreover, it is possible to combine this variant with the aforementioned variant shown in FIG. 40, i.e., a pair of groups of abreast strain gauges 2150 are attached to two positions between which the elastic membrane 2211 lies.

Figure 42:
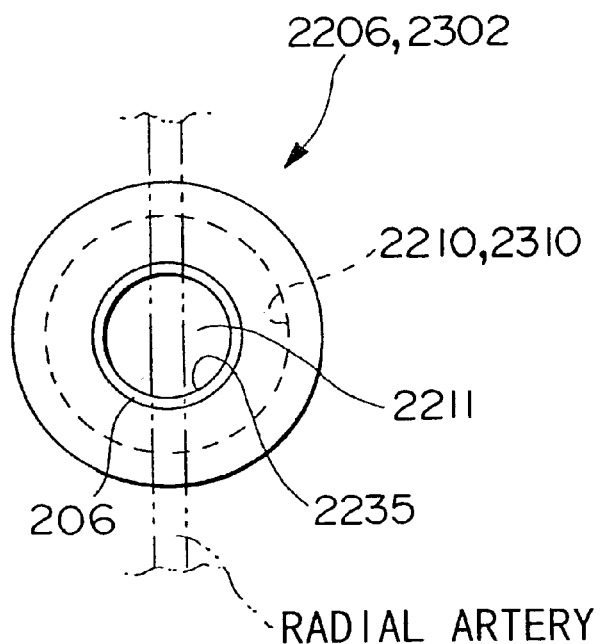
FIG. 42 is a bottom view showing another variant of a finger-insertion member, which may be used in any of the sixth and seventh embodiments.

Another modification of finger-insertion member, which may be used in any of the sixth and seventh embodiments, is shown in FIG. 42. As shown in FIG. 42, in the finger-insertion member 2206 or 2302, a ring-shaped strain gauge 206 is attached to the periphery of the opening 2235, so as to enclose the elastic membrane 2211. With such a structure, if the diagnosticians finger recognizes the radial artery over the elastic membrane 2211, the ring-shaped strain gauge 206 will be certainly in contact with the skin over the radial artery. Therefore, in spite of the direction of the finger-insertion member 2206 or 2302, the strain gauge 206 can be positioned on the skin above the radial artery. Consequently, it is unnecessary to use the groove 2212 for positioning the strain gauge 206 on the radial artery.

Figure 43:
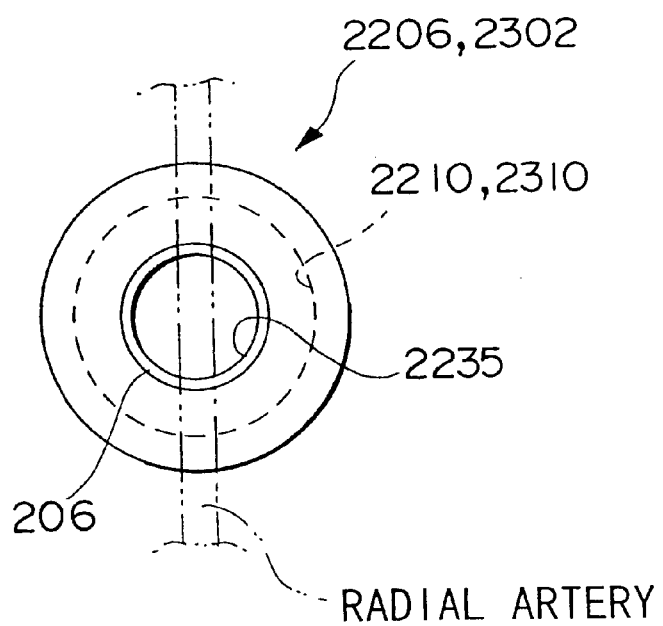
FIG. 43 is a bottom view showing another variant of a finger-insertion member, which may be used in any of the sixth and seventh embodiments.
Figure 44:
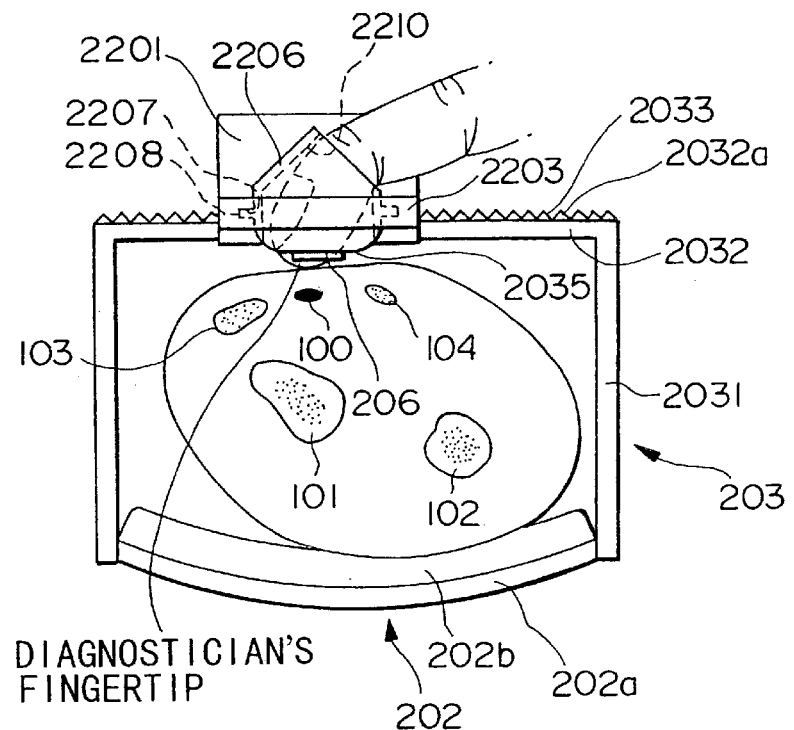
FIG. 44 is a front view showing the pulse wave measuring device according to the sixth embodiment, in which the finger-insertion member is replaced by that shown in FIG. 43, whereby the diagnostician directly touches the patient's arm and searches the measured position.

Another modification of finger-insertion member, which may be used in any of the sixth and seventh embodiments, is shown in FIG. 43. As shown in FIG. 43, in the finger-insertion member 2206 or 2302, the elastic membrane 2211 is not disposed at the opening 2235 of the insertion hole 2210 or 2310. Namely, the insertion-hole 2210 or 2310 is completely penetrated, so that the diagnostician can project his fingertip from the opening 2235. With such a structure, since the finger may touch the skin above the radial artery directly, the adjustment of the position of the strain gauge 206 can be facilitated in order to obtain more accurate measurement results.

It is not intended to limit the configuration of the insertion hole 2210 or 2310 to the aforementioned configuration, but rather any configuration permitting the inserted finger to detect the measured portion may be utilized. For example, it is possible to form the insertion hole into which a plurality of fingers can be inserted. Additionally, it is possible to arrange a plurality of finger-insertion members so as to align along the patient's radial artery.

Figure 46:
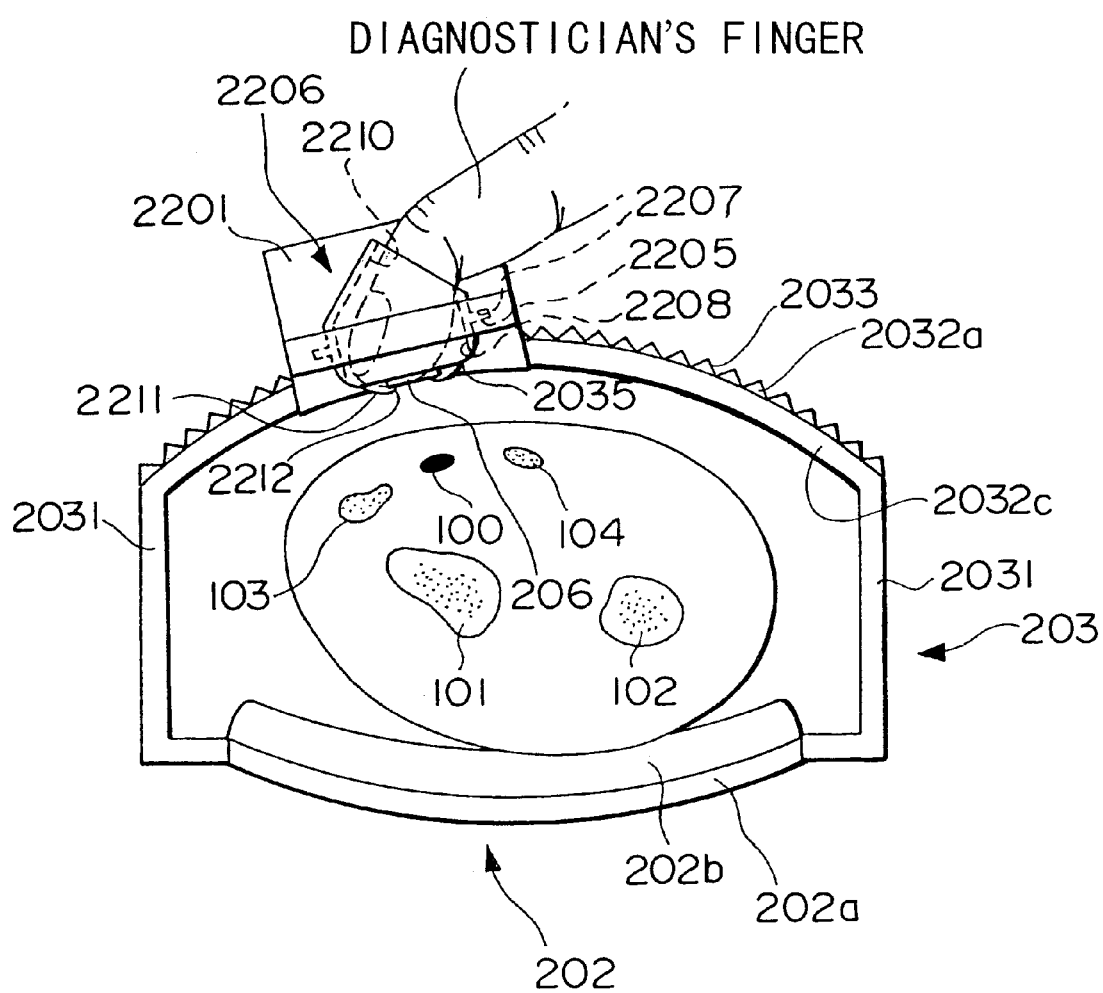
FIG. 46 is a front view showing another variant of the pulse wave measuring device according to any of the fifth through seventh embodiments, in which supporting members are modified.

In a variant of the pulse wave measuring device of the fifth through seventh embodiments, as shown in FIG. 46, it is possible to provide supporting portions 2032b instead of the straight supporting portions 2032 of the supporting members 203 on the arm holder 202. Both ends of each supporting portion 2032b are curved. Alternatively, as shown in FIG. 47, it is possible to provide supporting portions 2032c instead of the straight supporting portions 2032. Each supporting portion 2032c is curved entirely and the upper surface thereof is convex.

Figure 45:
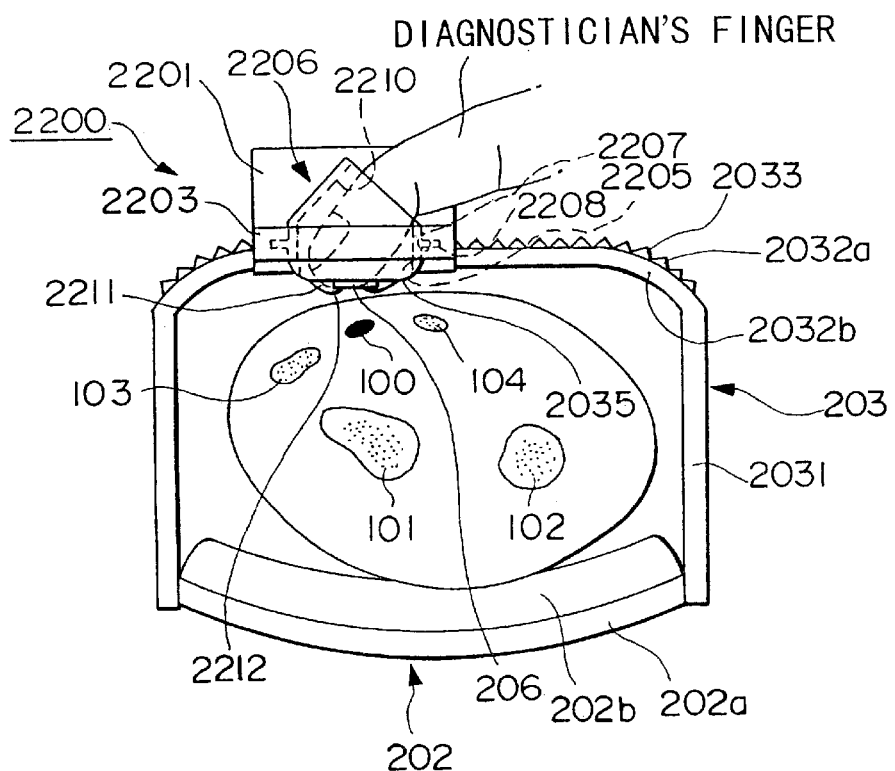
FIG. 45 is a front view showing a variant of the pulse wave measuring device according to any of the fifth through seventh embodiments, in which supporting members are modified.

By virtue of the arrangement shown in any of FIGS. 45 and 46, the strain gauge 206 can be moved in parallel with the arm's skin. Therefore, anywhere the strain gauge 206 is moved, the strain gauge 206 can give a pressure to the tangential plane of the patient's skin vertically (give a pressure on the patient's skin vertically), so that an accurate measurement is achieved.

Furthermore, it is possible to apply the pulse wave measuring device, according to any of the fifth to seventh embodiments, to the organism status diagnosing device disclosed in WO-97/16114 which diagnoses health central status on the basis of measurement of blood pulse wave at peripheral vessels. Since an accurate pulse waveform can be measured by virtue of the pulse wave measuring device according to any of the fifth to seventh embodiments, accurate central physiological status can be diagnosed using with the organism status diagnosing device.

Figure 17:
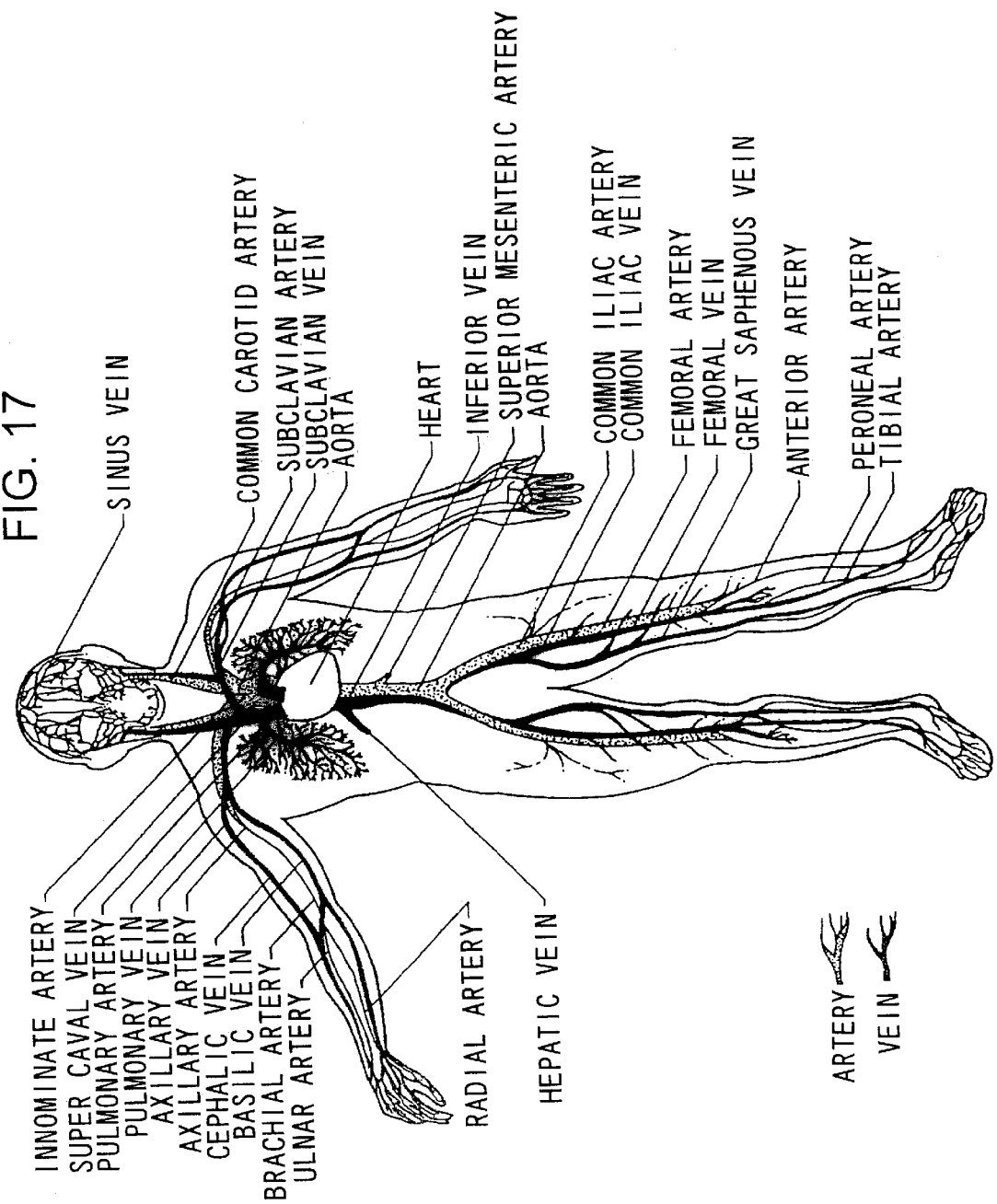
FIG. 17 is a diagram showing the blood circulation system of a human body, especially showing arteries and veins.

In any of the above-described embodiments, the measured vessel is the human radial artery, but it is not intended to limit the present invention thereto. If the supporting manner for the measurement device is modified, the device can measure pulse waves at other arteries, for example, the carotid artery. FIG. 17 shows various arteries and veins of a human being, and the device according to the present invention can measure the arteries illustrated here. Furthermore, it is possible to measure pulse waves of animals other than a human being.

In addition, it is not intended to limit the present invention to measure blood pulse waves of organism. Rather, the invented device can measure other articles where pulsation occurs.

Moreover, the pressure measuring device 80 can be used for another pressure measurement other than pulsation measurement.

What is claimed is:

1. A pulse wave measuring device for measuring pulse wave at a blood vessel of an organism, comprising:
    a vessel pressing portion being pressed against a skin over the blood vessel of the organism;
    a pulsation measuring sensor for measuring pulsation of the blood vessel pressed by the vessel pressing portion;
    two vessel-vicinity pressing portions being harder than the blood vessel of the organism and having distal ends, respectively, the distal ends being pressed against the skin of the organism at both sides of the vessel pressing portion; and
    adjusting means for adjusting an interval between the vessel-vicinity pressing portions.

2. A pulse wave measuring device according to claim 1, wherein the vessel pressing portion is situated back from the distal ends of the vessel-vicinity pressing portions.

3. A pulse wave measuring device according to claim 1, wherein the pulsation measuring sensor is a pressure sensor which outputs a pulse wave signal according to varying stress transmitted from the vessel pressing portion because of pulse wave of the blood vessel.

4. A pulse wave measuring device according to claim 3, further comprising:
    a beam supported by a support;
    a plurality of the vessel pressing portions provided at the beam and arranged at intervals along a direction of the blood vessel of the organism; and
    a plurality of the pressure sensors respectively corresponding to the vessel pressing portions.

5. A pulse wave measuring device according to claim 4, wherein each of the pressure sensors comprises a piezoelectric element mounted on the beam for outputting an electric signal according to varying stress transmitted from the corresponding vessel pressing portion, the beam including a proximal portion and a thinner portion formed between the proximal portion and the vessel pressing portions, the thinner portion being thinner than other portions of the beam, the piezoelectric element being longer than the thinner portion and mounted on the thinner portion entirely and on another portion, which is closer to the proximal portion or vessel pressing portion than the thinner portion, partially.

6. A pulse wave measuring device according to claim 4, wherein each of the pressure sensors comprises a piezoelectric element mounted on the beam for outputting an electric signal according to varying stress transmitted from the corresponding vessel pressing portion, an area of cross section of the thinner portion of the beam, on which the piezoelectric element is mounted, being equal to or less than 60% of an area of total cross section of the thinner portion and the piezoelectric element mounted thereon.

7. A pulse wave measuring device according to claim 5, wherein an area of cross section of the thinner portion of the beam, on which the piezoelectric element is mounted, is equal to or less than 60% of an area of total cross section of the thinner portion and the piezoelectric element mounted thereon.

8. A pulse wave measuring device according to claim 5, wherein the beam is divided so as to include a plurality of the thinner portions and the vessel pressing portions in order to measure stress variation at a plurality points on the blood vessel, and a plurality of the piezoelectric elements are provided on the thinner portions, respectively.

9. A pulse wave measuring device according to claim 1, wherein the pulsation measuring sensor comprises emitting means for emitting a wave which progresses toward the blood vessel; and receiving means for receiving the wave which is reflected from or penetrated through the blood vessel, and for outputting, on the basis of the received wave, a pulse wave signal according to pulse wave.

10. A pulse wave measuring device for measuring pulse wave at a blood vessel of an organism, comprising:
    a vessel pressing portion being pressed against a skin over the blood vessel of the organism;
    a pulsation measuring sensor for measuring pulsation of the blood vessel pressed by the vessel pressing portion; and
    two vessel-vicinity pressing portions being harder than the blood vessel of the organism and having distal ends, respectively, the distal ends being pressed against the skin of the organism at both sides of the vessel pressing portion, the vessel pressing portion being situated back from the distal ends of the vessel-vicinity pressing portions; and
    wherein the pulsation measuring sensor is a pressure sensor which outputs a pulse wave signal according to varying stress transmitted from the vessel pressing portion because of pulse wave of the blood vessel.

11. A pulse wave measuring device for measuring pulse wave at a blood vessel of an organism, comprising:
    a vessel pressing portion being pressed against a skin over the blood vessel of the organism;
    a pulsation measuring sensor for measuring pulsation of the blood vessel pressed by the vessel pressing portion; and
    two vessel-vicinity pressing portions being harder than the blood vessel of the organism and having distal ends, respectively, the distal ends being pressed against the skin of the organism at both sides of the vessel pressing portion, the vessel pressing portion being situated back from the distal ends of the vessel-vicinity pressing portions; and
    wherein the pulsation measuring sensor is a pressure sensor which outputs a pulse wave signal according to varying stress transmitted from the vessel pressing portion because of pulse wave of the blood vessel; and
    further comprising:
    a beam supported by a support;
    a plurality of the vessel pressing portions provided at the beam and arranged at intervals along a direction of the blood vessel of the organism; and
    a plurality of the pressure sensors respectively corresponding to the vessel pressing portions.

12. A pulse wave measuring device according to claim 11, wherein each of the pressure sensors comprises a piezoelectric element mounted on the beam for outputting an electric signal according to varying stress transmitted from the corresponding vessel pressing portion, the beam including a proximal portion and a thinner portion formed between the proximal portion and the vessel pressing portions, the thinner portion being thinner than other portions of the beam, the piezoelectric element being longer than the thinner portion and mounted on the thinner portion entirely and on another portion, which is closer to the proximal portion or vessel pressing portion than the thinner portion, partially.

13. A pulse wave measuring device according to claim 11, wherein each of the pressure sensors comprises a piezoelectric element mounted on the beam for outputting an electric signal according to varying stress transmitted from the corresponding vessel pressing portion, an area of cross section of the thinner portion of the beam, on which the piezoelectric element is mounted, being equal to or less than 60% of an area of total cross section of the thinner portion and the piezoelectric element mounted thereon.

14. A pulse wave measuring device according to claim 12, wherein an area of cross section of the thinner portion of the beam, on which the piezoelectric element is mounted, is equal to or less than 60% of an area of total cross section of the thinner portion and the piezoelectric element mounted thereon.

15. A pulse wave measuring device according to claim 12, wherein the beam is divided so as to include a plurality of the thinner portions and the vessel pressing portions in order to measure stress variation at a plurality points on the blood vessel, and a plurality of the piezoelectric elements are provided on the thinner portions, respectively.

16. A pulse wave measuring device for measuring pulse wave at a blood vessel of an organism, comprising:
- a vessel pressing portion being pressed against a skin over the blood vessel of the organism;
- a pulsation measuring sensor for measuring pulsation of the blood vessel pressed by the vessel pressing portion; and
- two vessel-vicinity pressing portions being harder than the blood vessel of the organism and having distal ends, respectively, the distal ends being pressed against the skin of the organism at both sides of the vessel pressing portion, the vessel pressing portion being situated back from the distal ends of the vessel-vicinity pressing portions; and
- wherein the pulsation measuring sensor comprises emitting means for emitting a wave which progresses toward the blood vessel; and receiving means for receiving the wave which is reflected from or penetrated through the blood vessel, and for outputting, on the basis of the received wave, a pulse wave signal according to pulse wave.

17. A pulse wave measuring device for measuring a pulse wave at a blood vessel of an organism, comprising:
- a beam supported by a support;
- a plurality of vessel pressing portions provided at the beam and arranged at intervals along a direction of the blood vessel of the organism, each of the vessel pressing portion being pressed against a skin over the blood vessel of the organism;
- a plurality of pressure sensors respectively corresponding to the vessel pressing portions, each of the pressure sensors outputting a pulse wave signal according to varying stress transmitted from the corresponding vessel pressing portion because of pulse wave of the blood vessel; and
- two vessel-vicinity pressing portions being harder than the blood vessel of the organism and having distal ends, respectively, the distal ends being pressed against the skin of the organism at both sides of the vessel pressing portions.

18. A pulse wave measuring device according to claim 17, wherein each of the pressure sensors comprises a piezoelectric element mounted on the beam for outputting an electric signal according to varying stress transmitted from the corresponding vessel pressing portion, the beam including a proximal portion and a thinner portion formed between the proximal portion and the vessel pressing portions, the thinner portion being thinner than other portions of the beam, the piezoelectric element being longer than the thinner portion and mounted on the thinner portion entirely and on another portion, which is closer to the proximal portion or vessel pressing portion than the thinner portion, partially.

19. A pulse wave measuring device according to claim 17, wherein each of the pressure sensors comprises a piezoelectric element mounted on the beam for outputting an electric signal according to varying stress transmitted from the corresponding vessel pressing portion, an area of cross section of the thinner portion of the beam, on which the piezoelectric element is mounted, being equal to or less than 60% of an area of total cross section of the thinner portion and the piezoelectric element mounted thereon.

20. A pulse wave measuring device according to claim 18, wherein an area of cross section of the thinner portion of the beam, on which the piezoelectric element is mounted, is equal to or less than 60% of an area of total cross section of the thinner portion and the piezoelectric element mounted thereon.

21. A pulse wave measuring device according to claim 18, wherein the beam is divided so as to include a plurality of the thinner portions and the vessel pressing portions in order to measure stress variation at a plurality points on the blood vessel, and a plurality of the piezoelectric elements are provided on the thinner portions, respectively.

22. A pulse wave measuring device comprising:
- a supporting member;
- a perpendicular sliding member which is supported by the supporting member and slidable perpendicularly in relation to the supporting member;
- measuring means situated at the perpendicular sliding member for measuring pulse wave at a blood vessel of an organism; and
- first and second toothed portions formed at mutual sliding faces of the supporting member and the perpendicular sliding member, respectively and meshed with each other.

23. A pulse wave measuring device according to claim 22, wherein first and second toothed portions are formed so as to restrict mutual slide of the supporting member and the perpendicular sliding member if a pulsation force is exerted thereto along their slidable direction when measuring pulse wave.

24. A pulse wave measuring device according to claim 22, wherein the perpendicular sliding member includes an insertion hole, in which a diagnostician's finger can be inserted, and an elastic membrane arranged within the insertion hole and at one end of the insertion hole.

25. A pulse wave measuring device according to claim 24, wherein a groove is formed at the elastic membrane, the skin over the blood vessel of the organism being capable of positioned into the groove.

26. A pulse wave measuring device according to claim 25, wherein the perpendicular sliding member is provided with finger-insertion means at which the insertion hole is formed, the finger-insertion means being rotatable in relation to the perpendicular sliding member.

27. A pulse wave measuring device according to claim 25, wherein the perpendicular sliding member is provided with a pull portion on which a diagnostician's finger can pull, so as to slide the perpendicular sliding member.

28. A pulse wave measuring device according to claim 22, wherein the perpendicular sliding member includes an insertion hole penetrating perpendicularly, so that a diagnostician's finger can pass therethrough.

29. A pulse wave measuring device comprising:
a supporting member;
a transverse sliding member which is supported by the supporting member and slidable transversely in relation to the supporting member;
a perpendicular sliding member which is supported by the transverse sliding member and slidable perpendicularly in relation to the transverse sliding member;
measuring means situated at the perpendicular sliding member for measuring pulse wave at a blood vessel of an organism;
third and fourth toothed portions formed at mutual sliding faces of the supporting member and the transverse sliding member, respectively and meshed with each other; and
fifth and sixth toothed portions formed at mutual sliding faces of the transverse sliding member and the perpendicular sliding member, respectively and meshed with each other.

30. A pulse wave measuring device according to claim 29, wherein fifth and sixth toothed portions are formed so as to restrict mutual slide of the transverse sliding member and the perpendicular sliding member if a pulsation force is exerted thereto along their slidable direction when measuring pulse wave.

31. A pulse wave measuring device according to claim 29, wherein the perpendicular sliding member includes an insertion hole, in which a diagnostician's finger can be inserted, and an elastic membrane arranged within the insertion hole and at one end of the insertion hole.

32. A pulse wave measuring device according to claim 31, wherein a groove is formed at the elastic membrane, the skin over the blood vessel of the organism being capable of positioned into the groove.

33. A pulse wave measuring device according to claim 32, wherein the perpendicular sliding member is provided with finger-insertion means at which the insertion hole is formed, the finger-insertion means being rotatable in relation to the perpendicular sliding member.

34. A pulse wave measuring device according to claim 32, wherein the perpendicular sliding member is provided with a pull portion on which a diagnostician's finger can pull, so as to slide the perpendicular sliding member.

35. A pulse wave measuring device according to 29, wherein the perpendicular sliding member includes an insertion hole penetrating perpendicularly so that a diagnostician's finger can pass therethrough.

36. A pulse wave measuring device comprising:
a supporting member;
a perpendicular sliding member which is supported by the supporting member and slidable perpendicularly in relation to the supporting member;
a transverse sliding member which is supported by the perpendicular sliding member and slidable transversely in relation to the perpendicular sliding member;
measuring means situated at the transverse sliding member for measuring a pulse wave at a blood vessel of an organism;
seventh and eighth toothed portions formed at mutual sliding faces of the supporting member and the perpendicular sliding member, respectively and meshed with each other; and
ninth and tenth toothed portions formed at mutual sliding faces of the perpendicular sliding member and the transverse sliding member, respectively and meshed with each other.

37. A pulse wave measuring device according to claim 36, wherein seventh and eighth toothed portions are formed so as to restrict mutual slide of the supporting member and the perpendicular sliding member if a pulsation force is exerted thereto along their slidable direction when measuring pulse wave.

38. A pulse wave measuring device according to claim 36, wherein the transverse sliding member includes an insertion hole, in which a diagnostician's finger can be inserted, and an elastic membrane arranged within the insertion hole and at one end of the insertion hole.

39. A pulse wave measuring device according to claim 38, wherein a groove is formed at the elastic membrane, the skin over the blood vessel of the organism being capable of positioned into the groove.

40. A pulse wave measuring device according to claim 39, wherein the transverse sliding member is provided with finger-insertion means at which the insertion hole is formed, the finger-insertion means being rotatable in relation to the transverse sliding member.

41. A pulse wave measuring device according to claim 36, wherein the transverse sliding member includes an insertion hole penetrating perpendicularly, whereby a diagnostician's finger can pass therethrough.

42. A pulse wave measuring device comprising:
a supporting member;
a transverse sliding member which is supported by the supporting member and slidable transversely in relation to the supporting member, a screw hole being formed perpendicularly at the transverse sliding member;
eleventh and twelfth toothed portions formed at mutual sliding faces of the supporting member and the transverse sliding member, respectively and meshed with each other;
a perpendicular sliding member which is screwed in the screw hole of the transverse sliding member and movable perpendicularly to the transverse sliding member by rotation; and
measuring means situated at the perpendicular sliding member for measuring pulse wave at a blood vessel of an oryanism.

43. A pulse wave measuring device according to claim 42, wherein the perpendicular sliding member includes an insertion hole, in which a diagnostician's finger can be inserted, and an elastic membrane arranged within the insertion hole and at one end of the insertion hole.

44. A pulse wave measuring device according to claim 43, wherein a groove is formed at the elastic membrane, the skin over the blood vessel of the organism being capable of positioned into the groove.

45. A pulse wave measuring device according to claim 42, wherein the transverse sliding member includes an insertion hole penetrating perpendicularly, whereby a diagnostician's finger can pass therethrough.

46. A pulsation measuring device for measuring pulsation at a measured subject of a measured thing, comprising:

a subject pressing portion being pressed against a covering over the measured subject of the measured thing;

a pulsation measuring sensor for measuring pulsation of the measured subject pressed by the subject pressing portion;

two subject-vicinity pressing portions being harder than the measured subject of the measured thing and having distal ends, respectively the distal ends being pressed against the covering of the measured thing at both sides of the subject pressing portion; and adjusting means for adjusting an interval between the subject-vicinity pressing portions.

47. A pulsation measuring device according to claim 46, wherein the subject pressing portion is situated back from the distal ends of the subject-vicinity pressing portions.

48. A pulsation measuring device according to claim 46, wherein the pulsation measuring sensor is a pressure sensor which outputs a pulsation signal according to varying stress transmitted from the subject pressing portion because of pulsation of the measured subject.

49. A pulsation measuring device according to claim 48, further comprising:

a beam supported by a support;

a plurality of the subject pressing portions provided at the beam and arranged at intervals along a direction of the measured subject of the measured thing; and a plurality of the pressure sensors respectively corresponding to the subject pressing portions.

50. A pulsation measuring device according to claim 49, wherein each of the pressure sensors comprises a piezoelectric element mounted on the beam for outputting an electric signal according to varying stress transmitted from the corresponding subject pressing portion, the beam including a proximal portion and a thinner portion formed between the proximal portion and the subject pressing portions, the thinner portion being thinner than other portions of the beam, the piezoelectric element being longer than the thinner portion and mounted on the thinner portion entirely and on another portion, which is closer to the proximal portion or subject pressing portion than the thinner portion, partially.

51. A pulsation measuring device according to claim 49, wherein each of the pressure sensors comprises a piezoelectric element mounted on the beam for outputting an electric signal according to varying stress transmitted from the corresponding subject pressing portion, an area of cross section of the thinner portion of the beam, on which the piezoelectric element is mounted, being equal to or less than 60% of an area of total cross section of the thinner portion and the piezoelectric element mounted thereon.

52. A pulsation measuring device according to claim 50, wherein an area of cross section of the thinner portion of the beam, on which the piezoelectric element is mounted, is equal to or less than 60% of an area of total cross section of the thinner portion and the piezoelectric element mounted thereon.

53. A pulsation measuring device according to claim 50, wherein the beam is divided so as to include a plurality of the thinner portions and the subject pressing portions in order to measure stress variation at a plurality points on the measured subject, and a plurality of the piezoelectric elements are provided on the thinner portions, respectively.

54. A pulsation measuring device according to claim 46, wherein the pulsation measuring sensor comprises emitting means for emitting a wave which progresses toward the measured subject; and receiving means for receiving the wave which is reflected from or penetrated through the measured subject, and for outputting, on the basis of the received wave, a pulsation signal according to pulsation.

55. A pulsation measuring device for measuring pulsation at a measured subject of a measured thing, comprising:

a subject pressing portion being pressed against a covering over the measured subject of the measured thing;

a pulsation measuring sensor for measuring pulsation of the measured subject pressed by the subject pressing portion; and two subject-vicinity pressing portions being harder than the measured subject of the measured thing and having distal ends, respectively, the distal ends being pressed against the covering of the measured thing at both sides of the subject pressing portion, the subject pressing portion being situated back from the distal ends of the subject-vicinity pressing portions; and wherein the pulsation measuring sensor is a pressure sensor which outputs a pulsation signal according to varying stress transmitted from the subject pressing portion because of pulsation of the measured subject.

56. A pulsation measuring device for measuring pulsation at a measured subject of a measured thing, comprising:

a subject pressing portion being pressed against a covering over the measured subject of the measured thing;

a pulsation measuring sensor for measuring pulsation of the measured subject pressed by the subject pressing portion; and two subject-vicinity pressing portions being harder than the measured subject of the measured thing and having distal ends, respectively, the distal ends being pressed against the covering of the measured thing at both sides of the subject pressing portion, the subject pressing portion being situated back from the distal ends of the subject-vicinity pressing portions; and wherein the pulsation measuring sensor is a pressure sensor which outputs a pulsation signal according to varying stress transmitted from the subject pressing portion because of pulsation of the measured subject; and further comprising:

a beam supported by a support;

a plurality of the subject pressing portions provided at the beam and arranged at intervals along a direction of the measured subject of the measured thing; and a plurality of the pressure sensors respectively corresponding to the subject pressing portions.

57. A pulsation measuring device according to claim 56, wherein each of the pressure sensors comprises a piezoelectric element mounted on the beam for outputting an electric signal according to varying stress transmitted from the corresponding subject pressing portion, the beam including a proximal portion and a thinner portion formed between the proximal portion and the subject pressing portions, the thinner portion being thinner than other portions of the beam, the piezoelectric element being longer than the thinner portion and mounted on the thinner portion entirely and on another portion, which is closer to the proximal portion or subject pressing portion than the thinner portion, partially.

58. A pulsation measuring device according to claim 56, wherein each of the pressure sensors comprises a piezoelectric element mounted on the beam for outputting an electric signal according to varying stress transmitted from the corresponding subject pressing portion, an area of cross section of the thinner portion of the beam, on which the piezoelectric element is mounted, being equal to or less than 60% of an area of total cross section of the thinner portion and the piezoelectric element mounted thereon.

59. A pulsation measuring device according to claim 57, wherein wherein an area of cross section of the thinner portion of the beam, on which the piezoelectric element is mounted, is equal to or less than 60% of an area of total cross section of the thinner portion and the piezoelectric element mounted thereon.

60. A pressure measuring device device according to claim 57, wherein the beam is divided so as to include a plurality of the thinner portions and the subject pressing portions in order to measure stress variation at a plurality points on the measured subject, and a plurality of the piezoelectric elements are provided on the thinner portions, respectively.

61. A pulsation measuring device for measuring pulsation at a measured subject of a measured thing, comprising:

a subject pressing portion being pressed against a covering over the measured subject of the measured thing;

a pulsation measuring sensor for measuring pulsation of the measured subject pressed by the subject pressing portion; and two subject-vicinity pressing portions being harder than the measured subject of the measured thing and having distal ends, respectively, the distal ends being pressed against the covering of the measured thing at both sides of the subject pressing portion, the subject pressing portion being situated back from the distal ends of the subject-vicinity pressing portions; and wherein the pulsation measuring sensor comprises emitting means for emitting a wave which progresses toward the measured subject; and receiving means for receiving the wave which is reflected from or penetrated through the measured subject, and for outputting, on the basis of the received wave, a pulsation signal according to pulsation.

62. A pulsation measuring device for measuring pulsation at a measured subject of a measured thing, comprising:

a beam supported by a support;

a plurality of subject pressing portions provided at the beam and arranged at intervals along a direction of the measured subject of the measured thing, each of the subject pressing portion being pressed against a covering over the measured subject of the measured thing;

a plurality of pressure sensors respectively corresponding to the subject pressing portions, each of the pressure sensors outputting a pulsation signal according to varying stress transmitted from the corresponding subject pressing portion because of pulsation of the measured subject; and two subject-vicinity pressing portions being harder than the measured subject of the measured thing and having distal ends, respectively, the distal ends being pressed against the covering of the measured thing at both sides of the subject pressing portions.

63. A pulsation measuring device according to claim 62, wherein each of the pressure sensors comprises a piezoelectric element mounted on the beam for outputting an electric signal according to varying stress transmitted from the corresponding subject pressing portion, the beam including a proximal portion and a thinner portion formed between the proximal portion and the subject pressing portions, the thinner portion being thinner than other portions of the beam, the piezoelectric element being longer than the thinner portion and mounted on the thinner portion entirely and on another portion, which is closer to the proximal portion or subject pressing portion than the thinner portion, partially.

64. A pulsation measuring device according to claim 62, wherein each of the pressure sensors comprises a piezoelectric element mounted on the beam for outputting an electric signal according to varying stress transmitted from the corresponding subject pressing portion, an area of cross section of the thinner portion of the beam, on which the piezoelectric element is mounted, being equal to or less than 60% of an area of total cross section of the thinner portion and the piezoelectric element mounted thereon.

65. A pulsation measuring device according to claim 63, wherein an area of cross section of the thinner portion of the beam, on which the piezoelectric element is mounted, is equal to or less than 60% of an area of total cross section of the thinner portion and the piezoelectric element mounted thereon.

66. A pulsation measuring device according to claim 63, wherein the beam is divided so as to include a plurality of the thinner portions and the subject pressing portions in order to measure stress variation at a plurality points on the measured subject, and a plurality of the piezoelectric elements are provided on the thinner portions, respectively.

67. A pulsation measuring device comprising:

a supporting member;

a perpendicular sliding member which is supported by the supporting member and slidable perpendicularly in relation to the supporting member;

measuring means situated at the perpendicular sliding member for measuring pulsation at a measured subject of a measured thing; and first and second toothed portions formed at mutual sliding faces of the supporting member and the perpendicular sliding member, respectively and meshed with each other.

68. A pulsation measuring device according to claim 67, wherein first and second toothed portions are formed so as to restrict mutual slide of the supporting member and the perpendicular sliding member if a pulsation force is exerted thereto along their slidable direction when measuring pulsation.

69. A pulsation measuring device according to claim 67, wherein the perpendicular sliding member includes an insertion hole, in which a measurer's finger can be inserted, and an elastic membrane arranged within the insertion hole and at one end of the insertion hole.

70. A pulsation measuring device according to claim 69, wherein a groove is formed at the elastic membrane, the covering over the measured subject of the measured thing being capable of positioned into the groove.

71. A pulsation measuring device according to claim 70, wherein the perpendicular sliding member is provided with finger-insertion means at which the insertion hole is formed, the finger-insertion means being rotatable in relation to the perpendicular sliding member.

72. A pulsation measuring device according to claim 70, wherein the perpendicular sliding member is provided with a pull portion on which a measurer's finger can pull, so as to slide the perpendicular sliding member.

73. A pulsation measuring device according to claim 67, wherein the perpendicular sliding member includes an insertion hole penetrating perpendicularly, so that a measurer's finger can pass therethrough.

74. A pulsation measuring device comprising:

a supporting member;

a transverse sliding member which is supported by the supporting member and slidable transversely in relation to the supporting member;

a perpendicular sliding member which is supported by the transverse sliding member and slidable perpendicularly in relation to the transverse sliding member;

measuring means situated at the perpendicular sliding member for measuring pulsation at a measured subject of a measured thing;

third and fourth toothed portions formed at mutual sliding faces of the supporting member and the transverse sliding member, respectively and meshed with each other; and fifth and sixth toothed portions formed at mutual sliding faces of the transverse sliding member and the perpendicular sliding member, respectively and meshed with each other.

75. A pulsation measuring device according to claim 74, wherein fifth and sixth toothed portions are formed so as to restrict mutual slide of the transverse sliding member and the perpendicular sliding member if a pulsation force is exerted thereto along their slidable direction when measuring pulsation.

76. A pulsation measuring device according to claim 74, wherein the perpendicular sliding member includes an insertion hole, in which a measurer's finger can be inserted, and an elastic membrane arranged within the insertion hole and at one end of the insertion hole.

77. A pulsation measuring device according to claim 76, wherein a groove is formed at the elastic membrane, the covering over the measured subject of the measured thing being capable of positioned into the groove.

78. A pulsation measuring device according to claim 77, wherein the perpendicular sliding member is provided with finger-insertion means at which the insertion hole is formed, the finger-insertion means being rotatable in relation to the perpendicular sliding member.

79. A pulsation measuring device according to claim 77, wherein the perpendicular sliding member is provided with a pull portion on which a measurer's finger can pull, so as to slide the perpendicular sliding member.

80. A pulsation measuring device according to claim 74, wherein the perpendicular sliding member includes an insertion hole penetrating perpendicularly, so that a measurer's finger can pass therethrough.

81. A pulsation measuring device comprising:

a supporting member;

a perpendicular sliding member which is supported by the supporting member and slidable perpendicularly in relation to the supporting member;

a transverse sliding member which is supported by the perpendicular sliding member and slidable transversely in relation to the perpendicular sliding member;

measuring means situated at the transverse sliding member for measuring pulsation at a measured subject of a measured thing;

seventh and eighth toothed portions formed at mutual sliding faces of the supporting member and the perpendicular sliding member, respectively and meshed with each other; and ninth and tenth toothed portions formed at mutual sliding faces of the perpendicular sliding member and the transverse sliding member, respectively and meshed with each other.

82. A pulsation measuring device according to claim 81, wherein seventh and eighth toothed portions are formed so as to restrict mutual slide of the supporting member and the perpendicular sliding member if a pulsation force is exerted thereto along their slidable direction when measuring pulsation.

83. A pulsation measuring device according to claim 81, wherein the transverse sliding member includes an insertion hole, in which a measurer's finger can be inserted, and an elastic membrane arranged within the insertion hole and at one end of the insertion hole.

84. A pulsation measuring device according to claim 83, wherein a groove is formed at the elastic membrane, the covering over the measured subject of the measured thing being capable of positioned into the groove.

85. A pulsation measuring device according to claim 84, wherein the transverse sliding member is provided with finger-insertion means at which the insertion hole is formed, the finger-insertion means being rotatable in relation to the transverse sliding member.

86. A pulsation measuring device according to claim 81, wherein the transverse sliding member includes an insertion hole penetrating perpendicularly, whereby a measurer's finger can pass therethrough.

87. A pulsation measuring device comprising:

a supporting member;

a transverse sliding member which is supported by the supporting member and slidable transversely in relation to the supporting member, a screw hole being formed perpendicularly at the transverse sliding member;

eleventh and twelfth toothed portions formed at mutual sliding faces of the supporting member and the transverse sliding member, respectively and meshed with each other;

a perpendicular sliding member which is screwed in the screw hole of the transverse sliding member and movable perpendicularly to the transverse sliding member by rotation; and measuring means situated at the perpendicular sliding member for measuring pulsation at a measured subject of a measured thing.

88. A pulsation measuring device according to claim 87, wherein the perpendicular sliding member includes an insertion hole, in which a measurer's finger can be inserted, and an elastic membrane arranged within the insertion hole and at one end of the insertion hole.

89. A pulsation measuring device according to claim 88, wherein a groove is formed at the elastic membrane, the covering over the measured subject of the measured thing being capable of positioned into the groove.

90. A pulsation measuring device according to claim 87, wherein the transverse sliding member includes an insertion hole penetrating perpendicularly, whereby a measurer's finger can pass therethrough.

91. A pressure measuring device comprising:

a beam having at least one proximal portion supported by a support;

a subject pressing portion provided at the beam and pressed against a measured subject; and a piezoelectric element mounted on the beam for outputting an electric signal according to varying stress transmitted from the subject pressing portion, the beam including a thinner portion formed between the proximal portion and the subject pressing portion, the thinner portion being thinner than other portions of the beam, the piezoelectric element being longer than the thinner portion and mounted on the thinner portion entirely and on another portion partially, which is closer to the proximal portion or subject pressing portion than the thinner portion.

92. A pressure measuring device according to claim 91, wherein an area of cross section of the thinner portion of the beam, on which the piezoelectric element is mounted, is equal to or less than 60% of an area of total cross section of the thinner portion and the piezoelectric element mounted thereon.

93. A pressure measuring device according to claim 91, wherein the beam is divided so as to include a plurality of thinner portions and the subject pressing portions in order to measure stress variation at a plurality points on the measured subject, and a plurality of the piezoelectric elements are provided on the thinner portions, respectively.

94. A pressure measuring device comprising:
   a beam having at least one proximal portion supported by a support;
   a subject pressing portion provided at the beam and pressed against a measured subject; and
   a piezoelectric element mounted on the beam for outputting an electric signal according to varying stress transmitted from the subject pressing portion, an area of cross section of the thinner portion of the beam, on which the piezoelectric element is mounted, being equal to or less than 60% of an area of total cross section of the thinner portion and the piezoelectric element mounted thereon.

* * * * *

UNITED STATES PATENT AND TRADEMARK OFFICE
CERTIFICATE OF CORRECTION

PATENT NO. : 6,210,340 B1
DATED : April 3, 2001
INVENTOR(S) : Kazuhiko Amano et al.

It is certified that error appears in the above-identified patent and that said Letters Patent is hereby corrected as shown below:

Column 35,
Line 57, insert -- , -- after "perpendicularly".

Column 36,
Line 52, change "oryanism" to -- organism --.

Column 37,
Line 8, insert -- , -- after "respectively".

Column 39,
Line 4, delete second occurrence of "wherein".
Line 9, delete second occurrence of "device".

Signed and Sealed this

Sixteenth Day of July, 2002

*Attest:*

JAMES E. ROGAN
*Attesting Officer*   *Director of the United States Patent and Trademark Office*